(12) United States Patent
Dimitroff et al.

(10) Patent No.: US 7,767,820 B2
(45) Date of Patent: Aug. 3, 2010

(54) SUBSTITUTED BENZIMIDAZOLES AND METHODS OF PREPARATION

(75) Inventors: Martin Dimitroff, Seattle, WA (US); Bridget R. Miller, Lynnwood, WA (US); Brady S. Stillwell, Gregory, MI (US); David A. Siesel, San Diego, CA (US); Tyson Swiftney, Bellevue, WA (US); Brian Diaz, Seattle, WA (US); Danlin Gu, Kirkland, WA (US); Jonathan P. Van Dyck, Seattle, WA (US); David Ryckman, Bellevue, WA (US); Daniel J. Poon, Oakland, CA (US); Teresa E. Pick, Danville, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

(21) Appl. No.: 12/151,995

(22) Filed: May 5, 2008

(65) Prior Publication Data
US 2008/0287682 A1 Nov. 20, 2008

Related U.S. Application Data

(63) Continuation of application No. 11/513,745, filed on Aug. 30, 2006, now abandoned.

(60) Provisional application No. 60/713,108, filed on Aug. 30, 2005, provisional application No. 60/712,539, filed on Aug. 30, 2005, provisional application No. 60/731,591, filed on Oct. 27, 2005, provisional application No. 60/774,684, filed on Feb. 17, 2006.

(51) Int. Cl.
C07D 401/14 (2006.01)
(52) U.S. Cl. .................................. 546/273.4
(58) Field of Classification Search ............... 546/273.4; 544/364
See application file for complete search history.

(56) References Cited

U.S. PATENT DOCUMENTS

| | | | |
|---|---|---|---|
| 3,894,037 A | 7/1975 | Brenneisen et al. |
| 4,197,307 A | 4/1980 | Gallay et al. |
| 4,231,938 A | 11/1980 | Monaghan et al. |
| 4,294,926 A | 10/1981 | Monaghan et al. |
| 4,319,039 A | 3/1982 | Albers-Schonberg |
| 4,346,227 A | 8/1982 | Terahara et al. |
| 4,410,629 A | 10/1983 | Terahara et al. |
| 4,430,502 A | 2/1984 | Nelson |
| 4,444,784 A | 4/1984 | Hoffman et al. |
| 4,537,859 A | 8/1985 | Terahara et al. |
| 4,563,455 A | 1/1986 | Ueda et al. |
| 4,681,893 A | 7/1987 | Roth |
| 4,782,084 A | 11/1988 | Vyas et al. |
| 4,820,850 A | 4/1989 | Verhoeven et al. |
| 4,885,314 A | 12/1989 | Vyas et al. |
| 4,911,165 A | 3/1990 | Lennard et al. |
| 4,916,239 A | 4/1990 | Treiber |
| 4,929,437 A | 5/1990 | Tobert |
| 5,030,447 A | 7/1991 | Joshi et al. |
| 5,041,453 A | 8/1991 | Huang et al. |
| 5,118,853 A | 6/1992 | Lee et al. |
| 5,134,142 A | 7/1992 | Matsuo et al. |
| 5,141,950 A | 8/1992 | Nakane et al. |
| 5,180,589 A | 1/1993 | Joshi et al. |
| 5,189,164 A | 2/1993 | Kapa et al. |
| 5,273,995 A | 12/1993 | Roth |
| 5,290,946 A | 3/1994 | Lee et al. |
| 5,342,952 A | 8/1994 | Butler et al. |
| 5,344,991 A | 9/1994 | Reitz et al. |
| 5,354,772 A | 10/1994 | Kathawala |
| 5,356,896 A | 10/1994 | Kabadi et al. |
| 5,380,738 A | 1/1995 | Norman et al. |
| 5,393,790 A | 2/1995 | Reitz et al. |
| 5,409,944 A | 4/1995 | Black et al. |
| 5,420,245 A | 5/1995 | Brown et al. |
| 5,436,265 A | 7/1995 | Black et al. |
| 5,446,059 A | 8/1995 | Rocher et al. |
| 5,466,823 A | 11/1995 | Talley et al. |
| 5,474,995 A | 12/1995 | Ducharme et al. |
| 5,489,691 A | 2/1996 | Butler et al. |
| 5,510,510 A | 4/1996 | Patel et al. |
| 5,523,430 A | 6/1996 | Patel et al. |

(Continued)

FOREIGN PATENT DOCUMENTS

AU 200039816 A1 11/2000

(Continued)

OTHER PUBLICATIONS

Balant et al. "Metabolic Considerations, etc.," in Manfred ed., Burger's Medicinal Chemistry and Drug Discovery 5th ed., vol. 1: Principles and Practice, John Wiley & Sons, Inc., 1995.*

(Continued)

*Primary Examiner*—Patricia L Morris
(74) *Attorney, Agent, or Firm*—Swiss Tanner, P.C.

(57) ABSTRACT

Methods for preparing new substituted benzimidazole compounds having formula (I) useful for treating kinase mediated disorders are provided wherein $R^1$, $R^2$, $R^3$, $R^4$, a, b, and c are defined herein (I)

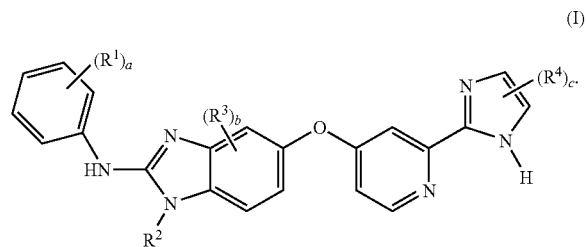

12 Claims, No Drawings

U.S. PATENT DOCUMENTS

| | | | |
|---|---|---|---|
| 5,532,359 | A | 7/1996 | Marsters, Jr. et al. |
| 5,536,752 | A | 7/1996 | Ducharme et al. |
| 5,550,142 | A | 8/1996 | Ducharme et al. |
| 5,571,792 | A | 11/1996 | Bolton et al. |
| 5,589,485 | A | 12/1996 | Hochlowski et al. |
| 5,602,098 | A | 2/1997 | Sebti et al. |
| 5,604,260 | A | 2/1997 | Guay et al. |
| 5,633,272 | A | 5/1997 | Talley et al. |
| 5,661,152 | A | 8/1997 | Bishop et al. |
| 5,693,633 | A | 12/1997 | Boyd et al. |
| 5,698,584 | A | 12/1997 | Black et al. |
| 5,710,140 | A | 1/1998 | Ducharme et al. |
| 5,717,100 | A | 2/1998 | Selnick et al. |
| 5,852,046 | A | 12/1998 | Lang et al. |
| 5,861,419 | A | 1/1999 | Dube et al. |
| 5,932,598 | A | 8/1999 | Talley et al. |
| 5,932,600 | A | 8/1999 | Saunders et al. |
| 5,972,968 | A | 10/1999 | De Nanteuil et al. |
| 6,001,843 | A | 12/1999 | Dube et al. |
| 6,001,866 | A | 12/1999 | Cornicelli et al. |
| 6,020,343 | A | 2/2000 | Belley et al. |
| 6,037,136 | A | 3/2000 | Beach et al. |
| 6,040,327 | A | 3/2000 | De Nanteuil et al. |
| 6,121,308 | A | 9/2000 | Hauel et al. |
| 6,127,380 | A | 10/2000 | Nelson et al. |
| 6,127,389 | A | 10/2000 | Oku et al. |
| 6,172,073 | B1 | 1/2001 | Audia et al. |
| 6,204,467 | B1 | 3/2001 | Greenholtz, Jr. et al. |
| 6,211,177 | B1 | 4/2001 | Sperl et al. |
| 6,268,391 | B1 | 7/2001 | Dickerson et al. |
| 6,281,193 | B1 | 8/2001 | Strom et al. |
| 6,284,781 | B1 | 9/2001 | Danishefsky et al. |
| 6,288,237 | B1 | 9/2001 | Hoefle et al. |
| 6,352,985 | B1 | 3/2002 | Yamasaki et al. |
| 6,353,108 | B1 | 3/2002 | Bouchet et al. |
| 6,358,932 | B1 | 3/2002 | Monia |
| 6,391,636 | B1 | 5/2002 | Monia |
| 6,458,813 | B1 | 10/2002 | Mantlo et al. |
| 6,509,336 | B1 | 1/2003 | Dong et al. |
| 6,509,357 | B1 | 1/2003 | Zhou et al. |
| 6,515,133 | B1 | 2/2003 | Thurkauf et al. |
| 6,518,291 | B1 | 2/2003 | Saunder et al. |
| 6,548,520 | B1 | 4/2003 | Adams et al. |
| 6,706,738 | B2 | 3/2004 | Clark et al. |
| 6,710,069 | B2 | 3/2004 | Zhou et al. |
| 6,756,410 | B2 | 6/2004 | Mehta |
| 6,855,714 | B2 | 2/2005 | Blume et al. |
| 6,911,446 | B2 | 6/2005 | Tang et al. |
| 6,919,354 | B2 | 7/2005 | Zhou et al. |
| 7,071,216 | B2 | 7/2006 | Renhowe et al. |
| 7,482,367 | B2 | 1/2009 | Aikawa et al. |
| 2001/0006975 | A1 | 7/2001 | Wood et al. |
| 2002/0132842 | A1 | 9/2002 | Hofmeister et al. |
| 2002/0137774 | A1 | 9/2002 | Riedl et al. |
| 2003/0055057 | A1 | 3/2003 | Blume et al. |
| 2003/0078274 | A1 | 4/2003 | Lipton |
| 2003/0119868 | A1 | 6/2003 | Grillot et al. |
| 2003/0144286 | A1 | 7/2003 | Frenkel et al. |
| 2003/0175348 | A1 | 9/2003 | Kofler et al. |
| 2003/0191170 | A1 | 10/2003 | Hofmeister et al. |
| 2003/0199562 | A1 | 10/2003 | Malamas et al. |
| 2004/0087626 | A1 | 5/2004 | Renhowe et al. |
| 2004/0087637 | A1 | 5/2004 | Zhou et al. |
| 2004/0106608 | A1 | 6/2004 | Munchhof et al. |
| 2004/0116387 | A1 | 6/2004 | Malm et al. |
| 2004/0122237 | A1 | 6/2004 | Amiri et al. |
| 2004/0127527 | A1 | 7/2004 | Hongu et al. |
| 2004/0209892 | A1 | 10/2004 | Di Pietro et al. |
| 2005/0038022 | A1 | 2/2005 | Morris et al. |
| 2005/0054705 | A1 | 3/2005 | Heinelt et al. |
| 2005/0136065 | A1 | 6/2005 | Valiante, Jr. |
| 2005/0192287 | A1 | 9/2005 | Costales et al. |
| 2005/0245547 | A1 | 11/2005 | Kim et al. |

FOREIGN PATENT DOCUMENTS

| | | |
|---|---|---|
| AU | 777275 | 10/2004 |
| EP | 0 604 181 | 6/1994 |
| EP | 0 618 221 | 10/1994 |
| EP | 0639573 A1 | 2/1995 |
| EP | 0 675 112 | 10/1995 |
| EP | 0 696 593 | 2/1996 |
| EP | 0 701 907 | 3/1996 |
| EP | 1183254 | 1/2005 |
| JP | 2001-322903 | 11/2001 |
| JP | 2002-141067 | 5/2002 |
| JP | 2003-246704 | 9/2003 |
| WO | WO 84/02131 | 6/1984 |
| WO | WO 94/15932 | 7/1994 |
| WO | WO 94/19357 | 9/1994 |
| WO | WO 95/08542 | 3/1995 |
| WO | WO 95/10514 | 4/1995 |
| WO | WO 95/10515 | 4/1995 |
| WO | WO 95/10516 | 4/1995 |
| WO | WO 95/11917 | 5/1995 |
| WO | WO 95/12572 | 5/1995 |
| WO | WO 95/12612 | 5/1995 |
| WO | WO 95/25086 | 9/1995 |
| WO | WO 95/32987 | 12/1995 |
| WO | WO 95/34535 | 12/1995 |
| WO | WO 96/00736 | 1/1996 |
| WO | WO 96/05168 | 2/1996 |
| WO | WO 96/05169 | 2/1996 |
| WO | WO 96/05529 | 2/1996 |
| WO | WO 96/06138 | 2/1996 |
| WO | WO 96/06193 | 2/1996 |
| WO | WO 96/16443 | 5/1996 |
| WO | WO 96/17861 | 6/1996 |
| WO | WO 96/21456 | 7/1996 |
| WO | WO 96/21701 | 7/1996 |
| WO | WO 96/22278 | 7/1996 |
| WO | WO 96/24611 | 8/1996 |
| WO | WO 96/24612 | 8/1996 |
| WO | WO 96/30017 | 10/1996 |
| WO | WO 96/30018 | 10/1996 |
| WO | WO 96/30343 | 10/1996 |
| WO | WO 96/30362 | 10/1996 |
| WO | WO 96/30363 | 10/1996 |
| WO | WO 96/31111 | 10/1996 |
| WO | WO 96/31477 | 10/1996 |
| WO | WO 96/31478 | 10/1996 |
| WO | WO 96/31501 | 10/1996 |
| WO | WO 96/33159 | 10/1996 |
| WO | WO 96/34850 | 11/1996 |
| WO | WO 96/34851 | 11/1996 |
| WO | WO 97/00252 | 1/1997 |
| WO | WO 97/02920 | 1/1997 |
| WO | WO 97/03047 | 1/1997 |
| WO | WO 97/03050 | 1/1997 |
| WO | WO 97/03069 | 1/1997 |
| WO | WO 97/04785 | 2/1997 |
| WO | WO 97/12613 | 4/1997 |
| WO | WO 97/17070 | 5/1997 |
| WO | WO 97/18813 | 5/1997 |
| WO | WO 97/21701 | 6/1997 |
| WO | WO 97/23478 | 7/1997 |
| WO | WO 97/26246 | 7/1997 |
| WO | WO 97/30053 | 8/1997 |
| WO | WO 97/38665 | 10/1997 |
| WO | WO 97/44350 | 11/1997 |
| WO | WO 98/02436 | 1/1998 |
| WO | WO 98/02438 | 1/1998 |
| WO | WO 98/28980 | 7/1998 |
| WO | WO 98/29119 | 7/1998 |

| | | |
|---|---|---|
| WO | WO 00/29404 | 5/2000 |
| WO | WO 00/35917 | 6/2000 |
| WO | WO 00/44777 | 8/2000 |
| WO | WO 00/50032 | 8/2000 |
| WO | WO 00/61186 | 10/2000 |
| WO | WO 00/61580 | 10/2000 |
| WO | WO 01/01986 A1 | 1/2001 |
| WO | WO 01/30768 | 5/2001 |
| WO | WO 01/66539 A1 | 9/2001 |
| WO | WO 01/72708 A2 | 10/2001 |
| WO | WO 01/72712 A1 | 10/2001 |
| WO | WO 01/98278 | 12/2001 |
| WO | WO 02/083064 | 10/2002 |
| WO | WO 02/083111 A2 | 10/2002 |
| WO | WO 02/083138 | 10/2002 |
| WO | WO 02/083139 | 10/2002 |
| WO | WO 02/083140 | 10/2002 |
| WO | WO 03/013526 | 2/2003 |
| WO | WO 03/024899 A2 | 3/2003 |
| WO | WO 03/039460 | 5/2003 |
| WO | WO 03/042184 A1 | 5/2003 |
| WO | WO 03/043985 A1 | 5/2003 |
| WO | WO 03/049527 | 6/2003 |
| WO | WO 03/049678 | 6/2003 |
| WO | WO 03/049679 | 6/2003 |
| WO | WO 03/050064 | 6/2003 |
| WO | WO 03/050122 | 6/2003 |
| WO | WO 03/079973 | 10/2003 |
| WO | WO 03/082272 | 10/2003 |
| WO | WO 03/087089 | 10/2003 |
| WO | WO 03/091245 A1 | 11/2003 |
| WO | WO 03/099211 | 12/2003 |
| WO | WO 03/105855 | 12/2003 |
| WO | WO 03/106417 | 12/2003 |
| WO | WO 2004/014881 A2 | 2/2004 |
| WO | WO 2004/035056 A1 | 4/2004 |
| WO | WO 2004/035740 A2 | 4/2004 |
| WO | WO 2004/039774 | 5/2004 |
| WO | WO 2004/085425 | 10/2004 |
| WO | WO 2004/085425 A1 | 10/2004 |
| WO | WO 2004/087153 | 10/2004 |
| WO | WO 2004/087153 A2 | 10/2004 |
| WO | WO 2004/103995 A1 | 12/2004 |
| WO | WO 2005/000404 A2 | 1/2005 |
| WO | WO 2005/005421 A1 | 1/2005 |
| WO | WO 2005/016914 A1 | 2/2005 |
| WO | WO 2005/030140 A2 | 4/2005 |
| WO | WO 2005/032548 | 4/2005 |
| WO | WO 2005/032548 A1 | 4/2005 |
| WO | WO 2005/037273 | 4/2005 |
| WO | WO 2005/037273 A1 | 4/2005 |
| WO | WO 2005/070920 | 8/2005 |
| WO | WO 2005/073224 A2 | 8/2005 |

OTHER PUBLICATIONS

U.S. Appl. No. 60/349,925, filed Jan. 18, 2002, Barrow et al.
U.S. Appl. No. 60/712,539, filed Aug. 30, 2005, Payman et al.
U.S. Appl. No. 60/713,108, filed Aug. 30, 2005, Novartis AG.
U.S. Appl. No. 60/731,591, filed Oct. 27, 2005, Darrin et al.
U.S. Appl. No. 60/774,684, filed Feb. 17, 2006, Darrin et al.
U.S. Appl. No. 60/832,715, filed Jul. 21, 2006, Ahmad et al.
"Sex, genes and women's health.", *Nature Genetics* 25: 1-2, 2002.
"Tumor angiogenesis—new drugs on the block." *Nature Biotechnology*, 17:963-968 (Oct. 1999).
Aprelikova, O. et al., "FLT4, a Novel Class III Receptor Tyrosine Kinase in Chromosome 5q33-qter." *Cancer Res.* 52:746-748 (1992).
Avruch, J. et al. "Raf meets Ras: completing the framework of a signal transduction pathway." *Trends Biochem. Sci.* 19(7):279-83 (1994).
Bagshawe K., "Antibody-Directed Enzyme Prodrug Therapy: A Review." *Drug Dev. Res.* 34:220-230 (1995).

Ben-AV et al., "Induction of vascular endothelial growth factor expression in synovial fibroblasts by prostaglandin E and interleukin-1: a potential mechanism of inflammatory angiogenesis." *FEBS Letters* 372:83-87 (1995).
Benezra, D. et al., "In Vivo Angiogenic Activity of Interleukins." *Arch. Ophthalmol.* 108:573-576 (1990).
Bergsagel, P. et al., "Promiscuous translocations into immunoglobulin heavy chain switch regions in multiple myeloma." *Proc. Nat. Acad. Sci.* 93:13931-13936 (1996).
Bertolini, G. et al. "A new rational hypothesis for the pharmacophore of the active metabolite of leflunomide, a potent immunosuppressive drug." *J. Med. Chem.* 40(13):2011-6 (1997).
Bodor, N., "Novel Approaches to the Design of Safer Drugs: Soft Drugs and Site-Specific Chemical Delivery Systems." *Advances in Drug Res.* 13:254-331 (1984).
Bos. "ras Oncogenes in Human Cancer: A Review." *Cancer Res.* 49, 4682-9 (1989).
Bouma, B. et al., "Thrombin-activatable fibrinolysis inhibitor (TAFI, plasma procarboxypeptidase B, Procarboxypeptidase R, procarboxypeptidase U)." *Thrombosis Res.* 101:329-354 (2001).
Brose, M. S. et al. "BRAF and RAS Mutations in Human Lung Cancer and Melanoma." *Cancer Res.* 62 6997-7000 (2002).
Cappellen, D. et al., "Frequent activating mutations of FGFR3 in human bladder and cervix carcinomas." (Letter) *Nature Genet.* 23:18-20 (1999).
Chakraborty, I. "Developmental expression of the cyclo-oxygenase-1 and cyclo-oxygenase-2 genes in the peri-implantation mouse uterus and their differential regulation by the blastocyst and ovarian steroids." *J. Mol. Endocrinol.* 16:107-122 (1996).
Chemical Abstracts Index Guide-Appendix IV (1987) paragraph 203.
Chesi, M. et al. "Frequent translocation t(4;14)(p16.3;q32.3) in multiple myeloma is associated with increased expression and activating mutations of fibroblast growth factor receptor 3." (*Nature Genet.* 16:260-264, (1997).
Chiarugi, V. et al., "Cox-2, iNOS and p53 as play-makers of tumor angiogenesis (Review)." *Intl. J. Mol. Med.* 2:715-719 (1998).
Cho et al., "Defective lysosomal targeting of activated fibroblast growth factor receptor 3 in achondroplasia." *Proc. Nat. Acad. Sci.* 101:609-614 (2004).
Connolly, D. et al., "Human Vascular Permeability Factor." *J. Biol. Chem.* 264(33):20017-20024, (1989).
Connolly, D. et al., "Tumor Vascular Permeability Factor Stimulates Endothelial Cell Growth and Angiogenesis." *J. Clin. Invest.* 84:1470-1478 (1989).
Crews, C. M. et al. "Extracellular Signals and Reversible Protein Phosphorylation: What to Mek of it All." *Cell*, 74, 215-17 (1993).
Crump, M. "Inhibition of raf kinase in the treatment of acute myeloid leukemia." *Curr. Pharm. Des.* 8:2243-2248 (2002).
Daum, G. et al., "The ins and outs of Raf kinases." *Trends Biochem. Sci*, 19:474-80 (1994).
Davies, H. et al. "Mutations of the BRAF gene in human cancer." *Nature* 417(6892):949-54 (2002).
Devries, C. et al., *Science* 255:989-991 (1992).
Diaz-Flores, L., "Intense Vascular Sprouting From Rat Femoral Vein Induced by Prostaglandins E1 and E2." *Anat. Rec.*, (238):68-76 (1994).
Dionne, C. et al., "BEK, a receptor for multiple members of the fibroblast growth factor (FGF) family, maps to human chromosome 10q25.3→q26." *Cytogenet. Cell Genet.* 60:34-36 (1992).
Donovan et al., "Constitutive MEK/MAPK activation leads to p27$^{Kip1}$ deregulation and antiestrogen resistance in human breast cancer cells." *J. Biol. Chem.* 276:40888-40895 (2001).
Fernandez et al., "Angotensin II and neovascularization." *J. Lab. Clin. Med.* 105:142-143 (1985).
Ferrara, N. et al., "The Biology of Vascular Endothelial Growth Factor." *Endocrinol. Rev.* 18:4-25 (1997).
Fridman, M. et al., "The minimal fragments of c-Raf-1 and NF1 that can suppress v-Ha-Ras-Induced malignant phenotype." *J. Biol. Chem.*, 269:30105-8 (1994).
Gu, W. et al., "Effect of Novel CAAX Peptidomimetic Farnesyltransferase Inhibitor on Angiogenesis In Vitro and In Vivo." *European J. of Cancer* 35(9):1394-1401 (1999).

Harada, S. et al., "Expression and Regulation of Vascular Endothelial Growth Factor in Osteoblasts." *Clin, Orthop.* 313, 76-80 (1995).

Heinrich, M. C. et al., "Inhibition of KIT tyrosine kinase activity: A novel molecular approach to the treatment of KIT-Positive malignancies." *J. Clin. Onc.* 20, 6 1692-1703 (2002).

Hla, T. et al. "Human cyclooxygenase-2 cDNA." *PNAS* 89 :7384-7399 (1992).

Hoshino, R. et al. "Constitutive activation of the 41-/43-kDa mitogen-activated protein kinase signaling pathway in human tumors." *Oncogene* 18(3):813-22 (1999).

Hotte, S. et. al., "BAY 43-9006: Early clinical data in patients with advanced solid malignancies." *Current Pharmaceutical Design* 8: 2249-2253, 2002.

IUPAC 1974 Recommendations for Section E, Fundamental Stereochemistry, *Pure Appl. Chem.* 45 :13-30 (1976).

Jang et al., "Mutations in fibroblast growth factor receptor 2 and fibroblast growth factor receptor 3 genes associated with human gastric and colorectal cancers." *Cancer Res.* 61, 3541-3 (2001).

Keegan, K et al., "Isolation of an additional member of the fibroblast growth factor receptor family, FGFR-3." *Proc. Nat. Acad. Sci.* 88:1095-1099 (1991).

Kim, K. et al., Inhibition of vascular endothelial growth factor-induced angiogenesis suppresses tumor growth in vivo. *Nature*, 362:841-844 (1993).

Kolch, W. et al. "Raf-1 protein kinase is required for growth of induced NIH/3T3 cells." *Nature* 349:426-428 (1991).

Kolch, W., Biochem. J. 351: 289-305, 2000 "Meaningful relationships: the regulation of the Ras/Raf/MEK/ERK pathway by protein interactions." *Biochem. J.* 351(Pt 2):289-305 (2000).).

Korte, W. , "Changes of the Coagulation and Fibrinolysis System in Malignancy: Their possible Impact on Future Diagnostic and Therapeutic Procedures." *Clin. Chem. La. Med.* 38(8):679-692 (2000).

Leung, D. et al., "Vascular endothelial growth factor is a secreted angiogenic mitogen." *Science* 246:1306-1309 (1989).

Majima, M. "Significant roles of inducible cyclooxygenase (COX)-2 in angiogenesis in rat sponge implants." *Jpn. J. Pharmacol.* 75:105-114 (1997).

March, "*Advanced Organic Chemistry: Reactions, Mechanisms and Structures*", Fourth Edition, John Wiley & Sons, pp. 69-74 (1992).

Monia, B. P. et al. "Antitumor activity of a phosphorothioate antisense oligodeoxynucleotide targeted against C-*raf* kinase." *Nat. Med.* 2(6):668-75 (1996).

Mustonen, T. et al., " Endothelial receptor tyrosine kinases involved in angiogenesis." *J. Cell Biology*, 129(4):895-898 (1995).

Oh, S. H. et al. "Asymmetric synthesis of bicyclic β-lactones via the intramolecular, nucleophile-catalyzed aldol lactonization: improved efficiency and expanded scope." *J Org,. Chem.* 70(7):2835-8 (2005).

Partanen, J et al., "FGFR-4, a novel acidic fibroblast growth factor receptor with a distinct expression pattern." *EMBO J.* 10:1347-1354 (1991).

Plouet, J. et al., "Isolation and characterization of a newly identified endothelial cell mitogen produced by AtT-20 cells." *EMBO J* 8:(12) 3801-3806 (1989).

Prescott, D., *Methods in Cell Biology*, vol. XIV, Academic Press, New York, N.W., p. 33-71 et seq. (1976).

Pritchard, C. A. et al. "Conditionally oncogenic forms of the A-Raf and B-Raf protein kinases display different biological and biochemical properties in NIH 3T3 cells." *Mol. Cell. Biol.* 15(11):6430-42 (1995).

Quinn, T. et al., "Fetal liver kinase 1 is a receptor for vascular endothelial growth factor and is selectively expressed in vascular endothelium." *Proc. Natl. Acad. Sci.* 90:7533-7537 (1993).

Rasmussen, T. et al., "FGFR3 dysregulation in multiple myeloma: frequency and prognostic relevance." *Br. J. Haematol.* 117:626-628 (2002).

Rockwell, P. et al., "Role of Protein Tyrosine Kinase Receptors in Cancer: Possibilities for Therapeutic Intervention." *Mol. Cell Differ.* 3(4):315 (1995).

Ruta, M et al, "A novel protein tyrosine kinase gene whose expression is modulated during endothelial cell differentiation." *Oncogene* 3:9-15 (1988).

Sapi, E., "The role of CSF-1 in normal physiology of mammary gland and breast cancer: an update." *Exp. Biol. Med* 229:1-11 (2004).

Sawyer, J. S. et al. "Synthesis of Diaryl Ethers, Diaryl Thioethers, and Diarylamines Mediated by Potassium Flouride—Alumina and 18-Crown-6: Expansion of Scope and Utility." *J. Org. Chem.* 63(18):6338-43 (1998).

Seed, M. et al., "The Inhibition of colon-26 Adenocarcinoma Development and Angiogenesis by Topical Diclofenac in 2.5% Hyaluronan." *Cancer Res.* 57:1625-1629 (1997).

Shan, D. et al. "Prodrug strategies based on intramolecular cyclization reactions." *J. Pharm. Sci.* 86(7):765-7 (1997).

Shibuya, M. et al. "Nucleotide sequence and expression of a novel human receptor-type tyrosine kinase gene (*flt*) closely related to the *fms* family." *Oncogene*, 5:519-524 (1990).

Terman, B. et al., "Identification of a new endothelial cell growth factor receptor tyrosine kinase." *Oncogene* 6:1677-1683 (1991).

Tordeux, M. et al., "Reactions of Trifluoromethyl Bromide and Related Halides: Part 10. Perfluoroalkylation of Aromatic Compounds induced by Sulphur Dioxide Radical Anion Precursors." *J. Chem Soc. Perkin Trans* 1, 2293-2299 (1990).

Tsujii, M. et al., "Cyclooxygenase Regulates Angiogenesis Induced by Colon Cancer Cells." *Cell* 93:705-716 (1998).

Ullrich, A. et al., "Signal Transduction by Receptors with Tyrosine Kinase Activity.", *Cell*, 61 203-212 (1990).

Van Der Geer, P. et al. "Receptor Protein-Tyrosine Kinases and their Signal Transduction Pathways.", *Annu. Rev. Cell Biol.*, 10:251-337,(1994).

Veikkola et al., "Regulation of angiogenesis via vascular endothelial growth factor receptors." *Cancer Res* 60:203-212 (2000).

Weber, C. K. et al. "Mitogenic signaling of Ras is regulated by differential interaction with Raf isozymes." *Oncogene* 19(2):169-76 (2000).

Wey S. et al., "Vascular Endothelial Growth Factor Receptors: Expression and Function in Solid Tumors.", *Clinical Advances in Hematology and Oncology*, 2:37-45 (2004).

Xin, X. " Peroxisome Proliferator-activated Receptor γ Ligands are potent inhibitors of angiogenesis in Vitro and in Vivo." *J. Biol. Chem.* 274(13):9116-9121 (1999).

Yalpani, M., "Cholesterol Lowering Drugs.", *Chemistry & Industry*, pp. 85-89 (Feb. 5, 1996).

Yuen, S. T. et al. "Similarity of the Phenotypic Patterns Associated with BRAF and KRAS Mutations in Colorectal Neoplasia." *Cancer Res.* 62(22):6451-55 (2002).

Zacharski, L. et al., "Heparin and cancer." *Thromb. Haemost.* 80:10-23 (1998).

Ziche, M. "Role of prostaglandin $E_1$ and copper in angiogenesis." *JNCI* 69:475-482 (1982).

\* cited by examiner

SUBSTITUTED BENZIMIDAZOLES AND METHODS OF PREPARATION

CROSS REFERENCE TO RELATED APPLICATION

This application is a continuation of U.S. Ser. No. 11/513,745, filed Aug. 30, 2006, now abandoned, which in turn claims priority under 35 U.S.C. §119(e) to provisional applications U.S. Ser. No. 60/713,108 filed on Aug. 30, 2005, U.S. Ser. No. 60/712,539 filed on Aug. 30, 2005, U.S. Ser. No. 60/731,591 filed on Oct. 27, 2005, and U.S. Ser. No. 60/774,684 filed on Feb. 17, 2006, each of which is incorporated herein by reference in its entirety.

FIELD OF THE INVENTION

The present invention relates to methods for preparing novel substituted benzimidazole compounds, their tautomers, stereoisomers, esters, metabolites, prodrugs, or pharmaceutically acceptable salts thereof for use in the prophylaxis or treatment of cancer.

BACKGROUND OF THE INVENTION

The Raf serine/threonine kinases are essential components of the Ras/Mitogen-Activated Protein Kinase (MAPK) signaling module that controls a complex transcriptional program in response to external cellular stimuli. Raf genes code for highly conserved serine-threonine-specific protein kinases which are known to bind to the ras oncogene. They are part of a signal transduction pathway believed to consist of receptor tyrosine kinases, p21 ras, Raf protein kinases, Mek1 (ERK activator or MAPKK) kinases and ERK (MAPK) kinases, which ultimately phosphorylate transcription factors. In this pathway Raf kinases are activated by Ras and phosphorylate and activate two isoforms of Mitogen-Activated Protein Kinase Kinase (called Mek1 and Mek2), that are dual specificity threonine/tyrosine kinases. Both Mek isoforms activate Mitogen Activated Kinases 1 and 2 (MAPK, also called Extracellular Ligand Regulated Kinase 1 and 2 or Erk1 and Erk2). The MAPKs phosphorylate many substrates including transcription factors and in so doing set up their transcriptional program. Raf kinase participation in the Ras/MAPK pathway influences and regulates many cellular functions such as proliferation, differentiation, survival, oncogenic transformation and apoptosis.

Both the essential role and the position of Raf in many signaling pathways have been demonstrated from studies using deregulated and dominant inhibitory Raf mutants in mammalian cells as well as from studies employing biochemical and genetic techniques of model organisms. In many cases, the activation of Raf by receptors that stimulate cellular tyrosine phosphorylation is dependent on the activity of Ras, indicating that Ras functions upstream of Raf. Upon activation, Raf-1 then phosphorylates and activates Mek1, resulting in the propagation of the signal to downstream effectors, such as MAPK (mitogen-activated protein kinase) (Crews et al. (1993) *Cell* 74:215). The Raf serine/threonine kinases are considered to be the primary Ras effectors involved in the proliferation of animal cells (Avruch et al. (1994) *Trends Biochem. Sci.* 19:279).

Raf kinase has three distinct isoforms, Raf-1 (c-Raf), A-Raf, and B-Raf, distinguished by their ability to interact with Ras, to activate MAPK kinase pathway, tissue distribution and sub-cellular localization (Marias et. al., *Biochem. J.* 351: 289-305, 2000; Weber et. al., *Oncogene* 19:169-176, 2000; Pritchard et. al., *Mol. Cell. Biol.* 15:6430-6442, 1995). Raf kinases are activated by Ras and phosphorylate and activate two isoforms of Mitogen-Activated Protein Kinase Kinase (called Mek1 and Mek2), that are dual specificity threonine/tyrosine kinases. Both Mek isoforms activate Mitogen Activated Kinases 1 and 2 (MAPK, also called Extracellular Ligand Regulated Kinase 1 and 2 or Erk1 and Erk2). The MAPKs phosphorylate many substrates including cytosolic proteins and ETS family of transcription factors. Raf kinase participation in the Ras/MAPK pathway influences and regulates many cellular functions such as proliferation, differentiation, survival, cell cycle progression and apoptosis.

Activating mutation of one of the Ras genes can be seen in about 20% of all tumors and the Raf/MEK/ERK pathway is activated in about 30% of all tumors (Bos et. al., *Cancer Res.* 49:4682-4689, 1989; Hoshino et. al., *Oncogene* 18:813-822, 1999). Recent studies have shown that B-Raf mutation in the skin nevi is a critical step in the initiation of melanocytic neoplasia (Pollock et. al., *Nature Genetics* 25: 1-2, 2002). Furthermore, recent studies have disclosed that activating mutation in the kinase domain of B-Raf occurs in about 66% of melanomas, 12% of colon carcinoma and 14% of liver cancer (Davies et. al., *Nature* 417:949-954, 2002) (Yuen et. al., *Cancer Research* 62:6451-6455, 2002) (Brose et. al., *Cancer Research* 62:6997-7000, 2002).

Inhibitors of Raf/MEK/ERK pathway at the level of Raf kinases can potentially be effective as therapeutic agents against tumors with over-expressed or mutated receptor tyrosine kinases, activated intracellular tyrosine kinases, tumors with aberrantly expressed Grb2 (an adapter protein that allows stimulation of Ras by the Sos exchange factor) as well as tumors harboring activating mutations of Raf itself. In the early clinical trials an inhibitor of Raf-1 kinase that also inhibit B-Raf have shown promise as therapeutic agents in cancer therapy (Crump, *Current Pharmaceutical Design* 8:2243-2248, 2002; Sebastien et. al., *Current Pharmaceutical Design* 8: 2249-2253, 2002).

Disruption of Raf expression in cell lines through the application of RNA antisense technology has been shown to suppress both Ras and Raf-mediated tumorigenicity (Kolch et al., *Nature* 349:416-428, 1991; Monia et al., *Nature Medicine* 2(6):668-675, 1996).

Several Raf kinase inhibitors have been described as exhibiting efficacy in inhibiting tumor cell proliferation in vitro and/or in vivo assays (see, e.g., U.S. Pat. Nos. 6,391,636, 6,358,932, 6,037,136, 5,717,100, 6,458,813, 6,204,467, and 6,268,391). Other patents and patent applications suggest the use of Raf kinase inhibitors for treating leukemia (see, e.g., U.S. Pat. Nos. 6,268,391, and 6,204,467, and published U.S. Patent Application Nos. 20020137774; 20020082192; 20010016194; and 20010006975), or for treating breast cancer (see, e.g., U.S. Pat. Nos. 6,358,932, 5,717,100, 6,458,813, 6,268,391, and 6,204,467, and published U.S. Patent Application No. 20010014679).

U.S. provisional application Ser. No. 60/713,108 filed on Aug. 30, 2005, Ser. No. 60/712,539 filed on Aug. 30, 2005, Ser. No. 60/731,591 filed on Oct. 27, 2005, and Ser. No. 60/774,684 filed on Feb. 17, 2006, disclose substituted benzimidazole compounds, their methods of synthesis, and uses. The compounds described therein are potent kinase inhibitors and are useful for treating proliferative diseases mediated by kinases such as Raf kinase.

SUMMARY OF THE INVENTION

The present invention provides improved methods and related intermediates for preparing substituted benzimidazole compounds, their tautomers, stereoisomers, esters, metabolites, prodrugs, or pharmaceutically acceptable salts thereof having Formula (I):

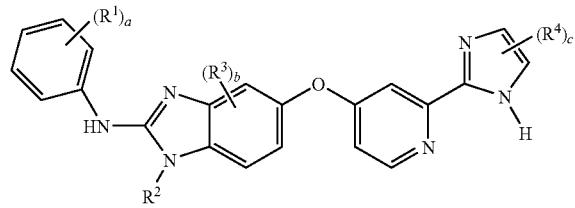

wherein, each $R^1$ is independently selected from hydroxy, halo, $C_{1-6}$ alkyl, $C_{1-6}$ alkoxy, ($C_{1-6}$ alkyl)sulfanyl, ($C_{1-6}$ alkyl)sulfonyl, cycloalkyl, heterocycloalkyl, phenyl, and heteroaryl;

$R^2$ is $C_{1-6}$ alkyl or halo($C_{1-6}$ alkyl);

each $R^3$ is independently selected from halo, $C_{1-6}$ alkyl, and $C_{1-6}$ alkoxy;

each $R^4$ is independently selected from hydroxy, $C_{1-6}$ alkyl, $C_{1-6}$ alkoxy, halo, heterocycloalkylcarbonyl, carboxyl, ($C_{1-6}$ alkoxy)carbonyl, aminocarbonyl, $C_{1-6}$ alkylaminocarbonyl, carbonitrile, cycloalkyl, heterocycloalkyl, phenyl, and heteroaryl;

wherein $R^1$, $R^2$, $R^3$, and $R^4$ may be optionally substituted with one or more substituents independently selected from hydroxy, halo, $C_{1-6}$ alkyl, halo($C_{1-6}$ alkyl), $C_{1-6}$ alkoxy, and halo($C_{1-6}$ alkoxy);

a is 1, 2, 3, 4, or 5;

b is 0, 1, 2, or 3; and c is 1 or 2.

DETAILED DESCRIPTION OF THE PREFERRED EMBODIMENT

In accordance with one aspect of the present invention, provided is a method for preparing a compound of Formula (I) or a tautomer, stereoisomer, ester, metabolite, prodrug, or pharmaceutically acceptable salt thereof

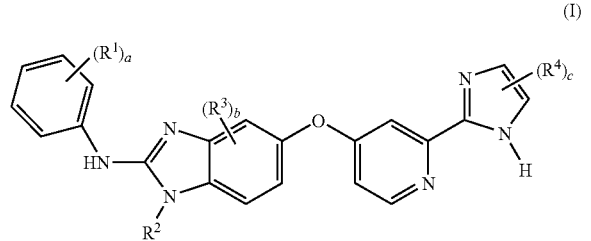

wherein, each $R^1$ is independently selected from hydroxy, halo, $C_{1-6}$ alkyl, $C_{1-6}$ alkoxy, ($C_{1-6}$ alkyl)sulfanyl, ($C_{1-6}$ alkyl)sulfonyl, cycloalkyl, heterocycloalkyl, phenyl, and heteroaryl;

$R^2$ is $C_{1-6}$ alkyl or halo($C_{1-6}$ alkyl);

each $R^3$ is independently selected from halo, $C_{1-6}$ alkyl, and $C_{1-6}$ alkoxy;

each $R^4$ is independently selected from hydroxy, $C_{1-6}$ alkyl, $C_{1-6}$ alkoxy, halo, heterocycloalkylcarbonyl, carboxyl, ($C_{1-6}$ alkoxy)carbonyl, aminocarbonyl, $C_{1-6}$ alkylaminocarbonyl, carbonitrile, cycloalkyl, heterocycloalkyl, phenyl, and heteroaryl;

wherein $R^1$, $R^2$, $R^3$, and $R^4$ may be optionally substituted with one or more substituents independently selected from hydroxy, halo, $C_{1-6}$ alkyl, halo($C_{1-6}$ alkyl), $C_{1-6}$ alkoxy, and halo($C_{1-6}$ alkoxy);

a is 1, 2, 3, 4, or 5;

b is 0, 1, 2, or 3; and c is 1 or 2;

the method comprising:

(a) reacting a compound of Formula (II) with a compound of Formula (III) to provide a compound of Formula (IV)

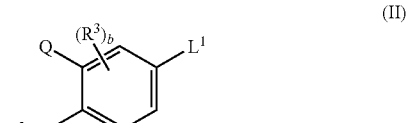

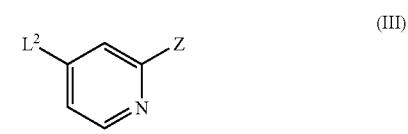

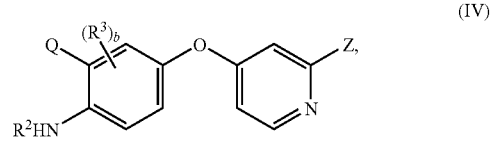

wherein Q is $NH_2$ or $NO_2$; one of $L^1$ or $L^2$ is halo and the other of $L^1$ or $L^2$ is OH or an anion thereof, Z is cyano, $COOR^5$, $CH_2OR^5$, CHO, or imidazol-2-yl substituted with one or two $R^4$ groups and wherein $R^5$ is hydrogen or a hydroxy protecting group;

(b) when in the compound of Formula (IV) Z is $COOR^5$ or $CH_2OR^5$, converting said compound to a compound of Formula (IV) wherein Z is CHO;

(c) when in the compound of Formula (IV) Z is cyano, converting the cyano functionality to an amidino functionality and reacting said amidino functionality with a compound of Formula (Va) under imidazole ring forming conditions to provide a compound of Formula (VI); or when in the compound of Formula (IV) Z is CHO, reacting said compound with a compound of Formula (Vb) to provide a compound of Formula (VI)

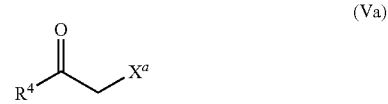

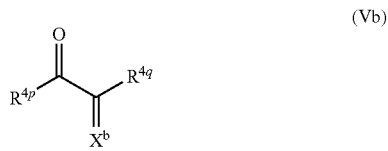

-continued

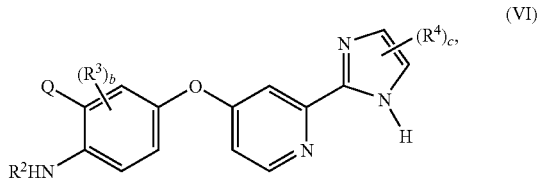
(VI)

wherein $X^a$ in Formula (Va) is a leaving group and $R^{4p}$ and $R^{4q}$ in Formula (Vb) are independently H or $R^4$, provided that at least one of $R^{4p}$ and $R^{4q}$ is $R^4$ and $X^b$ is =O or =NHOH and provided that c is 1 when a compound of Formula (VI) is prepared from a compound of Formula (Va);

(d) when in the compound of Formula (VI) Q is $NO_2$, converting said compound to a compound of Formula (VI) wherein Q is $NH_2$;

(e) reacting the compound of Formula (VI) wherein Q is $NH_2$ with a compound of Formula (VII) to provide a compound of Formula (VIII) or a tautomer thereof

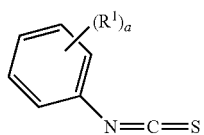
(VII)

(VIII)

(f) reacting the compound of Formula (VIII) or a tautomer thereof with a desulfurizing agent to provide a compound of Formula (I);

(g) optionally reacting the compound of Formula (I) or a tautomer thereof with an acid to give a first pharmaceutically acceptable salt;

(h) optionally converting the first pharmaceutically acceptable salt of a compound of Formula (I) or a tautomer thereof to a second pharmaceutically acceptable salt; and (i) optionally converting a compound of Formula (I) or a tautomer or pharmaceutically acceptable salt thereof to an ester, metabolite, or prodrug of Formula (I).

In some embodiments, part (a) is carried out with organic or inorganic base in polar solvent. Suitable inorganic bases include NaOH, KOH, $CaCO_3$, and $K_2CO_3$. Suitable polar solvents include dimethylsulfoxide and dimethylformamide.

In some embodiments, part (b) comprises reacting a compound of Formula (IV) when Z is $COOR^5$ with a reducing agent. In some aspects, $R^5$ is tert-butyl. In other aspects, the reducing agent is diisobutylaluminum hydride.

In some embodiments, the leaving group $X^a$ in the compound of Formula (Va) is halogen. In another embodiment, $X^a$ is $-SO_2R^{10}$ where $R^{10}$ is $C_{1-6}$ alkyl or phenyl, wherein $C_{1-6}$ alkyl or phenyl are optionally substituted with one to three halo, $C_{1-6}$ alkoxy, or $C_{1-6}$ alkyl groups. In some aspects, $R^{10}$ is methyl or trifluoromethyl.

In one embodiment, the compound of Formula (Va) is 3-bromo-1,1,1-trifluoroacetone (i.e. $X^a$ is Br and $R^4$ is $CF_3$).

In one embodiment, the amidino functionality of part (c) is formed by treating the compound of Formula (IV) wherein Z is cyano with an alkoxide and an ammonium reagent. In one aspect, the alkoxide is sodium methoxide. In other aspects, the ammonium reagent is ammonium acetate. In another aspect, the ammonium reagent is ammonium benzoate.

In one embodiment, the imidazole ring forming conditions of part (c) comprises exposing the reaction product formed from the reaction of the amidino functionality with a compound of Formula (Va) to an acid. In one aspect, the acid is an organic acid. Suitable organic acids include acetic acid, methanesulfonic acid, camphorsulfonic acid, trifluoromethanesulfonic acid, and trifluoroacetic acid. In another aspect, the acid is an inorganic acid such as hydrochloric acid and sulfuric acid.

In one embodiment, the imidazole ring forming conditions of part (c) comprises heating the reaction product formed from the reaction of the amidino functionality with a compound of Formula (Va). In some aspects, the heating is carried out in an alcoholic solvent. Suitable alcoholic solvents include 1-propanol. In some embodiments, the heating is carried out at a temperature of about 80° C. to 100° C. In other embodiments the heating is carried out at about 85° C.

In some embodiments, part (c) when in the compound of Formula (IV) Z is CHO is carried out with $NH_4OH$ in polar solvent. In some aspects, the polar solvent is a mixture of ethyl acetate and ethanol.

In some embodiments, part (d) comprises reacting a compound of Formula (VI) when Q is $NO_2$ with a reducing agent. In some aspects, the reducing agent is sodium dithionite.

In some embodiments, part (e) is carried out in acetonitrile.

In some embodiments, the desulfurizing agent in part (f) is selected from the group consisting of $FeCl_3$, 2-chloro-1-methylpyridinium iodide, 2-chloro-1,3-dimethylimidazolium chloride, and $POCl_3$.

In another embodiment, provided is a method for preparing a pharmaceutically acceptable salt of a compound of Formula (I) or tautomer thereof (I)

wherein, each $R^1$ is independently selected from hydroxy, halo, $C_{1-6}$ alkyl, $C_{1-6}$ alkoxy, ($C_{1-6}$ alkyl)sulfanyl, ($C_{1-6}$ alkyl)sulfonyl, cycloalkyl, heterocycloalkyl, phenyl, and heteroaryl;

$R^2$ is $C_{1-6}$ alkyl or halo($C_{1-6}$ alkyl);

each $R^3$ is independently selected from halo, $C_{1-6}$ alkyl, and $C_{1-6}$ alkoxy;

each $R^4$ is independently selected from hydroxy, $C_{1-6}$ alkyl, $C_{1-6}$ alkoxy, halo, heterocycloalkylcarbonyl, carboxyl, ($C_{1-6}$ alkoxy)carbonyl, aminocarbonyl, $C_{1-6}$ alkylaminocarbonyl, carbonitrile, cycloalkyl, heterocycloalkyl, phenyl, and heteroaryl;

wherein $R^1$, $R^2$, $R^3$, and $R^4$ may be optionally substituted with one or more substituents independently selected from hydroxy, halo, $C_{1-6}$ alkyl, halo($C_{1-6}$ alkyl), $C_{1-6}$ alkoxy, and halo($C_{1-6}$ alkoxy);

a is 1, 2, 3, 4, or 5;
b is 0, 1, 2, or 3;
c is 1 or 2;
the method comprising:
(a) reacting a compound of Formula (I) or a tautomer thereof with an acid to give a first pharmaceutically acceptable salt; or
(b) converting the first pharmaceutically acceptable salt of a compound of Formula (I) or a tautomer thereof to a second pharmaceutically acceptable salt.

In one embodiment, provided is a method for preparing a compound of Formula (I) or a tautomer, stereoisomer, ester, metabolite, prodrug, or pharmaceutically acceptable salt, thereof

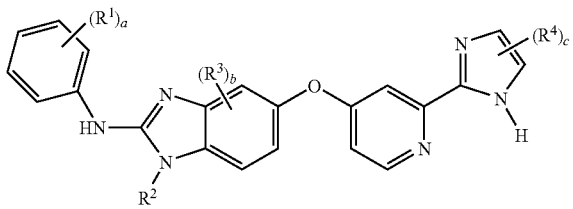

(I)

wherein,
each $R^1$ is independently selected from hydroxy, halo, $C_{1-6}$ alkyl, $C_{1-6}$ alkoxy, ($C_{1-6}$ alkyl)sulfanyl, ($C_{1-6}$ alkyl)sulfonyl, cycloalkyl, heterocycloalkyl, phenyl, and heteroaryl;

$R^2$ is $C_{1-6}$ alkyl or halo($C_{1-6}$ alkyl);

each $R^3$ is independently selected from halo, $C_{1-6}$ alkyl, and $C_{1-6}$ alkoxy;

each $R^4$ is independently selected from hydroxy, $C_{1-6}$ alkyl, $C_{1-6}$ alkoxy, halo, heterocycloalkylcarbonyl, carboxyl, ($C_{1-6}$ alkoxy)carbonyl, aminocarbonyl, $C_{1-6}$ alkylaminocarbonyl, carbonitrile, cycloalkyl, heterocycloalkyl, phenyl, and heteroaryl;

wherein $R^1$, $R^2$, $R^3$, and $R^4$ may be optionally substituted with one or more substituents independently selected from hydroxy, halo, $C_{1-6}$ alkyl, halo($C_{1-6}$ alkyl), $C_{1-6}$ alkoxy, and halo($C_{1-6}$ alkoxy);

a is 1, 2, 3, 4, or 5;
b is 0, 1, 2, or 3;
c is 1 or 2;
the method comprising:
reacting a compound of Formula (XIII) with a compound of Formula (XIV) to provide a compound of Formula (I)

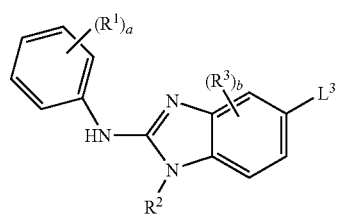

(XIII)

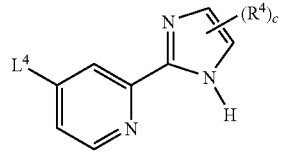

(XIV)

wherein one of $L^3$ or $L^4$ is halo and the other of $L^3$ or $L^4$ is OH or an anion thereof; or reacting a compound of Formula (XV) with a compound of Formula (Vb) to provide a compound of Formula (I)

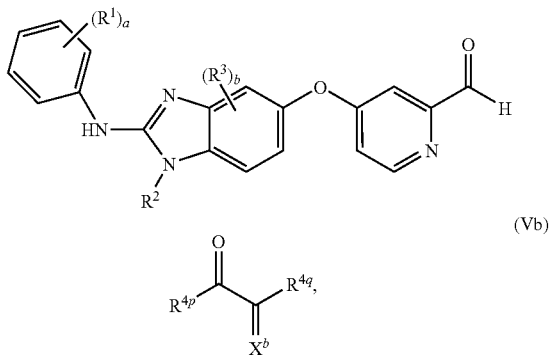

(XV)

(Vb)

wherein $R^{4p}$ and $R^{4q}$ are independently H or $R^4$, provided that at least one of $R^{4p}$ and $R^{4q}$ is $R^4$; and $X^b$ is =O or =NHOH; or reacting the compound of Formula (VIII) or a tautomer thereof with a desulfurizing agent to provide a compound of Formula (I)

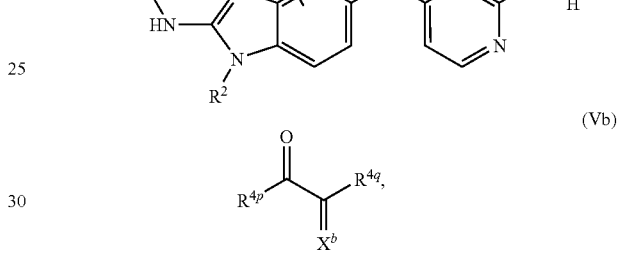

(VIII)

In one embodiment and in combination with any of the embodiments disclosed herein, provided is a tautomer of a compound of Formula (I).

In one embodiment and in combination with any of the embodiments disclosed herein, $R^2$ is $C_{1-6}$ alkyl. In some aspects, $R^2$ is methyl.

In one embodiment and in combination with any of the embodiments disclosed herein, $R^3$ is $C_{1-6}$ alkoxy. In some aspects, $R^3$ is methoxy.

In one embodiment and in combination with any of the embodiments disclosed herein, b is 0. In some aspects, a is 1 and c is 1.

In some embodiments, $R^1$, $R^2$, $R^3$, and $R^4$ may be optionally substituted with one to five substituents independently selected from hydroxy, halo, $C_{1-6}$ alkyl, halo($C_{1-6}$ alkyl), $C_{1-6}$ alkoxy, and halo($C_{1-6}$ alkoxy).

In some embodiments, $R^1$, $R^2$, $R^3$, and $R^4$ may be optionally substituted with one to three substituents independently selected from hydroxy, halo, $C_{1-6}$ alkyl, halo($C_{1-6}$ alkyl), $C_{1-6}$ alkoxy, and halo($C_{1-6}$ alkoxy).

In one embodiment and in combination with any of the embodiments disclosed herein, $R^1$ is independently selected from the group consisting of halo, $C_{1-6}$ alkoxy, halo($C_{1-6}$ alkyl), hydroxy, halo($C_{1-6}$ alkoxy), halo($C_{1-6}$ alkyl)sulfonyl, heteroaryl, halo($C_{1-6}$ alkyl)sulfanyl, heterocycloalkyl, and ($C_{1-6}$ alkyl)heterocycloalkyl.

In one embodiment and in combination with any of the embodiments disclosed herein, a is 1 and $R^1$ is independently selected from the group consisting of 2-chloro, 2-ethyl, 2-trifluoromethyl, 3-trifluoromethyl, 4-trifluoromethyl, 3-tert-butyl, 4-tert-butyl, 3-ethyl, 4-ethyl, 4-chloro, 4-bromo, 4-trifluoromethoxy, 4-trifluoromethylsulfanyl, 4-trifluoromethylsulfonyl, and 4-(4-methylpiperazinyl).

In one embodiment and in combination with any of the embodiments disclosed herein, a is 2 and each $R^1$ is independently selected from the group consisting of 2-fluoro, 2-chloro, 2-hydroxy, 2-methoxy, 3-methoxy, 5-methoxy, 4-chloro, 4-fluoro, 3-trifluoromethyl, 4-trifluoromethyl, 5-trifluoromethyl, 5-pyridinyl, 5-pyridinyl-3-yl, 5-pyridinyl-4-yl, 3-tetrahydrofuran-3-yl, 3-isopropyl, 5-isopropyl, and 5-tert-butyl.

In one embodiment and in combination with any of the embodiments disclosed herein, $R^4$ is selected from the group consisting of $C_{1-6}$ alkyl, hydroxy($C_{1-6}$ alkyl), halo($C_{1-6}$ alkyl), halo($C_{1-6}$ alkyl)sulfanyl, ($C_{1-6}$ alkoxy)carbonyl, ($C_{1-6}$ alkyl)heterocycloalkyl, carbonitrile, phenyl, halo($C_{1-6}$ alkyl)phenyl, ($C_{1-6}$ alkyl)heterocycloalkylcarbonyl, and hydroxy($C_{1-6}$ alkylaminocarbonyl). In some such embodiments, c is 1 and $R^4$ is selected from the group consisting of trifluoromethyl, carbonitrile, phenyl, trifluoromethylsulfanyl, methoxycarbonyl, 4-ethylpiperazinyl, 4-ethylpiperazinyl-1-carbonyl, or 2-hydroxyethylaminocarbonyl.

In other embodiments, $R^4$ is selected from the group consisting of $C_{1-6}$ alkyl, hydroxy($C_{1-6}$ alkyl), halo($C_{1-6}$ alkyl), ($C_{1-6}$ alkyl)heterocycloalkyl, phenyl, and halo($C_{1-6}$ alkyl)phenyl. In some such embodiments $R^4$ is selected from the group consisting of methyl, trifluoromethyl, and phenyl. In some such aspects, $R^4$ is trifluoromethyl.

In still other embodiments, c is 2 and each $R^4$ is independently selected from the group consisting of methyl, 3-trifluoromethylphenyl, 4-trifluoromethylphenyl, trifluoromethyl, ethoxycarbonyl, hydroxymethyl, and phenyl.

In one embodiment and in combination with any of the embodiments disclosed herein, Formula (I) is selected from the group consisting of {1-Methyl-5-[2-(5-trifluoromethyl-1H-imidazol-2-yl)-pyridin-4-yloxy]-1H-benzo-imidazol-2-yl}-(4-trifluoromethylphenyl)-amine, (2-Fluoro-5-pyridin-3-yl-phenyl)-{1-methyl-5-[2-(5-trifluoromethyl-1H-imidazol-2-yl)-pyridin-4-yloxy]-1H-benzoimidazol-2-yl}-amine, (2-Fluoro-5-pyridin-4-yl-phenyl)-{1-methyl-5-[2-(5-trifluoromethyl-1H-imidazol-2-yl)-pyridin-4-yloxy]-1H-benzoimidazol-2-yl}-amine, (4-tert-Butyl-phenyl)-{1-methyl-5-[2-(5-trifluoromethyl-1H-imidazol-2-yl)-pyridin-4-yl-oxy]-1H-benzoimidazol-2-yl}-amine, {1-Methyl-5-[2-(5-trifluoromethyl-1H-imidazol-2-yl)-pyridin-4-yloxy]-1H-benzo-imidazol-2-yl}-(3-trifluoromethyl-phenyl)-amine, (3-Ethyl-phenyl)-{1-methyl-5-[2-(5-trifluoromethyl-1H-imidazol-2-yl)-pyridin-4-yloxy]-1H-benzoimidazol-2-yl}-amine, (4-Chloro-phenyl)-{1-methyl-5-[2-(5-trifluoromethyl-1H-imidazol-2-yl)-pyridin-4-yl-oxy]-1H-benzoimidazol-2-yl}-amine, (4-Ethyl-phenyl)-{1-methyl-5-[2-(5-trifluoromethyl-1H-imidazol-2-yl)-pyridin-4-yloxy]-1H-benzoimidazol-2-yl}-amine, (4-Chloro-3-trifluoromethyl-phenyl)-{1-methyl-5-[2-(5-trifluoromethyl-1H-imidazol-2-yl)-pyridin-4-yloxy]-1H-benzoimidazol-2-yl}-amine, (4-Fluoro-3-trifluoromethyl-phenyl)-{1-methyl-5-[2-(5-trifluoromethyl-1H-imidazol-2-yl)-pyridin-4-yloxy]-1H-benzoimidazol-2-yl}-amine, {1-Methyl-5-[2-(5-trifluoromethyl-1H-imidazol-2-yl)-pyridin-4-yloxy]-1H-benzo-imidazol-2-yl}-(4-trifluoromethoxy-phenyl)-amine, (2-Fluoro-5-trifluoromethyl-phenyl)-(1-methyl-5-{2-[5-methyl-4-(3-trifluoromethyl-phenyl)-1H-imidazol-2-yl]-pyridin-4-yloxy}-1H-benzoimidazol-2-yl)-amine, (2-Fluoro-5-trifluoromethyl-phenyl)-(1-methyl-5-{2-[5-methyl-4-(4-trifluoromethyl-phenyl)-1H-imidazol-2-yl]-pyridin-4-yloxy}-1H-benzoimidazol-2-yl)-amine, 2-{4-[2-(2-Fluoro-5-trifluoromethyl-phenylamino)-1-methyl-1H-benzoimidazol-5-yl-oxy]-pyridin-2-yl}-5-trifluoromethyl-1H-imidazole-4-carboxylic acid ethyl ester, (2-{4-[2-(2-Fluoro-5-trifluoromethyl-phenylamino)-1-methyl-1H-benzoimidazol-5-yl-oxy]-pyridin-2-yl}-5-trifluoromethyl-1H-imidazol-4-yl)-methanol, 2-{4-[1-Methyl-2-(4-trifluoromethyl-phenylamino)-1H-benzoimidazol-5-yloxy]-pyridin-2-yl}-3H-imidazole-4-carbonitrile, (3-tert-Butyl-phenyl)-{1-methyl-5-[2-(5-phenyl-1H-imidazol-2-yl)-pyridin-4-yloxy]-1H-benzoimidazol-2-yl}-amine, {1-Methyl-5-[2-(5-phenyl-1H-imidazol-2-yl)-pyridin-4-yloxy]-1H-benzoimidazol-2-yl}-(4-trifluoromethylsulfanyl-phenyl)-amine, (3-tert-Butyl-phenyl)-{1-methyl-5-[2-(5-trifluoromethyl-1H-imidazol-2-yl)-pyridin-4-yl-oxy]-1H-benzoimidazol-2-yl}-amine,

[4-Fluoro-3-(tetrahydro-furan-3-yl)-phenyl]-{1-methyl-5-[2-(5-trifluoromethyl-1H-imidazol-2-yl)-pyridin-4-yloxy]-1H-benzoimidazol-2-yl}-amine, (4-Bromo-phenyl)-{1-methyl-5-[2-(5-trifluoromethyl-1H-imidazol-2-yl)-pyridin-4-yl-oxy]-1H-benzoimidazol-2-yl}-amine, (4-Fluoro-3-isopropyl-phenyl)-{1-methyl-5-[2-(5-trifluoromethyl-1H-imidazol-2-yl)-pyridin-4-yloxy]-1H-benzoimidazol-2-yl}-amine, {1-Methyl-5-[2-(5-trifluoromethyl-1H-imidazol-2-yl)-pyridin-4-yloxy]-1H-benzo-imidazol-2-yl}-(4-trifluoromethylsulfanyl-phenyl)-amine, (2-Fluoro-5-isopropyl-phenyl)-{1-methyl-5-[2-(5-trifluoromethyl-1H-imidazol-2-yl)-pyridin-4-yloxy]-1H-benzoimidazol-2-yl}-amine, (2-Fluoro-5-trifluoromethyl-phenyl)-{1-methyl-5-[2-(5-trifluoromethyl-1H-imidazol-2-yl)-pyridin-4-yloxy]-1H-benzoimidazol-2-yl}-amine, (5-tert-Butyl-2-fluoro-phenyl)-{1-methyl-5-[2-(5-trifluoromethyl-1H-imidazol-2-yl)-pyridin-4-yloxy]-1H-benzoimidazol-2-yl}-amine, (2-Fluoro-5-trifluoromethyl-phenyl)-{1-methyl-5-[2-(5-methyl-1H-imidazol-2-yl)-pyridin-4-yloxy]-1H-benzoimidazol-2-yl}-amine, (2-Fluoro-5-pyridin-3-yl-phenyl)-{1-methyl-5-[2-(5-trifluoromethyl-1H-imidazol-2-yl)-pyridin-4-yloxy]-1H-benzoimidazol-2-yl}-amine,
2-{4-[2-(2-Fluoro-5-trifluoromethyl-phenylamino)-1-methyl-1H-benzoimidazol-5-yl-oxy]-pyridin-2-yl}-3H-imidazole-4-carbonitrile,
(2-Chloro-4-trifluoromethyl-phenyl)-{1-methyl-5-[2-(5-trifluoromethyl-1H-imidazol-2-yl)-pyridin-4-yloxy]-1H-benzoimidazol-2-yl}-amine,
(5-tert-Butyl-2-chloro-phenyl)-{1-methyl-5-[2-(5-trifluoromethyl-1H-imidazol-2-yl)-pyridin-4-yloxy]-1H-benzoimidazol-2-yl}-amine,
(2-Fluoro-5-pyridin-4-yl-phenyl)-{1-methyl-5-[2-(5-trifluoromethyl-1H-imidazol-2-yl)-pyridin-4-yloxy]-1H-benzoimidazol-2-yl}-amine,
(2-Fluoro-5-trifluoromethyl-phenyl)-{1-methyl-5-[2-(4-phenyl-5-trifluoromethyl-1H-imidazol-2-yl)-pyridin-4-yloxy]-1H-benzoimidazol-2-yl}-amine,
(2-Chloro-5-trifluoromethyl-phenyl)-{1-methyl-5-[2-(4-phenyl-5-trifluoromethyl-1H-imidazol-2-yl)-pyridin-4-yloxy]-1H-benzoimidazol-2-yl}-amine,
{1-Methyl-5-[2-(4-phenyl-5-trifluoromethyl-1H-imidazol-2-yl)-pyridin-4-yloxy]-1H-benzoimidazol-2-yl}-(3-trifluoromethyl-phenyl)-amine,
(3-Ethyl-phenyl)-{1-methyl-5-[2-(4-phenyl-5-trifluoromethyl-1H-imidazol-2-yl)-pyridin-4-yloxy]-1H-benzoimidazol-2-yl}-amine,
(4-tert-Butyl-phenyl)-{1-methyl-5-[2-(4-phenyl-5-trifluoromethyl-1H-imidazol-2-yl)-pyridin-4-yloxy]-1H-benzoimidazol-2-yl}-amine,
(2-Chloro-5-trifluoromethyl-phenyl)-{1-methyl-5-[2-(5-trifluoromethyl-1H-imidazol-2-yl)-pyridin-4-yloxy]-1H-benzoimidazol-2-yl}-amine,
(2-Fluoro-5-trifluoromethyl-phenyl)-{1-methyl-5-[2-(5-methyl-4-phenyl-1H-imidazol-2-yl)-pyridin-4-yloxy]-1H-benzoimidazol-2-yl}-amine,
(2-Chloro-5-trifluoromethyl-phenyl)-{1-methyl-5-[2-(5-methyl-4-phenyl-1H-imidazol-2-yl)-pyridin-4-yloxy]-1H-benzoimidazol-2-yl}-amine,
(4-tert-Butyl-phenyl)-{1-methyl-5-[2-(5-methyl-4-phenyl-1H-imidazol-2-yl)-pyridin-4-yloxy]-1H-benzoimidazol-2-yl}-amine,
{1-Methyl-5-[2-(5-methyl-4-phenyl-1H-imidazol-2-yl)-pyridin-4-yloxy]-1H-benzo-imidazol-2-yl}-(3-trifluoromethyl-phenyl)-amine,
(5-tert-Butyl-2-fluoro-phenyl)-{1-methyl-5-[2-(5-methyl-4-phenyl-1H-imidazol-2-yl)-pyridin-4-yloxy]-1H-benzoimidazol-2-yl}-amine,
[4-(4-Methyl-piperazin-1-yl)-phenyl]-{1-methyl-5-[2-(5-trifluoromethyl-1H-imidazol-2-yl)-pyridin-4-yloxy]-1H-benzoimidazol-2-yl}-amine,
2-{4-[2-(2-Fluoro-5-trifluoromethyl-phenylamino)-1-methyl-1H-benzoimidazol-5-yl-oxy]-pyridin-2-yl}-3H-imidazole-4-carboxylic acid methyl ester,
2-{4-[2-(2-Chloro-5-trifluoromethyl-phenylamino)-1-methyl-1H-benzoimidazol-5-yl-oxy]-pyridin-2-yl}-5-trifluoromethyl-1H-imidazole-4-carboxylic acid ethyl ester,
(2-Fluoro-4-trifluoromethyl-phenyl)-{1-methyl-5-[2-(5-trifluoromethyl-1H-imidazol-2-yl)-pyridin-4-yloxy]-1H-benzoimidazol-2-yl}-amine,
(2-Chloro-phenyl)-{1-methyl-5-[2-(5-trifluoromethyl-1H-imidazol-2-yl)-pyridin-4-yl-oxy]-1H-benzoimidazol-2-yl}-amine,
(2,5-Dimethoxy-phenyl)-{1-methyl-5-[2-(5-trifluoromethyl-1H-imidazol-2-yl)-pyridin-4-yloxy]-1H-benzoimidazol-2-yl}-amine, (3,5-Dimethoxy-phenyl)-{1-methyl-5-[2-(5-trifluoromethyl-1H-imidazol-2-yl)-pyridin-4-yloxy]-1H-benzoimidazol-2-yl}-amine,
{1-Methyl-5-[2-(5-trifluoromethyl-1H-imidazol-2-yl)-pyridin-4-yloxy]-1H-benzo-imidazol-2-yl}-(2-trifluoromethyl-phenyl)-amine,
(2-Ethyl-phenyl)-{1-methyl-5-[2-(5-trifluoromethyl-1H-imidazol-2-yl)-pyridin-4-yloxy]-1H-benzoimidazol-2-yl}-amine,
(4-Ethyl-piperazin-1-yl)-(2-{4-[2-(2-fluoro-5-trifluoromethyl-phenylamino)-1-methyl-1H-benzoimidazol-5-yloxy]-pyridin-2-yl}-3H-imidazol-4-yl)-methanone,
2-{4-[2-(2-Fluoro-5-trifluoromethyl-phenylamino)-1-methyl-1H-benzoimidazol-5-yl-oxy]-pyridin-2-yl}-3H-imidazole-4-carboxylic acid (2-hydroxy-ethyl)-amide,
{1-Ethyl-5-[2-(5-trifluoromethyl-1H-imidazol-2-yl)-pyridin-4-yloxy]-1H-benzoimidazol-2-yl}-(2-fluoro-5-trifluoromethyl-phenyl)-amine,
(2-Fluoro-5-trifluoromethyl-phenyl)-{6-methoxy-1-methyl-5-[2-(5-trifluoromethyl-1H-imidazol-2-yl)-pyridin-4-yloxy]-1H-benzoimidazol-2-yl}-amine,
{6-Methoxy-1-methyl-5-[2-(5-trifluoromethyl-1H-imidazol-2-yl)-pyridin-4-yloxy]-1H-benzoimidazol-2-yl}-(4-trifluoromethyl-phenyl)-amine,
(4-Ethyl-piperazin-1-yl)-(2-{4-[1-methyl-2-(4-trifluoromethyl-phenylamino)-1H-benzo-imidazol-5-yloxy]-pyridin-2-yl}-3H-imidazol-4-yl)-methanone,
{1-Ethyl-5-[2-(5-trifluoromethyl-1H-imidazol-2-yl)-pyridin-4-yloxy]-1H-benzoimidazol-2-yl}-(4-trifluoromethyl-phenyl)-amine,
2-{4-[1-Methyl-2-(4-trifluoromethyl-phenylamino)-1H-benzoimidazol-5-yloxy]-pyridin-2-yl}-3H-imidazole-4-carboxylic acid (2-hydroxy-ethyl)-amide,
2-{1-Methyl-5-[2-(5-trifluoromethyl-1H-imidazol-2-yl)-pyridin-4-yloxy]-1H-benzo-imidazol-2-ylamino}-5-trifluoromethyl-phenol, and
3-{1-Methyl-5-[2-(5-trifluoromethyl-1H-imidazol-2-yl)-pyridin-4-yloxy]-1H-benzo-imidazol-2-ylamino}-6-trifluoromethyl-phenol;

or a tautomer, stereoisomer, ester, metabolite, prodrug, or pharmaceutically acceptable salt thereof.

In one embodiment, provided is a method for preparing a compound of Formula (IXa) or its tautomer (IXb) or a pharmaceutically acceptable salt or metabolite thereof

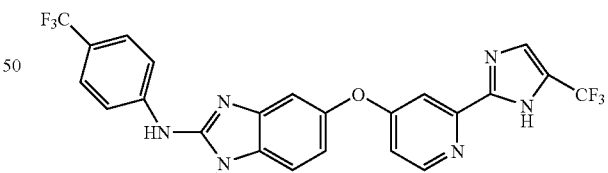

(IXa)

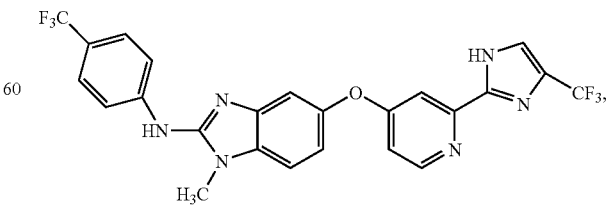

(IXb)

the method comprising:

(a) reacting the compound of Formula (XI) or a tautomer thereof with 4-trifluoromethyphenylisothiocyanate to provide a compound of Formula (XII) or a tautomer thereof

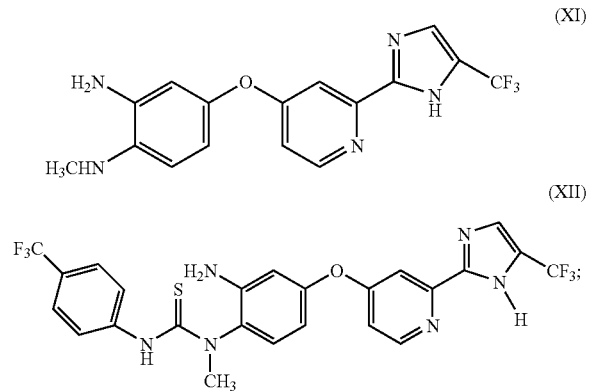

(b) reacting the compound of Formula (XII) or a tautomer thereof with a desulfurizing agent to provide the compound of Formula (IXa) or (IXb);

(c) optionally reacting the compound of Formula (IXa) or (IXb) with an acid to give a first pharmaceutically acceptable salt;

(d) optionally converting the first pharmaceutically acceptable salt of a compound of Formula (IXa) or (IXb) to a second pharmaceutically acceptable salt; and (e) optionally converting the compound or pharmaceutically acceptable salt of Formula (IXa) or (IXb) to a metabolite thereof.

In one embodiment, part (a) is carried out in acetonitrile.

In one embodiment, the desulfurizing agent in part (b) is selected from the group consisting of $FeCl_3$, 2-chloro-1-methylpyridinium iodide, 2-chloro-1,3-dimethylimidazolium chloride, and $POCl_3$.

In one embodiment, the compound of Formula (XI) is prepared by (a) reacting 4-methylamino-3-nitrophenol or an anion thereof with 4-chloropyridine-2-carboxylic acid tert-butyl ester to provide 4-(4-methylamino-3-nitrophenoxy)-pyridine-2-carboxylic acid tert-butyl ester;

(b) converting the 4-(4-methylamino-3-nitrophenoxy)-pyridine-2-carboxylic acid tert-butyl ester to 4-(4-methylamino-3-nitrophenoxy)-pyridine-2-carbaldehyde;

(c) reacting the 4-(4-methylamino-3-nitrophenoxy)-pyridine-2-carbaldehyde with 3,3,3-trifluoro-2-oxopropanal to provide a compound of Formula (X) or a tautomer thereof

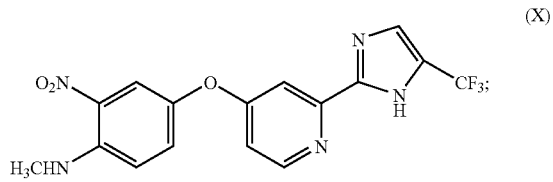

(d) reacting the compound of Formula (X) or a tautomer thereof with a reducing agent to provide a compound of Formula (XI) or tautomer thereof.

In some such aspects, part (a) is carried out in a basic solution. In some such aspects the basic solution is a dimethylsulfoxide solution containing $K_2CO_3$.

In some such aspects, the 4-methylamino-3-nitrophenol in part (a) is prepared from 4-amino-3-nitrophenol. In some such aspects, 4-amino-3-nitrophenol is contacted with formic acid and acetic anhydride to provide a formamide product, and said formamide product is contacted with a reducing agent to provide the 4-methylamino-3-nitrophenol. In other aspects, the reducing agent is sodium borohydride and boron trifluoride diethyl etherate. In still other aspects, 4-amino-3-nitrophenol is contacted with trifluoroacetic anhydride to provide an amide product, said amide product is contacted with dimethylsulfate under basic conditions to provide the 4-methylamino-3-nitrophenol.

In some such aspects, the 4-chloropyridine-2-carboxylic acid tert-butyl ester in part (a) is prepared from picolinic acid. In some such aspects, picolinic acid is contacted with thionyl chloride and sodium hydroxide to provide 4-chloropyridine-2-carbonyl chloride. In still other such aspects, the 4-chloropyridine-2-carbonyl chloride is contacted with di-t-butyl dicarbonate and pyridine to provide the 4-chloropyridine-2-carboxylic acid tert-butyl ester.

In some such aspects, the 4-(4-methylamino-3-nitrophenoxy)-pyridine-2-carboxylic acid tert-butyl ester in part (b) is contacted with a reducing agent to provide the 4-(4-methylamino-3-nitrophenoxy)-pyridine-2-carbaldehyde. In some such aspects, the reducing agent is diisobutylaluminum hydride. In other aspects, the 4-(4-methylamino-3-nitrophenoxy)-pyridine-2-carboxylic acid tert-butyl ester in part (b) is contacted with a reducing agent to provide (4-(4-(methylamino)-3-nitrophenoxy)pyridine-2-yl)methanol that is then contacted with an oxidizing agent to provide the 4-(4-methylamino-3-nitrophenoxy)-pyridine-2-carbaldehyde. In some aspects, the reducing agent is lithium aluminum hydride or lithium borohydride. In some aspects, the oxidizing agent is $MnO_2$.

In some such aspects, the reaction of 4-(4-methylamino-3-nitrophenoxy)-pyridine-2-carbaldehyde with 3,3,3-trifluoro-2-oxopropanal is carried out in polar solvent containing $NH_4OH$. In some such aspects, the polar solvent is an ethyl acetate and ethanol mixture.

In some aspects, the 3,3,3-trifluoro-2-oxopropanal is prepared by reacting 1,1-dibromo-3,3,3-trifluoroacetone with sodium acetate in water.

In one embodiment, the compound of Formula (XI) is prepared by (a) reacting 4-methylamino-3-nitrophenol or an anion thereof with 4-chloropyridine-2-carbonitrile to provide 4-(4-methylamino-3-nitrophenoxy)-pyridine-2-carbonitrile;

(b) converting the cyano functionality of 4-(4-methylamino-3-nitrophenoxy)-pyridine-2-carbonitrile to an amidino functionality and reacting said amidino functionality with 3-bromo-1,1,1-trifluoroacetone under imidazole ring forming conditions to provide a compound of Formula (X) or a tautomer thereof

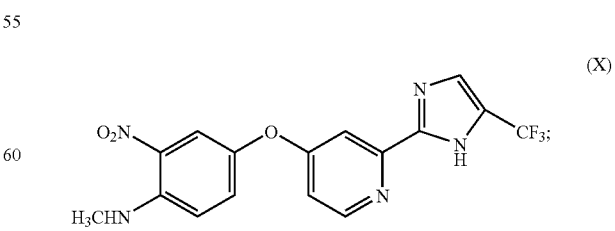

(c) reacting the compound of Formula (X) or a tautomer thereof with a reducing agent to provide a compound of Formula (XI) or tautomer thereof.

In some aspects, the amidino functionality of part (b) is formed by treating 4-(4-methylamino-3-nitrophenoxy)-pyridine-2-carbonitrile with an alkoxide and an ammonium reagent. In one aspect, the alkoxide is sodium methoxide. In other aspects, the ammonium reagent is ammonium acetate. In another aspect, the ammonium reagent is ammonium benzoate.

In some aspects, the imidazole ring forming conditions of part (b) comprises exposing the amidino reaction product to an acid. In one aspect, the acid is an organic acid. Suitable organic acids include acetic acid, methanesulfonic acid, camphorsulfonic acid, trifluoromethanesulfonic acid, and trifluoroacetic acid. In another aspect, the acid is an inorganic acid such as hydrochloric acid and sulfuric acid.

In some aspects, the imidazole ring forming conditions of part (b) comprises heating the reaction product formed from the reaction of the amidino functionality with 3-bromo-1,1,1-trifluoroacetone. In some aspects, the heating is carried out in an alcoholic solvent. Suitable alcoholic solvents include 1-propanol. In some embodiments, the heating is carried out at a temperature of about 80° C. to 100° C. In other embodiments the heating is carried out at about 85° C.

In some such aspects, the reducing agent in part (d) is sodium dithionite $Na_2S_2O_4$.

In one embodiment, the compound of Formula (XI) is prepared by (a) reacting 4-methylamino-3-nitrophenol or an anion thereof with 4-chloro-2-(5-(trifluoromethyl)-1H-imidazol-2-yl)pyridine to provide a compound of Formula (X) or a tautomer thereof

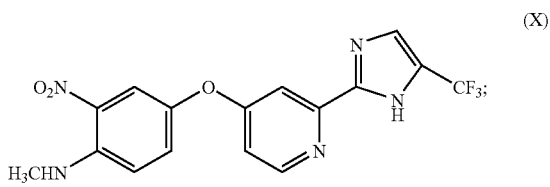

(X)

and (b) reacting the compound of Formula (X) or a tautomer thereof with a reducing agent to provide a compound of Formula (XI) or tautomer thereof.

In some such aspects, the reducing agent in part (b) is sodium dithionite $Na_2S_2O_4$.

In another embodiment, provided is a method for preparing a compound of Formula (Ia) or a tautomer, stereoisomer, ester, metabolite, prodrug, or pharmaceutically acceptable salt thereof.

wherein,

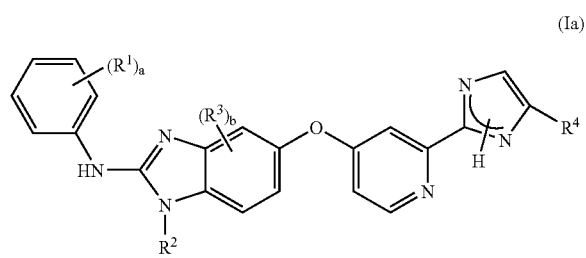

(Ia)

each $R^1$ is independently selected from the group consisting of hydroxy, halo, $C_{1-6}$ alkyl, $C_{1-6}$ alkoxy, ($C_{1-6}$ alkyl) sulfanyl, ($C_{1-6}$ alkyl)sulfonyl, cycloalkyl, heterocycloalkyl, phenyl, and heteroaryl;

$R^2$ is $C_{1-6}$ alkyl or halo($C_{1-6}$ alkyl);

each $R^3$ is independently selected from the group consisting of halo, $C_{1-6}$ alkyl, and $C_{1-6}$ alkoxy;

$R^4$ is independently selected from the group consisting of $C_{1-6}$ alkyl, cycloalkyl, heterocycloalkyl, phenyl, and heteroaryl;

wherein;

a is 1, 2, 3, 4, or 5; and b is 0, 1, 2, or 3;

the method comprising:

(a) converting the cyano functionality of a compound of Formula (XVI) to an amidino functionality and reacting said amidino functionality with a compound of Formula (Va) wherein $X^a$ is a leaving group

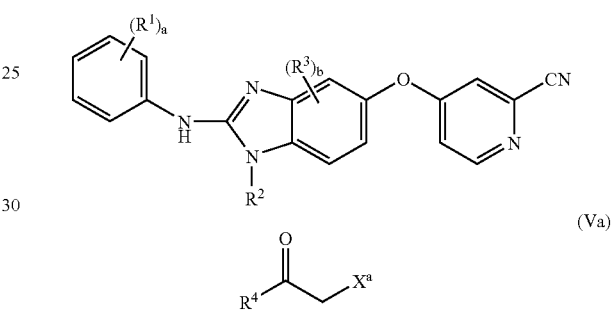

(XVI)

(Va)

to provide a compound of Formula (XVII)

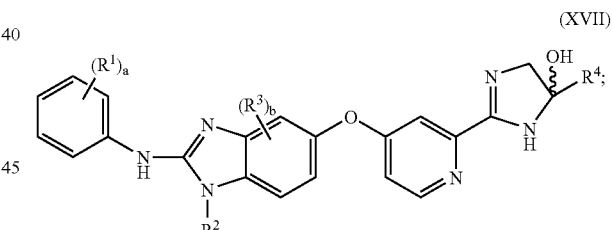

(XVII)

and (b) dehydrating a compound of Formula (XVII) to provide a compound of Formula (Ia);

(c) optionally reacting the compound of Formula (Ia) or a tautomer thereof with an acid to give a first pharmaceutically acceptable salt;

(d) optionally converting the first pharmaceutically acceptable salt of a compound of Formula (Ia) or a tautomer thereof to a second pharmaceutically acceptable salt; and (e) optionally converting a compound of Formula (Ia) or a tautomer thereof to a prodrug or metabolite of Formula (Ia).

In one embodiment, the leaving group $X^a$ in the compound of Formula (Va) is halogen. In another embodiment, $X^a$ is $—SO_2R^{10}$ where $R^{10}$ is $C_{1-6}$ alkyl or phenyl, wherein $C_{1-6}$ alkyl or phenyl are optionally substituted with one to three halo, $C_{1-6}$ alkoxy, or $C_{1-6}$ alkyl groups. In some aspects, $R^{10}$ is methyl or trifluoromethyl.

In one embodiment, the compound of Formula (Va) is 3-bromo-1,1,1-trifluoroacetone (i.e. $X^a$ is Br and $R^4$ is $CF_3$).

In one embodiment, the compound of Formula (XVI) is 4-[1-methyl-2-(4-(trifluoromethyl)phenylamino)-1H-benzoimidazol-5-yloxy]-pyridine-2-carbonitrile (i.e. $R^1$ is 4-$CF_3$, $R^2$ is methyl, and b is 0).

In one embodiment, the amidino functionality of part (a) is formed from a cyano functionality by treating the compound of Formula (XVI) with an alkoxide and an ammonium reagent. In one aspect, the alkoxide is sodium methoxide. In other aspects, the ammonium reagent is ammonium acetate. In another aspect, the ammonium reagent is ammonium benzoate.

In one embodiment, the dehydration of part (b) comprises exposing a compound of Formula (XVII) to an acid. In one aspect, the acid is an organic acid. Suitable organic acids include acetic acid, methanesulfonic acid, camphorsulfonic acid, trifluoromethanesulfonic acid, and trifluoroacetic acid. In another aspect, the acid is an inorganic acid such as hydrochloric acid and sulfuric acid.

In other embodiments, the dehydration of part (b) comprises heating a compound of Formula (XVII) to form a compound of Formula (Ia). In some aspects, the dehydration of part (b) is carried out in an alcoholic solvent. Suitable alcoholic solvents include 1-propanol. In some embodiments, the dehydration is carried out at a temperature of about 80° C. to 100° C. In other embodiments the dehydration is carried out at about 85° C.

In another embodiment, the compound of Formula (XVI) is prepared by (a) reacting a compound of Formula (XVIII) with a compound of Formula (XIX) to provide a compound of Formula (XX)

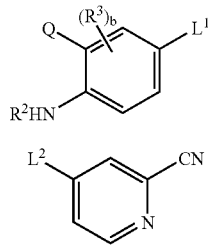

(XVIII)

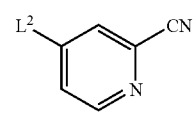

(XIX)

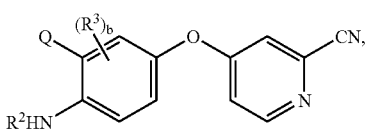

(XX)

wherein $R^2$, $R^3$, and b are as defined herein, Q is $NH_2$ or $NO_2$ and one of $L^1$ or $L^2$ is halo and the other of $L^1$ or $L^2$ is OH or an anion thereof;

(c) reacting the compound of Formula (XX) with a compound of Formula (XXI) wherein $R^1$ and a are as defined herein to provide a compound of Formula (XXII)

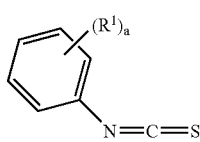

(XXI)

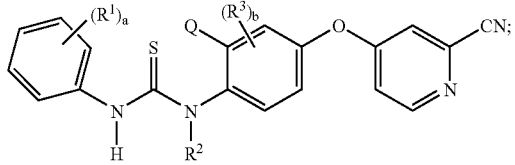

(XXII)

(d) when in the compound of Formula (XXII) Q is $NO_2$, converting said compound to a compound of Formula (XXII) wherein Q is $NH_2$; and (e) reacting the compound of Formula (XXII) wherein Q is $NH_2$ with a desulfurizing agent to provide the compound of Formula (XVI).

In one embodiment, part (a) is carried out with organic or inorganic base in polar solvent. In some aspects, the inorganic base is selected from the group consisting of NaOH, KOH, $CaCO_3$, and $K_2CO_3$. In other aspects, the polar solvent is selected from the group consisting of dimethylsulfoxide and dimethylformamide.

In one embodiment, the compound of Formula (XVIII) is 4-methylamino-3-nitrophenol (i.e. $R^2$ is methyl, Q is $NO_2$, b is 0, and $L^1$ is OH).

In one embodiment, the compound of Formula (XIX) is 4-chloro-2-cyano-pyridine (i.e. $L^2$ is chloro).

In one embodiment, the compound of Formula (XX) is 4-(4-methylamino-3-nitro-phenoxy)-pyridine-2-carbonitrile.

In one embodiment, the compound of Formula (XXI) is 4-trifluoromethylphenylisothiocyanate.

In one embodiment, part (d) comprises reacting a compound of Formula (XXII) with a reducing agent. In some aspects, the reducing agent is sodium dithionite.

In one embodiment, part (e) is carried out in acetonitrile.

In one embodiment, the desulfurizing agent in part (e) is selected from the group consisting of $FeCl_3$, 2-chloro-1-methylpyridinium iodide, 2-chloro-1,3-dimethylimidazolium chloride, and $POCl_3$. In other embodiments, the desulfurizing agent is 2-chloro-1,3-dimethylimidazolium chloride.

In another embodiment, provided is a method for preparing a pharmaceutically acceptable salt of a compound of Formula (Ia) or tautomer thereof

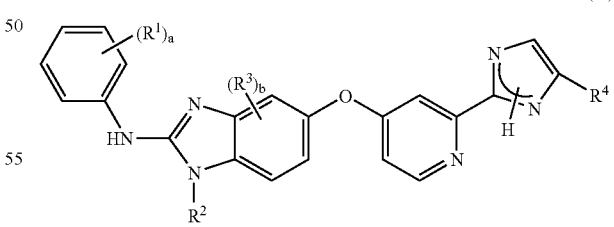

(Ia)

wherein, each $R^1$ is independently selected from the group consisting of hydroxy, halo, $C_{1-6}$ alkyl, $C_{1-6}$ alkoxy, ($C_{1-6}$ alkyl)sulfanyl, ($C_{1-6}$ alkyl)sulfonyl, cycloalkyl, heterocycloalkyl, phenyl, and heteroaryl;

$R^2$ is $C_{1-6}$ alkyl or halo($C_{1-6}$ alkyl);

each $R^3$ is independently selected from the group consisting of halo, $C_{1-6}$ alkyl, and $C_{1-6}$ alkoxy;

$R^4$ is independently selected from the group consisting of $C_{1-6}$ alkyl, cycloalkyl, heterocycloalkyl, phenyl, and heteroaryl;

wherein $R^1$, $R^2$, $R^3$, and $R^4$ may be optionally substituted with one or more substituents independently selected from the group consisting of hydroxy, halo, $C_{1-6}$ alkyl, halo($C_{1-6}$ alkyl), $C_{1-6}$ alkoxy, and halo($C_{1-6}$ alkoxy);

a is 1, 2, 3, 4, or 5; and b is 0, 1, 2, or 3;

the method comprising:

(a) reacting a compound of Formula (Ia) or a tautomer thereof with an acid to give a first pharmaceutically acceptable salt; or (b) converting the first pharmaceutically acceptable salt of a compound of Formula (Ia) or a tautomer thereof to a second pharmaceutically acceptable salt.

In another embodiment, provided is an intermediate compound having Formula (XVI)

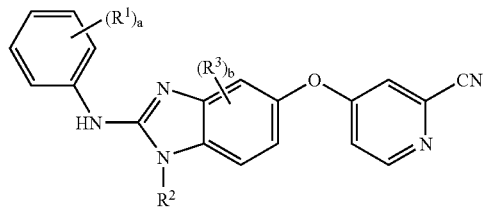

(XVI)

wherein, each $R^1$ is independently selected from the group consisting of hydroxy, halo, $C_{1-6}$ alkyl, $C_{1-6}$ alkoxy, ($C_{1-6}$ alkyl)sulfanyl, ($C_{1-6}$ alkyl)sulfonyl, cycloalkyl, heterocycloalkyl, phenyl, and heteroaryl;

$R^2$ is $C_{1-6}$ alkyl or halo($C_{1-6}$ alkyl);

each $R^3$ is independently selected from the group consisting of halo, $C_{1-6}$ alkyl, and $C_{1-6}$ alkoxy;

wherein $R^1$, $R^2$, and $R^3$ may be optionally substituted with one or more substituents independently selected from the group consisting of hydroxy, halo, $C_{1-6}$ alkyl, halo($C_{1-6}$ alkyl), $C_{1-6}$ alkoxy, and halo($C_{1-6}$ alkoxy);

a is 1, 2, 3, 4, or 5; and b is 0, 1, 2, or 3;

provided that the compound is not 4-[2-(4-chloro-phenylamino)-1-methyl-1H-benzoimidazol-5-yloxy]-pyridine-2-carbonitrile.

In one embodiment, the compound of Formula (XVI) is 4-[1-methyl-2-(4-(trifluoromethyl)phenylamino)-1H-benzoimidazol-5-yloxy]-pyridine-2-carbonitrile.

In one embodiment, provided is use of a compound of Formula (XVI) in the manufacture of a medicament for treating a disease mediated by Raf kinase. In some aspects, the disease is cancer.

The following terms are employed in the application herewith.

"Raf inhibitor" is used herein to refer to a compound that exhibits an $IC_{50}$ with respect to Raf Kinase activity of no more than about 100 μM and more typically not more than about 50 μM, as measured in the Raf/Mek Filtration Assay described in U.S. provisional application 60/712,539.

"Alkyl" refers to saturated hydrocarbyl groups that do not contain heteroatoms and includes straight chain alkyl groups such as methyl, ethyl, propyl, butyl, pentyl, hexyl, heptyl, octyl, nonyl, decyl, undecyl, dodecyl and the like. Alkyl also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH$_2$CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. Thus alkyl groups include primary alkyl groups, secondary alkyl groups, and tertiary alkyl groups. The phrase "$C_{1-12}$ alkyl" refers to alkyl groups having from one to twelve carbon atoms. The phrase "$C_{1-6}$ alkyl" refers to alkyl groups having from one to six carbon atoms.

"Alkenyl" refers to straight or branched hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers.

"Alkoxy" refers to RO— wherein R is an alkyl group. The phrase "$C_{1-6}$ alkoxy" as used herein refers to RO— wherein R is a $C_{1-6}$ alkyl group. Representative examples of $C_{1-6}$ alkoxy groups include methoxy, ethoxy, t-butoxy, and the like.

"($C_{1-6}$ alkoxy)carbonyl" refers to ester —C(=O)—OR wherein R is $C_{1-6}$ alkyl.

"Amidino" or "amidino functionality" refers to the group —C(=NH)NH$_2$. "Amidine" refers to a compound containing such a group.

"Aminocarbonyl" refers herein to the group —C(O)—NH$_2$.

"$C_{1-6}$ alkylaminocarbonyl" refers to the group —C(O)—NRR' where R is $C_{1-6}$ alkyl and R' is selected from hydrogen and $C_{1-6}$ alkyl.

"Carbonyl" refers to the divalent group —C(O)—.

"Carboxyl" refers to —C(=O)—OH.

"Cyano", "carbonitrile", or "nitrile", or "cyano functionality" refers to —CN.

"Cycloalkyl" refers to a mono- or polycyclic alkyl substituent. Typical cycloalkyl groups have from 3 to 8 carbon ring atoms. Representative cycloalkyl groups include cyclopropyl, cyclobutyl, cyclopentyl, cyclohexyl, cycloheptyl, and cyclooctyl.

"Halogen" or "halo" refers to chloro, bromo, fluoro, and iodo groups.

"Halo($C_{1-6}$ alkyl)" refers to a $C_{1-6}$ alkyl radical substituted with one or more halogen atoms, preferably one to five halogen atoms. A more preferred halo($C_{1-6}$ alkyl) group is trifluoromethyl.

"Halo($C_{1-6}$ alkyl)phenyl" refers to a phenyl group substituted with a halo($C_{1-6}$ alkyl) group.

"Halo($C_{1-6}$ alkoxy)" refers to an alkoxy radical substituted with one or more halogen atoms, preferably one to five halogen atoms. A more preferred halo($C_{1-6}$ alkoxy) group is trifluoromethoxy.

"Halo($C_{1-6}$ alkyl)sulfonyl" and "halo($C_{1-6}$ alkyl)sulfanyl" refer to substitution of sulfonyl and sulfanyl groups with halo($C_{1-6}$ alkyl) groups wherein sulfonyl and sulfanyl are as defined herein (e.g. —SO$_2$-haloalkyl or —S-haloalkyl).

"Heteroaryl" refers to an aromatic group having from 1 to 4 heteroatoms as ring atoms in an aromatic ring with the remainder of the ring atoms being carbon atoms. Suitable heteroatoms employed in compounds of the present invention are nitrogen, oxygen, and sulfur, wherein the nitrogen and sulfur atoms may be optionally oxidized. Exemplary heteroaryl groups have 5 to 14 ring atoms and include, for example, benzimidazolyl, benzothiazolyl, benzoxazolyl, diazapinyl, furanyl, pyrazinyl, pyrazolyl, pyridyl, pyridazinyl, pyrimidinyl, pyrroyl, oxazolyl, isoxazolyl, imidazolyl, indolyl, indazolyl, quinolinyl, isoquinolinyl, quinazolinyl, quinoxalinyl, thiazolyl, thienyl, and triazolyl.

"Heterocycloalkyl" refers herein to cycloalkyl substituents that have from 1 to 5, and more typically from 1 to 2 heteroatoms in the ring structure. Suitable heteroatoms employed in compounds of the present invention are nitrogen, oxygen, and sulfur, wherein the nitrogen and sulfur atoms may be optionally oxidized. Representative heterocycloalkyl moieties include, for example, morpholino, piperazinyl, piperidinyl, and the like.

"($C_{1-6}$ alkyl)heterocycloalkyl" refers to a heterocycloalkyl group substituted with a $C_{1-6}$ alkyl group.

"Heterocycloalkylcarbonyl" refers herein to the group —C(O)—$R^{10}$ where $R^{10}$ is heterocycloalkyl.

"($C_{1-6}$ alkyl)heterocycloalkylcarbonyl" refers to the group —C(O)—$R^{11}$ where $R^{11}$ is ($C_{1-6}$ alkyl)heterocycloalkyl.

"Hydroxy" refers to —OH.

"Hydroxy($C_{1-6}$ alkyl)" refers to a $C_{1-6}$ alkyl group substituted with hydroxy.

"Hydroxy($C_{1-6}$ alkylaminocarbonyl)" refers to a $C_{1-6}$ alkylaminocarbonyl group substituted with hydroxy.

"Imidate" or "imidate ester" refers to the group —C(=NH)O— or to a compound containing such a group. Imidate esters include, for example, the methyl ester imidate —C(=NH)OCH$_3$.

"Nitro" refers to —NO$_2$.

"Sulfonyl" refers herein to the group —SO$_2$—.

"Sulfanyl" refers herein to the group —S—. "Alkylsulfonyl" refers to a substituted sulfonyl of the structure —SO$_2$R$^{12}$ in which R$^{12}$ is alkyl. "Alkylsulfanyl" refers to a substituted sulfanyl of the structure —SR$^{12}$ in which R$^{12}$ is alkyl. Alkylsulfonyl and alkylsulfanyl groups employed in compounds of the present invention include (C$_{1-6}$ alkyl)sulfonyl and (C$_{1-6}$ alkyl)sulfanyl. Thus, typical groups include, for example, methylsulfonyl and methylsulfanyl (i.e., where R$^{12}$ is methyl), ethylsulfonyl and ethylsulfanyl (i.e., where R$^{12}$ is ethyl), propylsulfonyl and propylsulfanyl (i.e., where R$^{12}$ is propyl), and the like.

"Hydroxy protecting group" refers to protecting groups for an OH group. The term as used herein also refers to protection of the OH group of an acid COOH. Suitable hydroxy protecting groups as well as suitable conditions for protecting and deprotecting particular functional groups are well known in the art. For example, numerous such protecting groups are described in T. W. Greene and P. G. M. Wuts, Protecting Groups in Organic Synthesis, Third Edition, Wiley, New York, 1999. Such hydroxy protecting groups include C$_{1-6}$ alkyl ethers, benzyl ethers, p-methoxybenzyl ethers, silyl ethers, esters, carbonates, and the like.

"Metabolite" refers to any derivative produced in a subject after administration of a parent compound. The derivatives may be produced from the parent compound by various biochemical transformations in the subject such as, for example, oxidation, reduction, hydrolysis, or conjugation and include, for example, oxides and demethylated derivatives. Metabolites corresponding to such derivatives may also be produced by in vitro methods or through synthetic methods. In some embodiments, the metabolite of a compound of Formula (I) or (Ia) is an oxide. In some aspects, the oxide is an N-oxide that is formed synthetically by treating a compound of Formula (I) or (Ia) with an oxidizing agent. In some aspects the oxidizing agent is N-methylmorpholine N-oxide or a hydroperoxide such as hydrogen peroxide. In some embodiments, a compound of Formula (I) or (Ia) is conjugated to glucuronic acid to form a metabolite. In another aspect, provided is a metabolite, tautomer, or stereoisomer thereof having the structure:

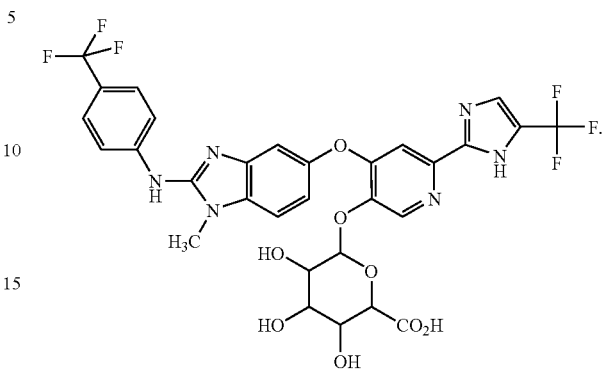

"Optionally substituted" or "substituted" refers to the replacement of one or more hydrogen atoms with a monovalent or divalent radical.

When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substitutents can be straight chain, branched or cyclic arrangements of covalently bonded carbon or heteroatoms.

It is understood that the above definitions are not intended to include impermissible substitution patterns (e.g., methyl substituted with five fluoro groups or a halogen atom substituted with another halogen atom). Such impermissible substitution patterns are well known to the skilled artisan.

It will also be apparent to those skilled in the art that the compounds of the invention, including the compounds of Formula (I) and (Ia) or their stereoisomers, esters, prodrugs, or pharmaceutically acceptable salts may be subject to tautomerization and may therefore exist in various tautomeric forms wherein a proton of one atom of a molecule shifts to another atom and the chemical bonds between the atoms of the molecules are consequently rearranged. See, e.g., March, *Advanced Organic Chemistry: Reactions*, Mechanisms and Structures, Fourth Edition, John Wiley & Sons, pages 69-74 (1992). As used herein, the term "tautomer" refers to the compounds produced by the proton shift, and it should be understood that all tautomeric forms, insofar as they may exist, are included within the invention. For example, the tautomers of a compound of Formula (I) where, for illustrative purposes only, R$^2$ is methyl and c is 1 is shown below:

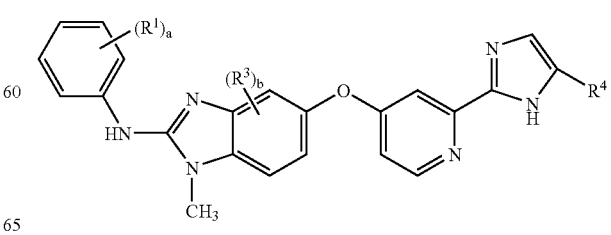

-continued

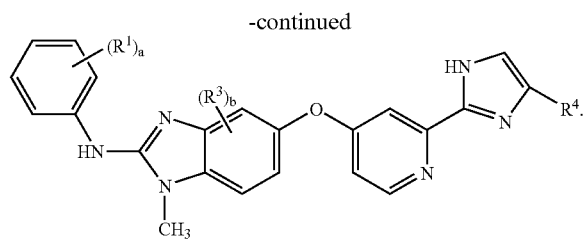

These tautomers may also be depicted in the following manner:

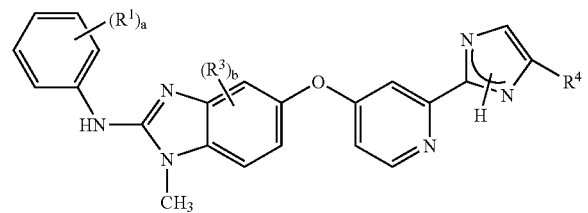

The compounds of the invention, including the compounds of Formulas (I), (Ia), (II) or (III) or their tautomers, stereoisomers, esters, metabolites, prodrugs, or pharmaceutically acceptable salts thereof, may comprise asymmetrically substituted carbon atoms. Such asymmetrically substituted carbon atoms can result in the compounds of the invention existing in enantiomers, diastereomers, and other stereoisomeric forms that may be defined, in terms of absolute stereochemistry, such as in (R)- or (S)-forms. As a result, all such possible isomers, individual stereoisomers in their optically pure forms, mixtures thereof, racemic mixtures (or "racemates"), mixtures of diastereomers, as well as single diastereomers of the compounds of the invention are included in the present invention. The terms "S" and "R" configuration, as used herein, are as defined by the IUPAC 1974 RECOMMENDATIONS FOR SECTION E, FUNDAMENTAL STEREOCHEMISTRY, Pure Appl. Chem. 45:13-30 (1976). The terms α and β are employed for ring positions of cyclic compounds. The α-side of the reference plane is that side on which the preferred substituent lies at the lower numbered position. Those substituents lying on the opposite side of the reference plane are assigned β descriptor. It should be noted that this usage differs from that for cyclic stereoparents, in which "α" means "below the plane" and denotes absolute configuration. The terms α and β configuration, as used herein, are as defined by the CHEMICAL ABSTRACTS INDEX GUIDE-APPENDIX IV (1987) paragraph 203.

As used herein, the term "pharmaceutically acceptable salts" refers to the nontoxic acid or alkaline earth metal salts of the compound, tautomer, stereoiosmer, ester, metabolite, or prodrug of Formulas (I) or (Ia). These salts can be prepared in situ during the final isolation and purification of the compounds of Formulas (I) or (Ia) or by separately reacting the base or acid functions with a suitable organic or inorganic acid or base, respectively. Representative salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-napthalenesulfonate, oxalate, pamoate, pectinate, persulfate, 3-phenylpropionate, picrate, pivalate, propionate, succinate, sulfate, tartrate, thiocyanate, p-toluenesulfonate and undecanoate. Also, the basic nitrogen-containing groups can be quaternized with such agents as $C_{1-6}$ alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, phenyl alkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of Formula (I) or (Ia), or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methyl-amine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

Salts and formulations of the compounds of the invention are also disclosed in provisional applications titled "Formulations For Benzimidazole Pyridyl Ethers" (U.S. Ser. No. 60/832,715) filed on 21 Jul. 2006 and "Salts of Benzimidazolyl Pyridyl Ethers and Formulations Thereof" filed on 30 Aug. 2006 each of which is herein incorporated by reference in its entirety.

As used herein, the term "pharmaceutically acceptable ester" refers to esters, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

It will be apparent to those skilled in the art that the compounds of the invention, including the compounds of Formula (I) or (Ia) or the tautomers, stereoisomers, esters, prodrugs, or pharmaceutically acceptable salts thereof, may be processed in vivo through metabolism in the body to produce pharmacologically active metabolites that retain activity as inhibitors of the enzyme Raf kinase. The active metabolites of a compound of the invention may be identified using routine techniques known in the art. See, e.g., Bertolini, G. et al., *J. Med. Chem.* 40:2011-2016 (1997); Shan, D. et al., *J. Pharm. Sci.* 86(7):765-767; Bagshawe K., *Drug Dev. Res.* 34:220-230 (1995); Bodor, N., *Advances in Drug Res.* 13:224-331 (1984); Bundgaard, H., *Design of Prodrugs* (Elsevier Press 1985); and Larsen, I. K., *Design and Application of Prodrugs, Drug Design and Development* (Krogsgaard-Larsen et al., eds., Harwood Academic Publishers, 1991). It should be understood that the all active metabolites of a compound of the invention are included within the invention.

The term "cancer" refers to cancer diseases that can be beneficially treated by the inhibition of a kinase, particularly Raf kinase, including, for example, solid cancers, such as carcinomas (e.g., of the lungs, pancreas, thyroid, ovarian, bladder, breast, prostate, or colon), melanomas, myeloid disorders (e.g., myeloid leukemia, multiple myeloma, and erythroleukemia), adenomas (e.g., villous colon adenoma) and sarcomas (e.g. osteosarcoma).

The present invention relates to the processes for preparing the compounds of the invention and to the synthetic intermediates useful in such processes, as described in detail below.

Scheme 1 illustrates construction of the central biaryl ether moiety of the compounds of the invention. Compound 1.1 is reacted with compound 1.2 wherein one of $L^1$ or $L^2$ is halo and the other of $L^1$ or $L^2$ is OH to form ether 1.3. The coupling may be carried out in an organic solvent such as acetonitrile or dimethylsulfoxide in the presence of a base and may also be conducted at elevated or refluxing temperatures. Suitable bases include $K_2CO_3$, $CaCO_3$, KOH, NaOH, or $KF.Al_2O_3$ (Journal of Organic Chemistry, Vol. 63, No. 18, 1998 pgs. 6338-6343). The group Q in compound 1.1 may be $NH_2$ or an amino precursor such as $NO_2$ or a protected amino group that can later be converted to the amine by respectively reducing or deprotecting the amino precursors. The Z group in compound 1.2 may be an imidazolyl group substituted with one or two $R^4$ groups or a functional group that can be used to form such an imidazoyl group. Suitable functional groups include an aldehyde, or any aldehyde precursor such as an ester or carbonitrile that can later be converted to the aldehyde. The ester and carbonitrile groups may be reduced to the aldehyde with a reducing agent such as diisobutylaluminum hydride. Z may also be $-CH_2OR^5$, where $R^5$ is a hydroxy protecting group. The aldehyde may be unmasked at a later stage by deprotection of the $R^5$ group and oxidation of the resulting alcohol to the aldehyde. The conversion of the aldehyde to a substituted imidazoyl group is shown in Scheme 3. Other methods for forming the substituted imidazoyl group is shown in Scheme 6.

SCHEME 1

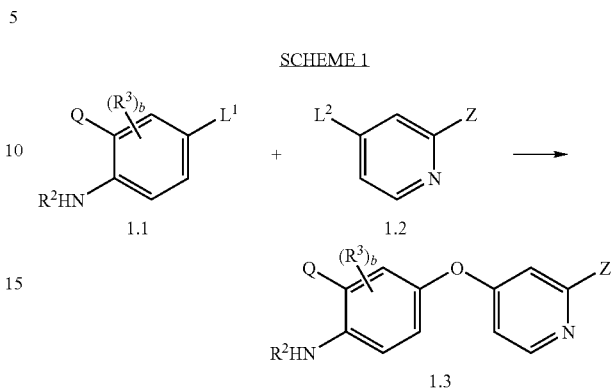

Scheme 2 shows an example of a synthesis of certain biaryl ethers. It is understood that for illustrative purposes, Scheme 2 employs the following substitution patterns: Q is $NO_2$, $L^1$ is OH, $L^2$ is Cl, and Z is a t-butyl ester. An example of the synthesis of aldehyde 2.7 wherein $R^2$ is methyl and b is 0 is shown in Example 1. Amine 2.1 may be converted to alkyl amine 2.2 via a number of known methods. In one aspect, amine 2.1 is treated with acetic anhydride and formic acid to form the corresponding formamide that may be reduced to alkyl amine 2.2. Suitable reducing agents include $NaBH_4$ in the presence of $BF_3(OCH_2CH_3)_2$. Alternatively, alkyl amine 2.2 may be synthesized by reacting amine 2.1 with trifluoroacetic anhydride, alkylating the corresponding amide with an alkylating agent such as an alkyl halide, and removing the trifluoroacetamide protecting group by treatment with base such as NaOH.

Chloride 2.5 may be prepared by treating picolinic acid 2.3 with excess thionyl chloride to form acid chloride 2.4 that is then exposed to di-t-butyl dicarbonate and pyridine to give chloride 2.5. Coupling of the alcohol of the alkyl amine 2.2 with chloride 2.5 under basic conditions gives ether 2.6 than can be converted directly to aldehyde 2.7 by reduction with diisobutylaluminum hydride or in two steps by reduction of ester 2.6 to the alcohol followed by oxidation to the aldehyde.

SCHEME 2

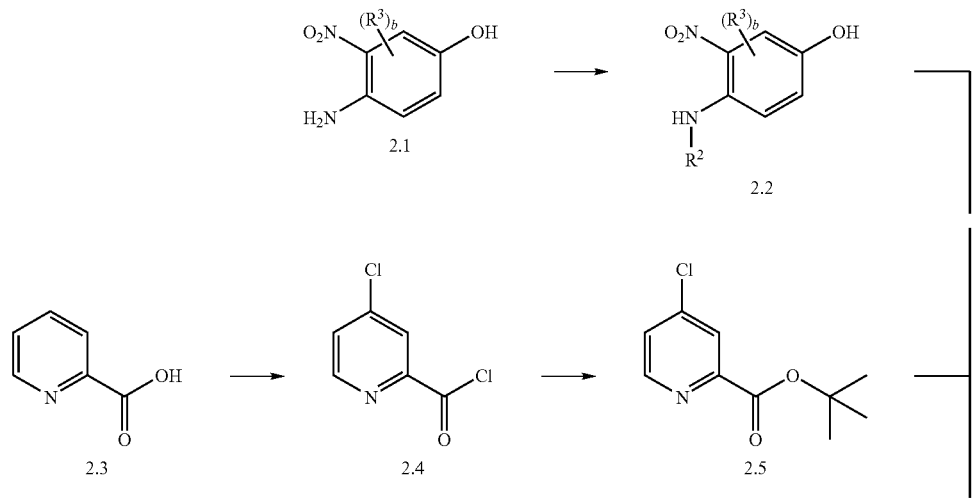

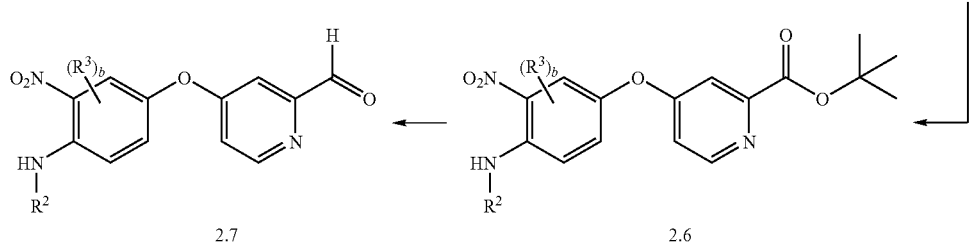

Scheme 3 illustrates the formation of the imidazole ring. Aldehyde 2.7 can be reacted with compound 3.1 wherein $X^b$ is =O or =NHOH and $R^{4p}$ and $R^{4q}$ are independently H or $R^4$, wherein $R^4$ is as previously defined, provided that at least one of $R^{4p}$ and $R^{4q}$ is $R^4$. The reaction may be carried out in a polar solvent such as an ethyl acetate/ethanol mixture and in the presence of $NH_4OH$ to provide compound 3.2. The nitro group of compound 3.2 can be reduced to amine 3.3 by treatment with a reducing agent such as sodium dithionite ($Na_2S_2O_4$).

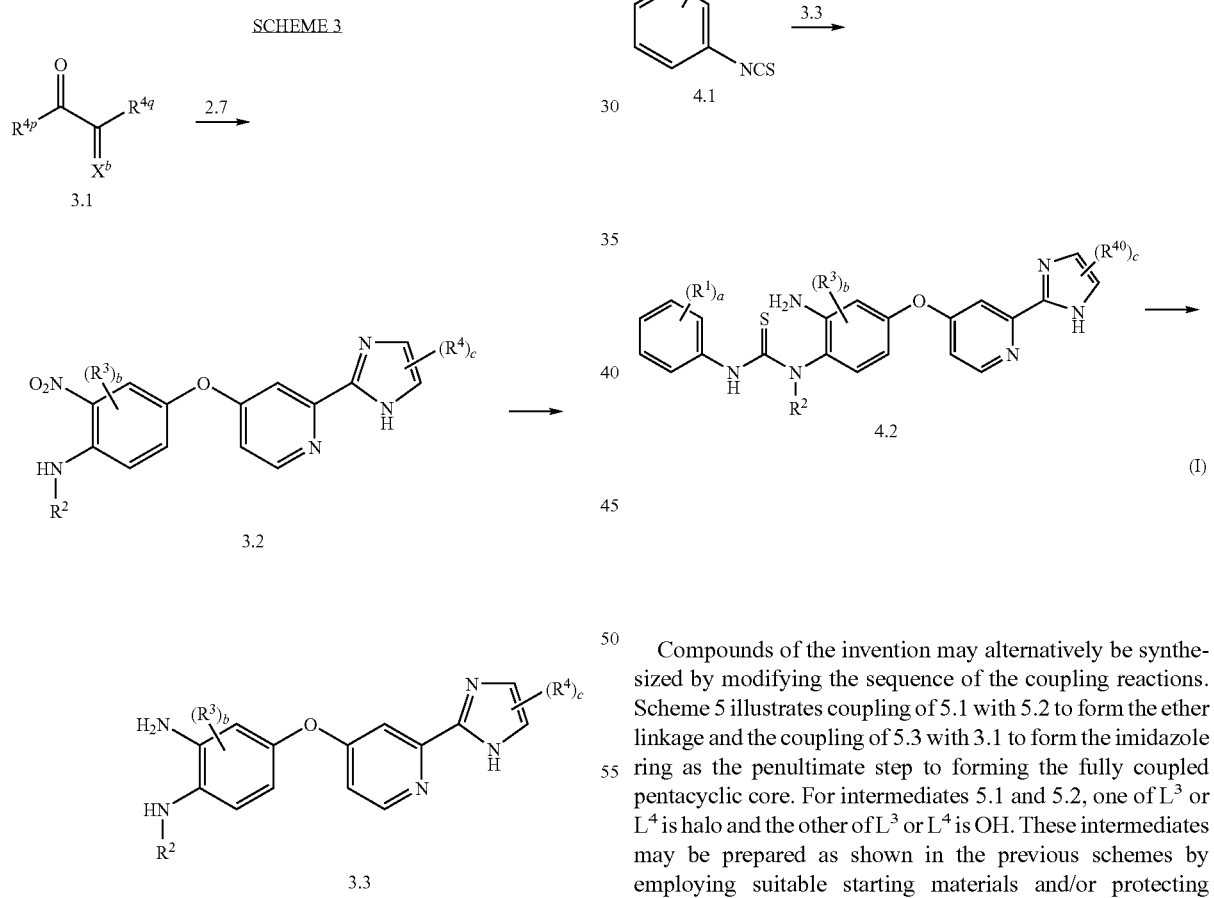

Schemes 4 illustrates formation of the benzimidazole ring. Diamine 3.3 is reacted with thioisocyanate 4.1 to provide thiourea 4.2. Treatment of 4.2 with a desulfurizing agent gives a compound of Formula (I). The term "desulfurizing agent" refers to agents suitable for effecting ring closure such as $FeCl_3$, 2-chloro-1-methylpyridinium iodide (Mukaiyama reagent), 2-chloro-1,3-dimethylimidazolium chloride, $POCl_3$, or an alkyl halide such as methyl iodide. Modified Mukaiyama reagents may also be used (Journal of Organic Chemistry, Vol. 70, No. 7, 2005 pgs. 2835-2838).

Compounds of the invention may alternatively be synthesized by modifying the sequence of the coupling reactions. Scheme 5 illustrates coupling of 5.1 with 5.2 to form the ether linkage and the coupling of 5.3 with 3.1 to form the imidazole ring as the penultimate step to forming the fully coupled pentacyclic core. For intermediates 5.1 and 5.2, one of $L^3$ or $L^4$ is halo and the other of $L^3$ or $L^4$ is OH. These intermediates may be prepared as shown in the previous schemes by employing suitable starting materials and/or protecting groups in the proper reaction sequences. Such factors are within the skill in the art. Aldehyde 5.3, for example, may be prepared by reduction of the corresponding carbonitrile, the synthesis of which is shown in Example 71, with diisobutylaluminum hydride. Reaction of aldehyde 5.3 according to Scheme 3 above with ketone 3.1 affords compounds of Formula (I).

SCHEME 5

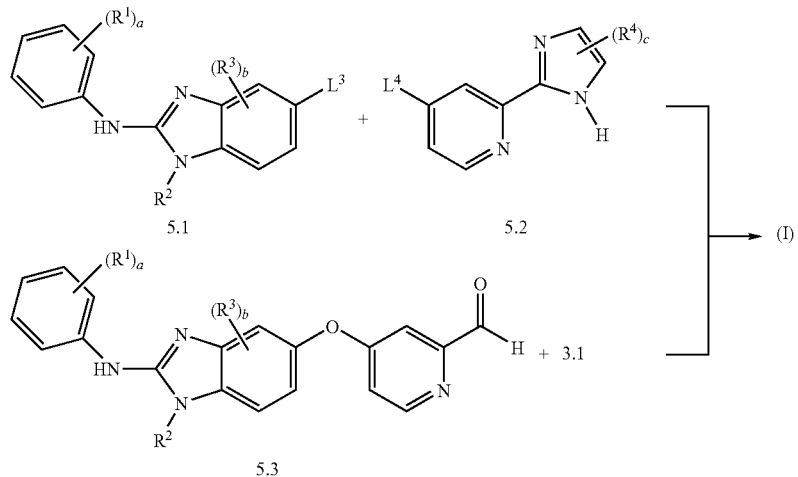

It will be appreciated that the imidazole intermediates used in the coupling reactions can be prepared using other synthetic routes. One such method is shown in Scheme 6. Compound 1.3, where Z is cyano, is converted to a compound where Z is an amidino group. This transformation can be effected by reacting 1.3 with an alkoxide, such as methoxide, to convert the carbonitrile to an imidate ester that is next reacted with an ammonium reagent such as ammonium acetate or ammonium benzoate to form the amidine. Reaction of the amidine with compound (Va), wherein Xa is a leaving group, provides the alkylated and cyclized compound 6.2 or a tautomer thereof. Heating compound 6.2 leads to the elimination of water (dehydration) and the formation of intermediate 6.3. Other dehydration conditions include treatment of 6.2 with organic acids such as acetic acid, methanesulfonic acid, camphorsulfonic acid, trifluoromethanesulfonic acid, and trifluoroacetic acid, as well as with inorganic acids such as hydrochloric acid and sulfuric acid. The four reactions—formation of imidate ester, formation of amidine, alkylation/cyclization, and dehydration—are typically performed in a one pot sequence.

SCHEME 6

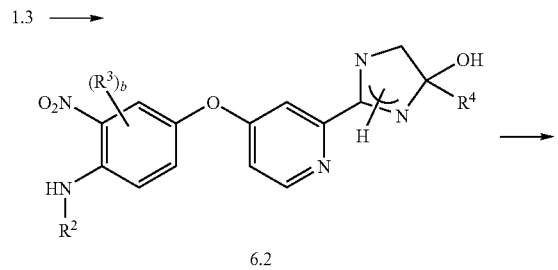

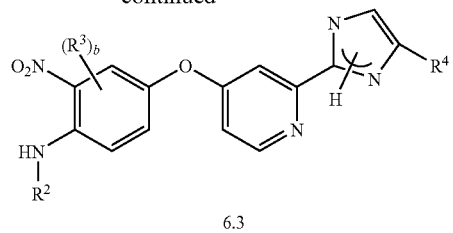

The compounds of the invention are useful in vitro or in vivo in inhibiting the growth of cancer cells. The compounds may be used alone or in compositions together with a pharmaceutically acceptable carrier or excipient. Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), incorporated herein by reference.

While the compounds of the invention can be administered as the sole active pharmaceutical agent, they can also be used in combination with one or more other agents used in the treatment of cancer. The compounds of the present invention are also useful in combination with known therapeutic agents and anti-cancer agents, and combinations of the presently disclosed compounds with other anti-cancer or chemotherapeutic agents are within the scope of the invention. Examples of such agents can be found in *Cancer Principles and Practice of Oncology*, V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The compounds of the invention are also useful when co-administered with radiation therapy.

The present invention will be understood more readily by reference to the following examples, which are provided by way of illustration and are not intended to be limiting of the present invention.

In the Examples below as well as throughout the application, the following abbreviations have the following meanings. If not defined, the terms have their generally accepted meanings.

APCI Atmospheric pressure chemical ionization mass spectroscopy
cm Centimeter
° C. Degrees Celcius
DIPEA Diisopropylethylamine
DMC 2-Chloro-1,3-dimethylimidazolinium chloride
DMSO Dimethylsulfoxide
EtOAc Ethyl Acetate
EtOH Ethanol
g Grams
h Hour
HPLC High Performance Liquid Chromatography
IPA Isopropyl alcohol
L Liter
LCAP Liquid Chromatography Area Percent
MeCN Acetonitrile
mL Milliliters
NaOMe Sodium Methoxide
1-PrOH 1-Propanol
TEA Triethylamine
TFAA Trifluoroacetic anhydride
THF Tetrahydrofuran Example 1

Preparation of {1-Methyl-5-[2-(5-trifluoromethyl-1H-imidazol-2-yl)-pyridin-4-yloxy]-1H-benzoimidazol-2-yl}-(4-trifluoromethyl-phenyl)-amine

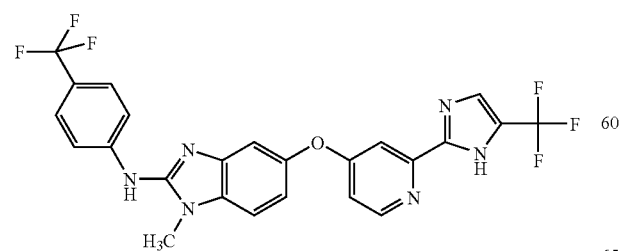

Step 1

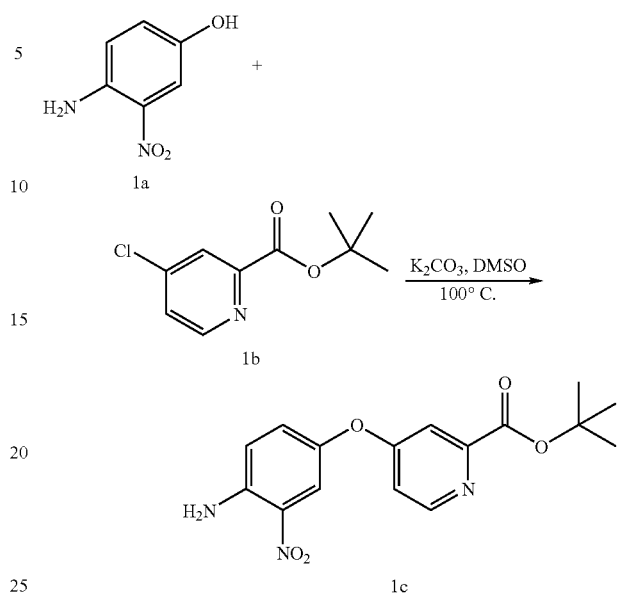

A 500 mL three-neck flask was fitted with a mechanical stirrer and charged with $K_2CO_3$ (4.15 g, 30 mmol). The vessel was sealed, evacuated, and flame dried. The apparatus was allowed to cool to room temperature and purged with argon. To the reaction flask was added 4-amino-3-nitrophenol 1a (3.08 g, 20 mmol), tert-butyl 4-chloropyridine-2-carboxylate 1b (5.2 g, 24 mmol) and dry DMSO (dimethylsulfoxide 30 mL). The resulting mixture was stirred vigorously and heated to 100° C. for 14 h. The reaction was poured over iced phosphate buffer (pH=7) and the reaction flask was rinsed well with MTBE (methyl tert-butyl ether) and water. The combined biphasic mixture was filtered through Celite (>2 cm pad). The layers were partitioned and separated and the aqueous phase was extracted with MTBE (3×100 mL). The combined organic layers were washed with water (5×100 mL), dried ($MgSO_4$), and evaporated. The crude residue was adsorbed onto $SiO_2$, and purified by flash chromatography (4:1, 2:1, 1:1 hexanes-EtOAc (ethyl acetate)) to furnish 4.92 g (14.9 mmol, 74% yield) of 1c as a yellow brown solid. $^1$H NMR (300 MHz, $CDCl_3$) δ 8.58 (d, J=5.8 Hz, 1H), 7.90 (d, J=2.8 Hz, 1H), 7.56 (d, J=2.5 Hz, 1H), 7.17 (dd, J=2.8, 8.8 Hz, 1H), 6.94 (dd, J=2.8, 5.8, Hz, 1H), 6.91 (d, J=9.1 Hz, 1H), 6.15 (br s, 2H), 1.62 (s, 9H); $^{13}$C NMR (75 MHz, $CDCl_3$) δ 165.8, 164.0, 151.8, 151.5, 143.4, 143.2, 131.5, 129.8, 121.0, 118.0, 114.2, 113.1, 83.0, 28.4; mp 163-166° C.

Step 2

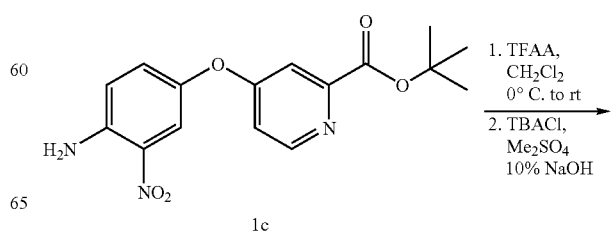

-continued

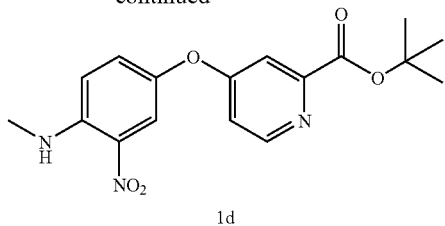
1d

To a solution of the nitroaniline 1c (5.62 g, 17 mmol) in CH$_2$Cl$_2$ (85 mL) at 0° C. was added TFAA (trifluoroacetic anhydride 2.4 mL, 3.6 g, 17 mmol). The cooling bath was then removed and the reaction maintained at room temperature for 2 h. The reaction was cooled to 0° C. and TBACl (tetrabutylammonium chloride, 2.5 g, 8.5 mmol), Me$_2$SO$_4$ (dimethylsulfate 3.2 mL, 4.3 g 34 mmol), and 10% NaOH (34 mL) were added. The resulting mixture was stirred vigorously for 4 h at room temperature. The reaction was diluted with water and the resulting layers were partitioned and separated. The aqueous phase was extracted with CH$_2$Cl$_2$ (3×100 mL), and the combined organic layers were washed with brine (2×100 mL), dried (MgSO$_4$), and evaporated. The crude residue was adsorbed onto silica gel and purified by flash:chromatography (4:1, 2:1, 1:1, 1:2 hexanes/EtOAc) to give 4.5 g (13.0 mmol, 76%) of 1d as a yellow-orange solid. $^1$H NMR (300 MHz, CDCl$_3$) δ 8.54 (d, J=5.5 Hz, 1H), 8.04 (br d, J=4.7 Hz, 1H), 7.93 (d, J=2.8 Hz, 1H), 7.53 (d, J=2.5 Hz, 1H), 7.25 (app dd, J=2.8, 9.1 Hz, 1H), 6.91 (m, 2H), 3.04 (d, J=4.9 Hz, 3H), 1.59 (s, 9H); $^{13}$C NMR (75 MHz, CDCl$_3$) δ 165.9, 164.1, 151.5, 144.7, 142.1, 130.4, 118.8, 115.5, 114.1, 112.9, 82.9, 30.4, 28.5; mp 187-189° C.

Step 3

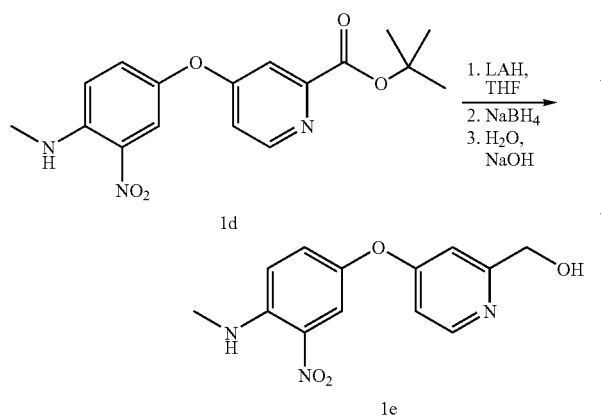

A flame-dried 500 mL three necked round bottom flask purged with N$_2$ was charged with LAH (lithium aluminum hydride, 3.0 g, 75 mmol) and dry THF (240 mL). The resulting suspension was cooled to 0° C. and t-butyl ester 1d (20.7 g, 60 mmol) was slowly added while keeping the internal reaction temperature under 5° C. The reaction mixture was stirred at 0° C. for 2 h followed by stirring at room temperature overnight. NaBH$_4$ (2.27 g, 60 mmol) was added and the reaction mixture was stirred for an additional hour at room temperature. The reaction mixture was then treated with successive dropwise addition of water (3 mL), 15% NaOH (3 mL), and water (9 mL). The resulting mixture was filtered through Celite, and the remaining solids were washed with EtOAc and methanol. The combined organic portions were evaporated and the resulting crude residue was adsorbed onto SiO$_2$ and purified by flash chromatography (97:3 CH$_2$Cl$_2$-MeOH) to afford 7.63 g (27.7 mmol, 46%) of a red-orange solid as 1e. $^1$H NMR (300 MHz, CDCl$_3$) δ 8.40 (d, J=5.5 Hz, 1H), 8.05 (br s, 1H), 7.96 (d, J=2.75 Hz, 1H), 7.29 (d, J=2.75 Hz, 1H), 6.92 (d, J=9.35 Hz, 1H), 6.75 (m, 2H), 4.68 (s, 2H), 3.07 (d, J=5.23 Hz, 3H).

Step 4

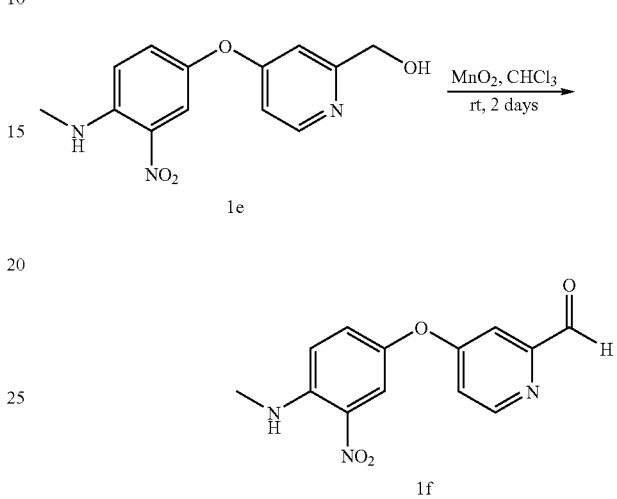

A 100 mL round bottom flask was charged with benzyl alcohol 1e (1.38 g, 5.0 mmol), MnO$_2$ (6.52 g, 75 mmol) and CHCl$_3$ (20 mL). The resulting suspension was stirred at room temperature for 2 days. The reaction mixture was filtered through Celite, and the remaining solids were washed successively with CHCl$_3$ and EtOH. The combined organic portions were evaporated, adsorbed onto silica gel, and purified by flash chromatography (98:2 CH$_2$Cl$_2$/MeOH) to give 790 mg (2.89 mmol, 58%) of an orange solid as 1f. $^1$H NMR (300 MHz, CDCl$_3$) δ 10.01 (s, 1H), 8.64 (d, J=5.5 Hz, 1H), 8.09 (br s, 1H), 7.96 (d, J=2.75 Hz, 1H), 7.37 (d, J=2.48 Hz, 1H), 7.29 (d, J=2.75 Hz, 1H), 7.08 (dd, J=2.47, 5.5 Hz, 1H), 6.94 (d, J=9.35 Hz, 1H), 3.08 (d, J=5.23 Hz, 3H).

Step 5

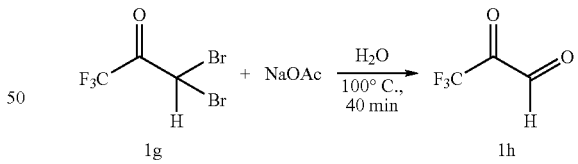

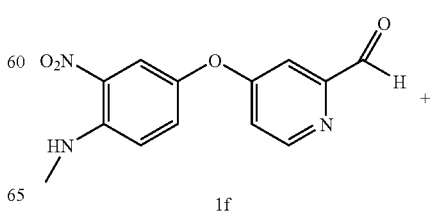

-continued

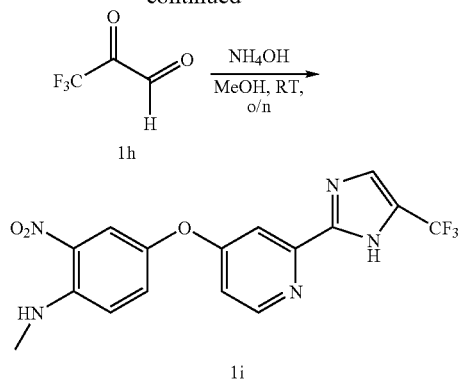

Step 6

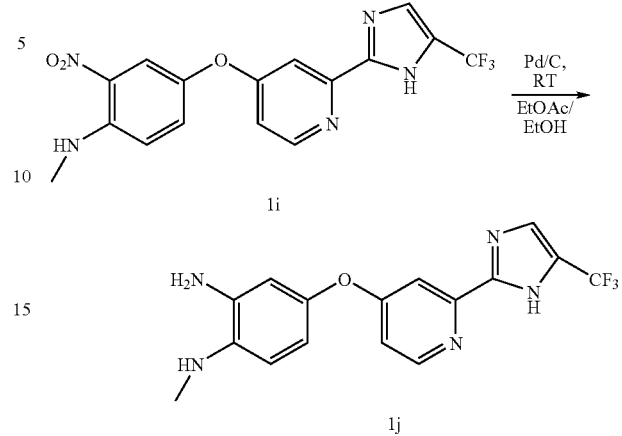

Imidazole ring formation (Baldwin, J. J.; Engelhardt, E. L.; Hirschmann, R; Lundell, G. F.; Ponticello, G. S. J. Med. Chem. 1979, 22, 687): Compound 1g (Lancaster (Windham, N.H.), 25.75 mL, 136.5 mmol) was added to a solution of NaOAc (sodium acetate, 22.4 g, 273 mmol) in $H_2O$ (60 mL) and the resulting solution heated to 100° C. for 40 min. After cooling to room temperature, the solution of 1 h was added to a suspension of 1f (25 g, 91 mmol) in $NH_4OH$ (150 mL) and methanol (450 mL). The resulting mixture was stirred at room temperature overnight. TLC (thin layer chromatography, 95:5 $CH_2Cl_2$/MeOH) showed complete consumption of 1f. The crude product was concentrated into an aqueous slurry, and partitioned with saturated $Na_2CO_3$ and $CH_2Cl_2$. The aqueous phase was extracted three times with $CH_2Cl_2$, and the combined organics washed with brine, then dried ($MgSO_4$), and concentrated to give 31.6 g of 1i (83 mmol) as an orange solid (91% yield).

A slurry of nitroaniline 1i (45.76 g, 120 mmol) in MeOH (220 mL) and EtOAc (200 mL) was sparged with $N_2$ for 20 min, and then charged with a suspension of 10% Pd/C (12.77 g, 120 mmol) in MeOH (60 mL). The reaction was purged with $H_2$ and maintained under a $H_2$ atmosphere for 2 days. The reaction was filtered through a pad of Celite and the collected solids were washed successively with MeOH and EtOAc. The combined organic filtrates were evaporated, the resulting solid was azeotroped with $CH_2Cl_2$ and then dried overnight under vacuum to give 40.17 g (115 mmol) of 1j as a tan powder (96% yield). LCMS m/z 336.1 ($MH^+$), $t_R$=1.81 min.

Step 7

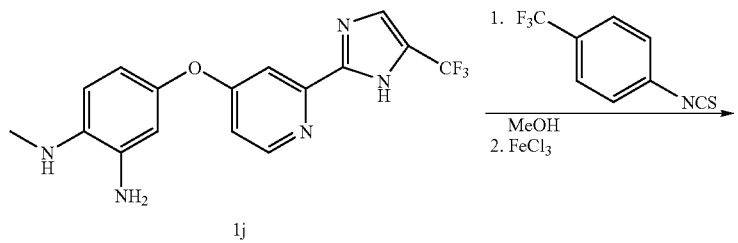

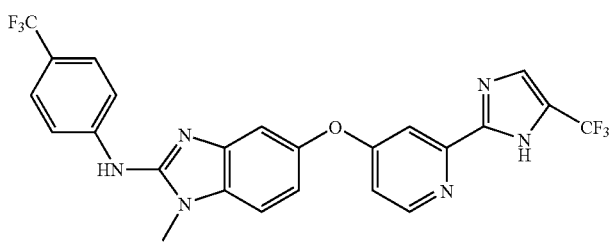

4-Trifluoromethylphenyl isothiocyanate (23.37 g, 115 mmol) was added to a stirring solution of diamine 1j (40.17 g, 115 mmol) in MeOH (460 mL) at room temperature. The reaction was maintained at room temperature for 16 h. After the reaction was judged complete, a solution of $FeCl_3$ (20.52 g, 126.5 mmol) in MeOH (50 mL) was added to the reaction and the resulting mixture was stirred at room temperature overnight. The crude reaction mixture was added to a 3 L separatory funnel containing EtOAc (750 mL) and water (750 mL). The layers were separated, and the aqueous phase was extracted with EtOAc (aqueous phase saved). The organic layers were combined, washed with saturated aqueous $Na_2CO_3$ solution, water, and brine, then dried ($MgSO_4$), and concentrated. The saved aqueous phase was made basic (pH=10) by addition of saturated aqueous $Na_2CO_3$ solution and the resulting slurry was added to a 3 L separatory funnel containing EtOAc (500 mL). The mixture was agitated and the resulting emulsion was filtered through filter paper, and the layers were then separated and the aqueous phase was extracted with EtOAc (2×500 mL). The organic layers were combined, washed with brine, then dried ($MgSO_4$), added to previously extracted material and concentrated. The combined product was triturated with $CH_2Cl_2$ (500 mL), adsorbed onto $SiO_2$ and purified by flash chromatography. A final trituration of material with $CH_2Cl_2$ produced {1-methyl-5-[2-(5-trifluoromethyl-1H-imidazol-2-yl)-pyridin-4-yloxy]-1H-benzoimidazol-2-yl}-(4-trifluoromethyl-phenyl)-amine as a pure, white solid. LCMS (liquid chromatography mass spectroscopy) m/z 519.1 (MH+); $^1$H NMR (300 MHz, $CDCl_3$) δ 8.44 (d, J=5.5 Hz, 1H), 7.75 (d, J=8.8 Hz, 2H), 7.61 (dd, J=2.2, 8.5 Hz, 1H), 7.59 (d, J=8.8 Hz, 2H), 7.56 (d, J=2.5 Hz, 1H), 7.38 (app d, J=8.5 Hz, 1H), 7.23 (d, J=1.9 Hz, 1H), 6.96 (dd, J=2.2, 8.5 Hz, 1H), 6.93 (dd, J=2.5, 5.5 Hz, 1H), 3.76 (s, 3H); LCMS m/z=519.0, $t_R$=2.57 min (MHe); Anal. calc'd for $C_{24}H_{16}F_6N_6O$: C, 55.6, H, 3.11, N, 16.21. Found: C, 55.81; H, 3.43; N, 16.42. mp: 217-220° C. (dec.).

The following example describes methods for preparing disubstituted imidazole compounds.

Example 1a

Intermediate 1i$^2$ was synthesized following step 5 of Example 1 using 3,3,3-trifluoro-1-phenylpropane-1,2-dione dydrate as shown below (MeOH=methanol, RT=room temperature, o/n=overnight, min=minutes):

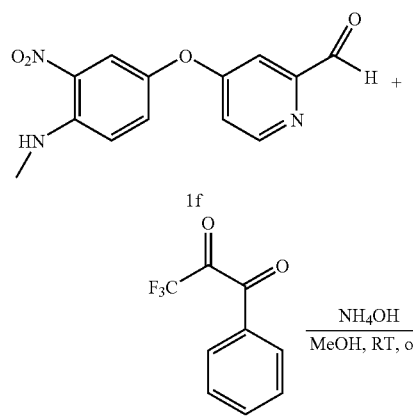

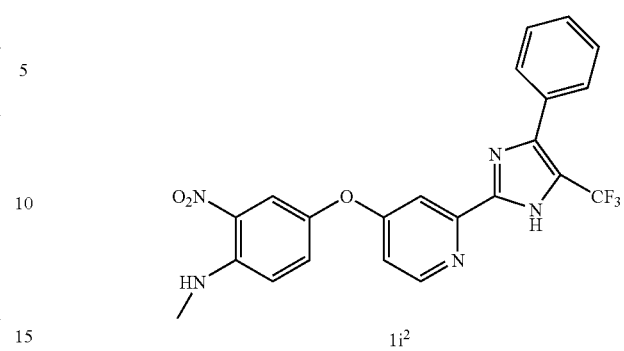

Intermediate 1i$^3$ was synthesized following step 5 of Example 1 using 1-phenyl-1,2-propanedione instead of 1h as shown below:

Intermediate 1i$^4$ was synthesized following step 5 of Example 1 using 1-(3-trifluoromethylphenyl)-1,2-propanedione or 1-(4-trifluoromethylphenyl)-1,2-propanedione as shown below:

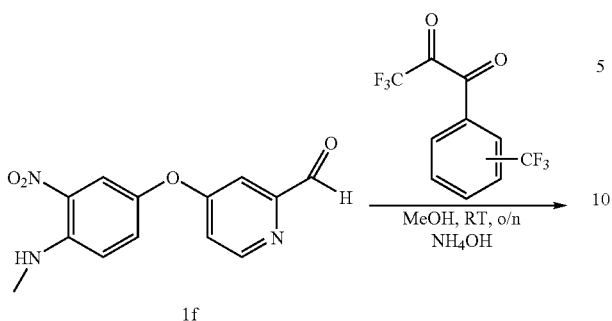

1f

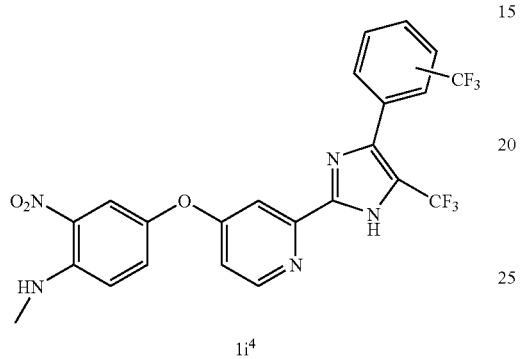

1i⁴

Intermediate 1i⁵ was synthesized following step 5 of Example 1, coupled with procedures in U.S. Pat. No. 5,374,615, using ethyl (2Z)-4,4,4-trifluoro-2-(hydroxyimino)-3-oxobutanoate made from ethyl 4,4,4-trifluoro-3-oxobutanoate as shown below (AcOH=acetic acid, NaOAc=sodium acetate, NMA=N-methyl acetamide):

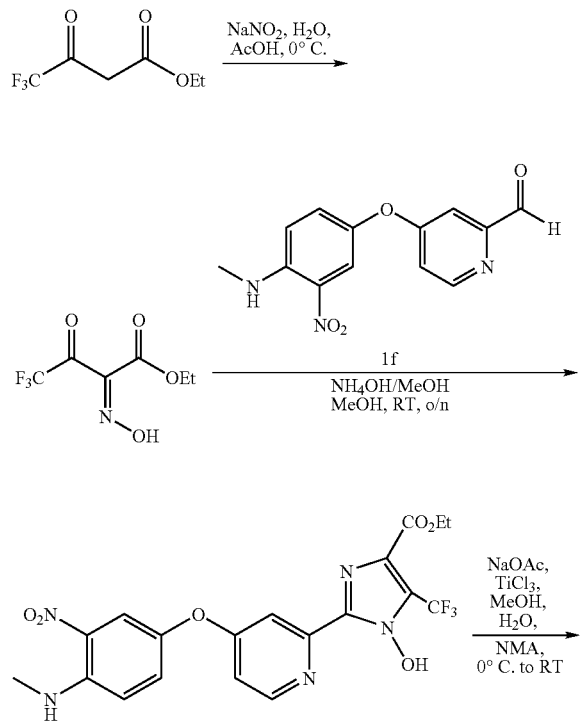

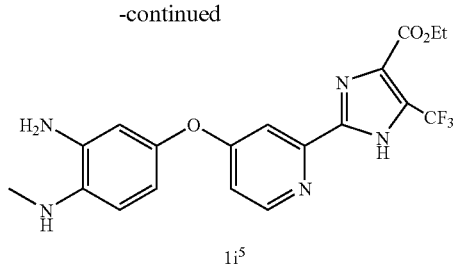

1i⁵

Example 2

Preparation of (2-Fluoro-5-pyridin-3-yl-phenyl)-{1-methyl-5-[2-(5-trifluoromethyl-1H-imidazol-2-yl)-pyridin-4-yloxy]-1H-benzoimidazol-2-yl}-amine

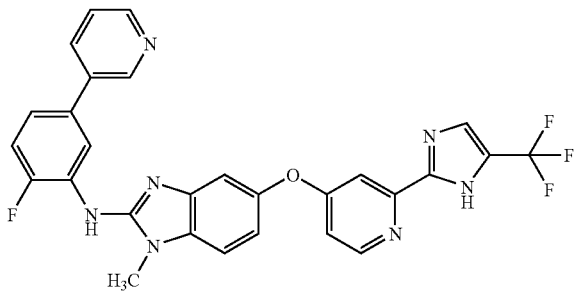

(2-Fluoro-5-pyridin-3-yl-phenyl)-{1-methyl-5-[2-(5-trifluoromethyl-1H-imidazol-2-yl)-pyridin-4-yloxy]-1H-benzoimidazol-2-yl}-amine was synthesized as described above in Step 7 of Example 1 using 3-(4-Fluoro-3-isothiocyanatophenyl)-pyridine. LCMS m/z 546.1 (MH⁺), $R_t$ 1.82 min.

Example 3

Preparation of (2-Fluoro-5-pyridin-4-yl-phenyl)-{1-methyl-5-[2-(5-trifluoromethyl-1H-imidazol-2-yl)-pyridin-4-yloxy]-1H-benzoimidazol-2-yl}-amine

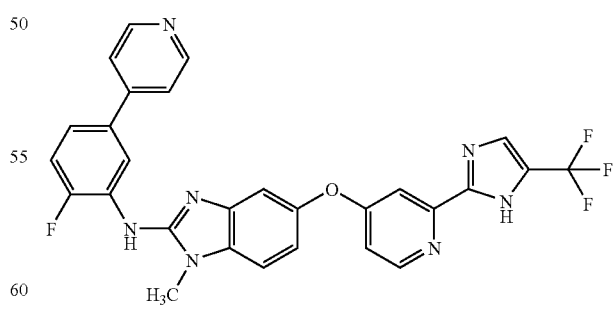

(2-Fluoro-5-pyridin-4-yl-phenyl)-{1-methyl-5-[2-(5-trifluoromethyl-1H-imidazol-2-yl)-pyridin-4-yloxy]-1H-benzoimidazol-2-yl}-amine was synthesized as described above in Step 7 of Example 1 using 4-(4-Fluoro-3-isothiocyanatophenyl)-pyridine. LCMS m/z 546.5 (MH⁺), $R_t$ 1.83 min.

Example 4

Preparation of (4-tert-Butyl-phenyl)-{1-methyl-5-[2-(5-trifluoromethyl-1H-imidazol-2-yl)-pyridin-4-yloxy]-1H-benzoimidazol-2-yl}-amine

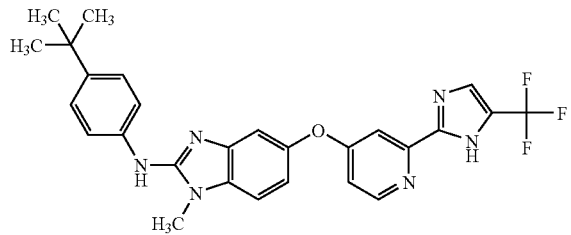

(4-tert-Butyl-phenyl)-{1-methyl-5-[2-(5-trifluoromethyl-1H-imidazol-2-yl)-pyridin-4-yloxy]-1H-benzoimidazol-2-yl}-amine was synthesized as described above in Step 7 of Example 1 using 4-tert-butylphenylisothiocyanate. LCMS m/z 425.4 (MH+), R$_t$ 2.56 min.

Example 5

Preparation of {1-Methyl-5-[2-(5-trifluoromethyl-1H-imidazol-2-yl)-pyridin-4-yloxy]-1H-benzoimidazol-2-yl}-(3-trifluoromethyl-phenyl)-amine

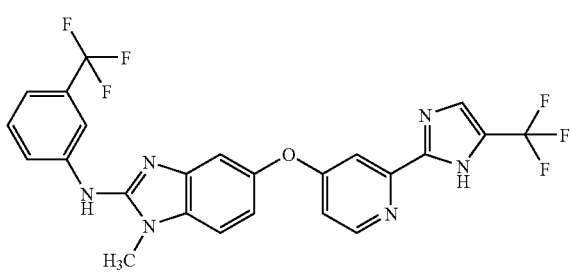

{1-Methyl-5-[2-(5-trifluoromethyl-1H-imidazol-2-yl)-pyridin-4-yloxy]-1H-benzo-imidazol-2-yl}-(3-trifluoromethyl-phenyl)-amine was synthesized as described above in Step 7 of Example 1 using 3-(trifluoromethyl)phenylisothiocyanate. LCMS m/z 519.4 (MH+), R$_t$ 2.36 min.

Example 6

Preparation of (3-Ethyl-phenyl)-{1-methyl-5-[2-(5-trifluoromethyl-1H-imidazol-2-yl)-pyridin-4-yloxy]-1H-benzoimidazol-2-yl}-amine

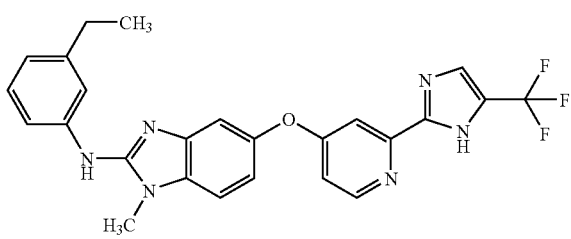

(3-Ethyl-phenyl)-{1-methyl-5-[2-(5-trifluoromethyl-1H-imidazol-2-yl)-pyridin-4-yl-oxy]-1H-benzoimidazol-2-yl}-amine was synthesized as described above in Step 7 of Example 1 using 3-ethyl phenylisothiocyanate. LCMS m/z 479.4 (MH+), R$_t$ 2.32 min.

Example 7

Preparation of (4-Chloro-phenyl)-{1-methyl-5-[2-(5-trifluoromethyl-1H-imidazol-2-yl)-pyridin-4-yloxy]-1H-benzoimidazol-2-yl}-amine

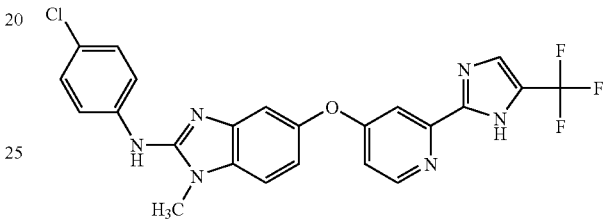

(4-Chloro-phenyl)-{1-methyl-5-[2-(5-trifluoromethyl-1H-imidazol-2-yl)-pyridin-4-yl-oxy]-1H-benzoimidazol-2-yl}-amine was synthesized as described above in Step 7 of Example 1 using 4-chlorophenylisothiocyanate. LCMS m/z 485.4 (MH+), R$_t$, 2.23 min.

Example 8

Preparation of (4-Ethyl-phenyl)-{1-methyl-5-[2-(5-trifluoromethyl-1H-imidazol-2-yl)-pyridin-4-yloxy]-1H-benzoimidazol-2-yl}-amine

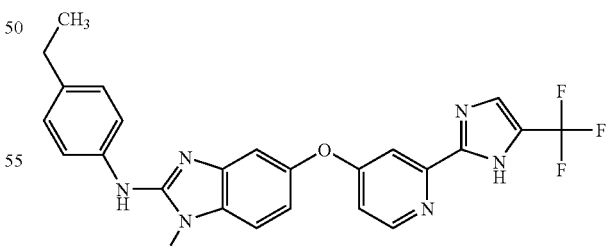

(4-Ethyl-phenyl)-{1-methyl-5-[2-(5-trifluoromethyl-1H-imidazol-2-yl)-pyridin-4-yl-oxy]-1H-benzoimidazol-2-yl}-amine was synthesized as described above in Step 7 of Example 1 using 4-ethylphenylisothiocyanate. LCMS m/z 479.5 (MH+), R$_t$ 2.31 min.

Example 9

Preparation of (4-Chloro-3-trifluoromethyl-phenyl)-{1-methyl-5-[2-(5-trifluoromethyl-1H-imidazol-2-yl)-pyridin-4-yloxy]-1H-benzoimidazol-2-yl}-amine

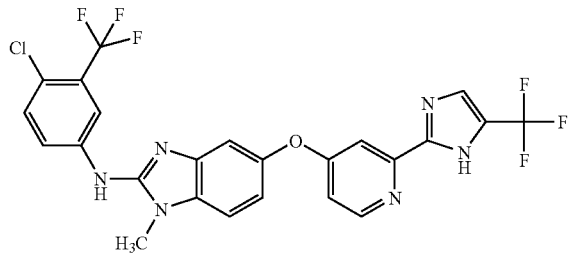

(4-Chloro-3-trifluoromethyl-phenyl)-{1-methyl-5-[2-(5-trifluoromethyl-1H-imidazol-2-yl)-pyridin-4-yloxy]-1H-benzoimidazol-2-yl}-amine was synthesized as described above in Step 7 of Example 1 using 4-chloro-3-(trifluoromethyl)phenylisothiocyanate. LCMS m/z 553.4 (MH$^+$), R$_t$ 2.51 min.

Example 10

Preparation of (4-Fluoro-3-trifluoromethyl-phenyl)-{1-methyl-5-[2-(5-trifluoromethyl-1H-imidazol-2-yl)-pyridin-4-yloxy]-1H-benzoimidazol-2-yl}-amine

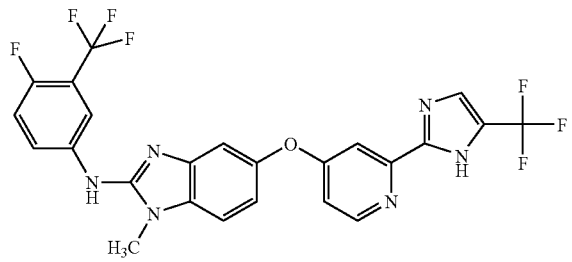

(4-Fluoro-3-trifluoromethyl-phenyl)-{1-methyl-5-[2-(5-trifluoromethyl-1H-imidazol-2-yl)-pyridin-4-yloxy]-1H-benzoimidazol-2-yl}-amine was synthesized as described above in Step 7 of Example 1 using 4-fluoro-3-(trifluoromethyl)phenylisothiocyanate. LCMS m/z 537.4 (MH$^+$), R$_t$ 2.40 min.

Example 11

Preparation of {1-Methyl-5-[2-(5-trifluoromethyl-1H-imidazol-2-yl)-pyridin-4-yloxy]-1H-benzoimidazol-2-yl}-(4-trifluoromethoxy-phenyl)-amine

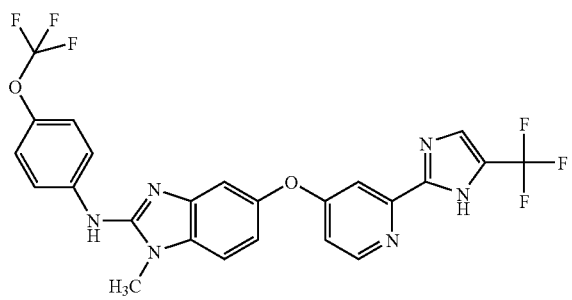

{1-Methyl-5-[2-(5-trifluoromethyl-1H-imidazol-2-yl)-pyridin-4-yloxy]-1H-benzo-imidazol-2-yl}-(4-trifluoromethoxy-phenyl)-amine was synthesized as described above in Step 7 of Example 1 using 4-(trifluoromethoxy) phenylisothiocyanate. LCMS m/z 535.4 (MH$^+$), R$_t$ 2.24 min.

Example 12

Preparation of (2-Fluoro-5-trifluoromethyl-phenyl)-(1-methyl-5-{2-[5-methyl-4-(3-trifluoro-methyl-phenyl)-1H-imidazol-2-yl]-pyridin-4-yloxy}-1H-benzoimidazol-2-yl)-amine

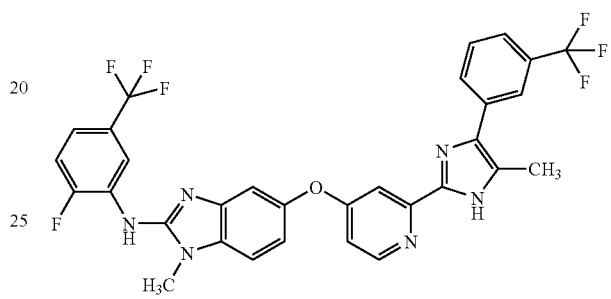

(2-Fluoro-5-trifluoromethyl-phenyl)-(1-methyl-5-{2-[5-methyl-4-(3-trifluoromethyl-phenyl)-1H-imidazol-2-yl]-pyridin-4-yloxy}-1H-benzoimidazol-2-yl)-amine was synthesized using similar procedures as described above in Example 1 using 2-Fluoro-5-(trifluoro-methyl)phenyl isothiocyanate. LCMS m/z 627.5 (MH$^+$), R$_t$ 2.79 min.

Example 13

Preparation of (2-Fluoro-5-trifluoromethyl-phenyl)-(1-methyl-5-{2-[5-methyl-4-(4-trifluoro-methyl-phenyl)-1H-imidazol-2-yl]-pyridin-4-yloxy}-1H-benzoimidazol-2-yl)-amine

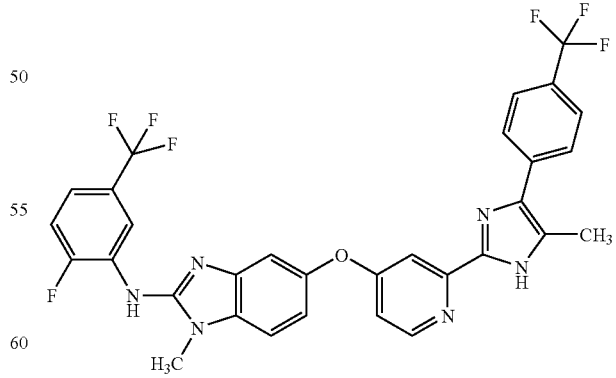

(2-Fluoro-5-trifluoromethyl-phenyl)-(1-methyl-5-{2-[5-methyl-4-(4-trifluoromethyl-phenyl)-1H-imidazol-2-yl]-pyridin-4-yloxy}-1H-benzoimidazol-2-yl)-amine was synthesized using similar procedures as described above in Example 1 using 2-Fluoro-5-(trifluoro-methyl)phenyl isothiocyanate. LCMS m/z 627.5 (MH$^+$), R$_t$ 2.79 min.

Example 14

Preparation of 2-{4-[2-(2-Fluoro-5-trifluoromethyl-phenylamino)-1-methyl-1H-benzoimidazol-5-yloxy]-pyridin-2-yl}-5-trifluoromethyl-1H-imidazole-4-carboxylic acid ethyl ester

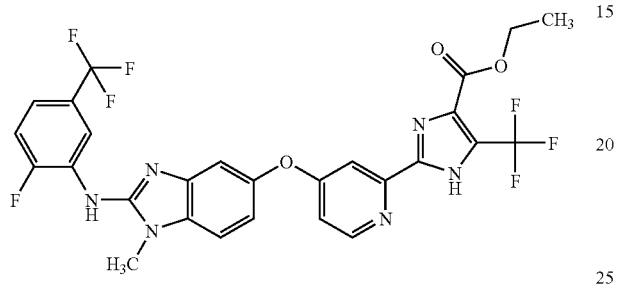

2-{4-[2-(2-Fluoro-5-trifluoromethyl-phenylamino)-1-methyl-1H-benzoimidazol-5-yl-oxy]-pyridin-2-yl}-5-trifluoromethyl-1H-imidazole-4-carboxylic acid ethyl ester was synthesized using similar procedures as described above in Example 1 using 2-Fluoro-5-(trifluoro-methyl)phenyl isothiocyanate. LCMS m/z 609.5 (MH$^+$).

Example 15

Preparation of (2-{4-[2-(2-Fluoro-5-trifluoromethyl-phenylamino)-1-methyl-1H-benzoimidazol-5-yloxy]-pyridin-2-yl}-5-trifluoromethyl-1H-imidazol-4-yl)-methanol

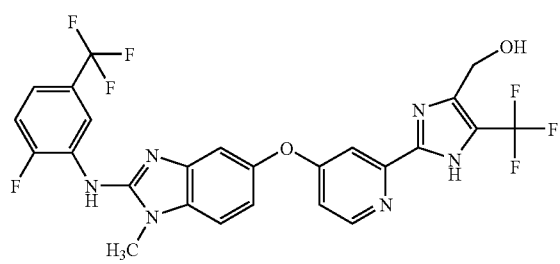

Red-Al (sodium bis(2-methoxyethoxy)aluminium hydride, 65% wt in toluene, 0.1 mL) was added dropwise to a solution of 2-{4-[2-(2-fluoro-5-trifluoromethyl-phenylamino)-1-methyl-1H-benzoimidazol-5-yloxy]-pyridin-2-yl}-5-trifluoromethyl-1H-imidazole-4-carboxylic acid ethyl ester (0.0104 g, 0.017 mmol) in toluene. Effervescence was observed and after 20 min, the reaction was quenched with H$_2$O, NaOH and extracted with EtOAc. The organic layer was washed with H$_2$O, dried over Na$_2$SO$_4$, filtered and concentrated to give 5.9 mg of crude (2-{4-[2-(2-fluoro-5-trifluoromethyl-phenylamino)-1-methyl-1H-benzoimidazol-5-yloxy]-pyridin-2-yl}-5-trifluoromethyl-1H-imidazol-4-yl)-methanol which was further purified by RP HPLC (reverse phase HPLC) to give 1.1 mg of the pure compound (98% purity). LCMS m/z 567.1 (MH$^+$), R$_t$ 2.40 min.

Example 16

Preparation of 2-{4-[1-Methyl-2-(4-trifluoromethyl-phenylamino)-1H-benzoimidazol-5-yloxy]-pyridin-2-yl}-3H-imidazole-4-carbonitrile

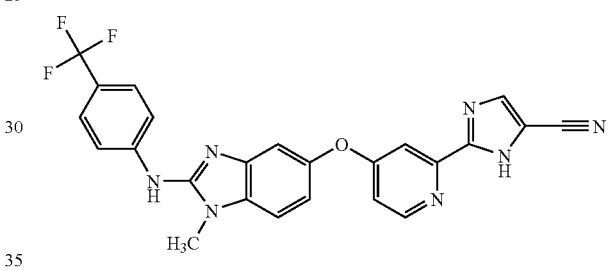

A slurry of {1-methyl-5-[2-(5-trifluoromethyl-1H-imidazol-2-yl)-pyridin-4-yloxy]-1H-benzoimidazol-2-yl}-(4-trifluoromethyl-phenyl)-amine was prepared according to Example 1 (1.83 g, 3.4 mmol) and 28% NH$_4$OH (23 mL) in MeOH (10 mL) was sealed in a tube and heated to 140° C. for 3 h. The reaction was monitored by LCMS. Then, the crude reaction mixture was added to a separatory funnel and partitioned with EtOAc (50) and water (50 mL). The layers were separated, and the aqueous phase was extracted with EtOAc (2×50 mL). The organic layers were combined, washed with brine, then dried (MgSO$_4$), and concentrated. The crude product was adsorbed onto SiO$_2$ and purified by flash chromatography to give 2-{4-[1-methyl-2-(4-trifluoromethyl-phenylamino)-1H-benzoimidazol-5-yloxy]-pyridin-2-yl}-3H-imidazole-4-carbonitrile as a white solid. LCMS m/z 476.1 (MH$^+$)

EXAMPLES 17-59b

The compounds shown in the following Table 1 (Examples 17-59b) were prepared following the procedures described for Examples 1-16. Various starting materials used in the synthesis of the compounds will be apparent to one of skill in the art (e.g. Tordeux, M.; Langlois, B.; Wakselman, C. *J. Chem. Soc. Perkin Trans* 1 1990, 2293).

TABLE 1

| Example | Structure | Name | MH+ |
|---|---|---|---|
| 17 | 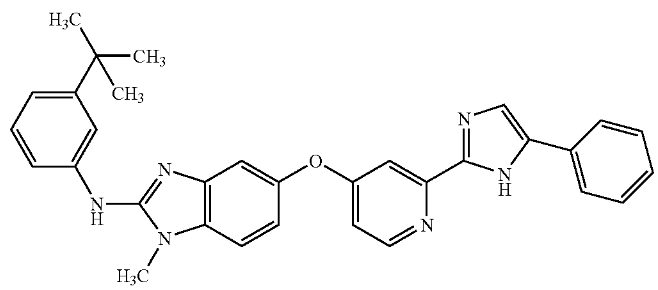 | (3-tert-Butyl-phenyl)-{1-methyl-5-[2-(5-phenyl-1H-imidazol-2-yl)-pyridin-4-yloxy]-1H-benzo-imidazol-2-yl}-amine | 515.4 |
| 18 | 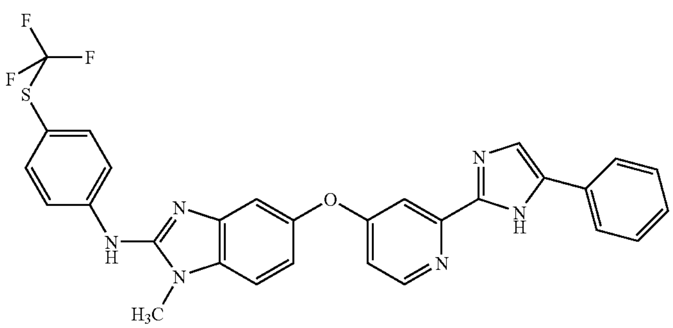 | {1-Methyl-5-[2-(5-phenyl-1H-imidazol-2-yl)-pyridin-4-yloxy]-1H-benzoimidazol-2-yl}-(4-trifluoromethylsulfanyl-phenyl)-amine | 559.3 |
| 19 | 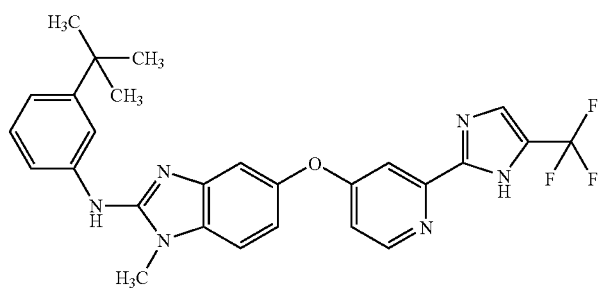 | (3-tert-Butyl-phenyl)-{1-methyl-5-[2-(5-trifluoromethyl-1H-imidazol-2-yl)-pyridin-4-yloxy]-1H-benzo-imidazol-2-yl}-amine | 507.1 |
| 20 | 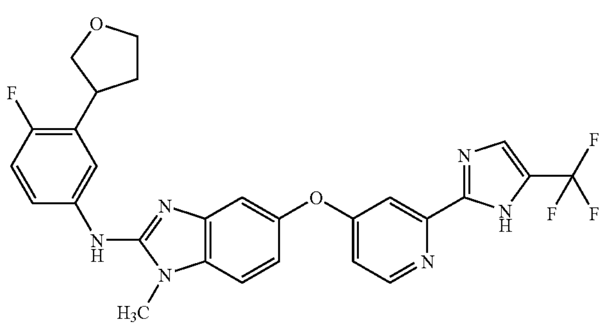 | [4-Fluoro-3-(tetrahydro-furan-3-yl)-phenyl]-{1-methyl-5-[2-(5-trifluoromethyl-1H-imidazol-2-yl)-pyridin-4-yloxy]-1H-benzoimidazol-2-yl}-amine | 539.3 |
| 21 | 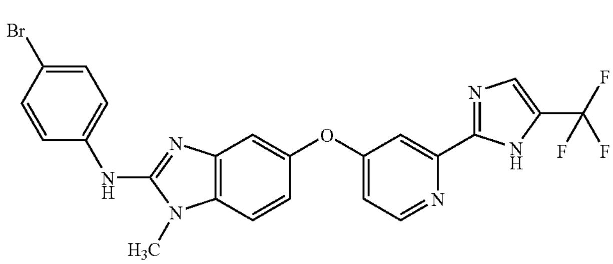 | (4-Bromo-phenyl)-{1-methyl-5-[2-(5-trifluoromethyl-1H-imidazol-2-yl)-pyridin-4-yloxy]-1H-benzoimidazol-2-yl}-amine | 529.1 |

TABLE 1-continued

| Example | Structure | Name | MH+ |
|---|---|---|---|
| 22 | 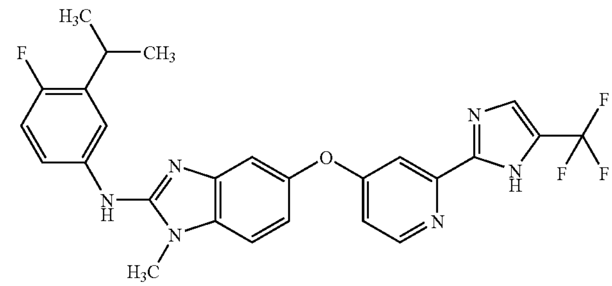 | (4-Fluoro-3-isopropyl-phenyl)-{1-methyl-5-[2-(5-trifluoromethyl-1H-imidazol-2-yl)-pyridin-4-yloxy]-1H-benzoimidazol-2-yl}-amine | 511.3 |
| 23 | 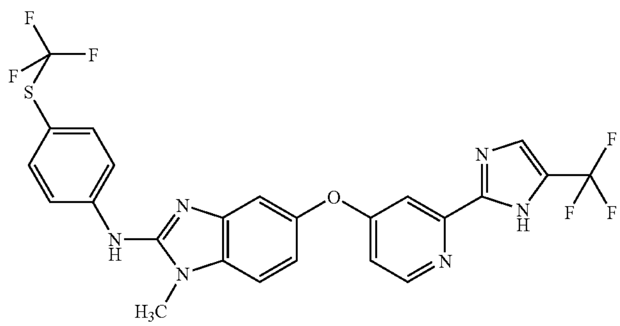 | {1-Methyl-5-[2-(5-trifluoromethyl-1H-imidazol-2-yl)-pyridin-4-yloxy]-1H-benzoimidazol-2-yl}-(4-trifluoromethylsulfanyl-phenyl)-amine | 551.2 |
| 24 | 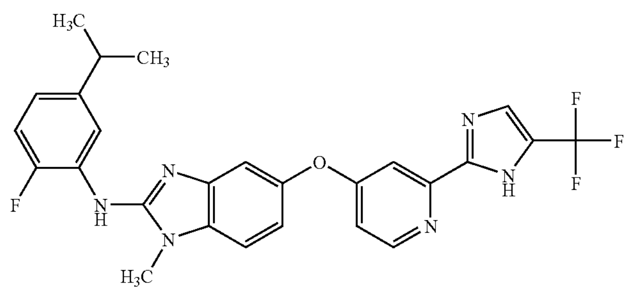 | (2-Fluoro-5-isopropyl-phenyl)-{1-methyl-5-[2-(5-trifluoromethyl-1H-imidazol-2-yl)-pyridin-4-yloxy]-1H-benzoimidazol-2-yl}-amine | 511.1 |
| 25 | 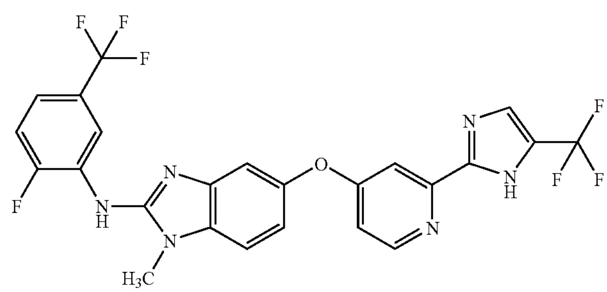 | (2-Fluoro-5-trifluoromethyl-phenyl)-{1-methyl-5-[2-(5-trifluoromethyl-1H-imidazol-2-yl)-pyridin-4-yloxy]-1H-benzoimidazol-2-yl}-amine | 537.0 |
| 26 | 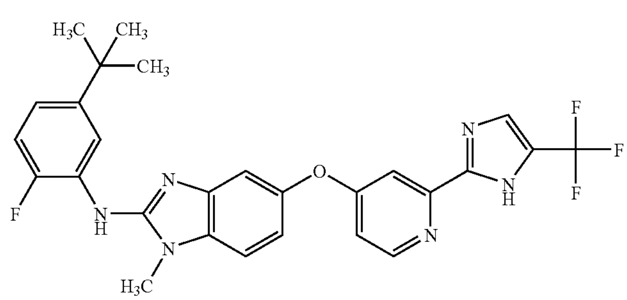 | (5-tert-Butyl-2-fluoro-phenyl)-{1-methyl-5-[2-(5-trifluoromethyl-1H-imidazol-2-yl)-pyridin-4-yloxy]-1H-benzoimidazol-2-yl}-amine | 525.1 |

TABLE 1-continued

| Example | Structure | Name | MH+ |
|---|---|---|---|
| 27 | 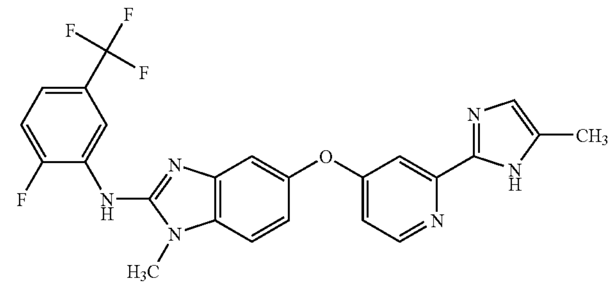 | (2-Fluoro-5-trifluoromethyl-phenyl)-{1-methyl-5-[2-(5-methyl-1H-imidazol-2-yl)-pyridin-4-yl-oxy]-1H-benzoimidazol-2-yl}-amine | 483.1 |
| 28 | 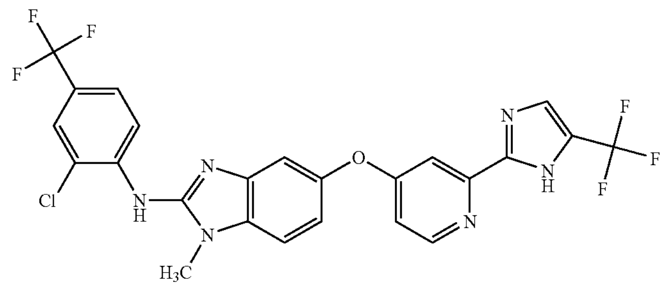 | (2-Chloro-4-trifluoromethyl-phenyl)-{1-methyl-5-[2-(5-tri-fluoromethyl-1H-imidazol-2-yl)-pyridin-4-yloxy]-1H-benzo-imidazol-2-yl}-amine | 553.0 |
| 29 | 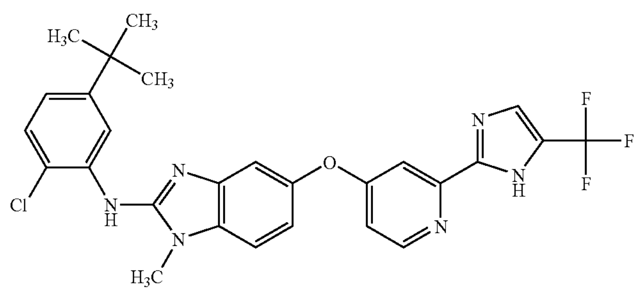 | (5-tert-Butyl-2-chloro-phenyl)-{1-methyl-5-[2-(5-trifluoromethyl-1H-imidazol-2-yl)-pyridin-4-yloxy]-1H-benzoimidazol-2-yl}-amine | 541.1 |
| 30 | 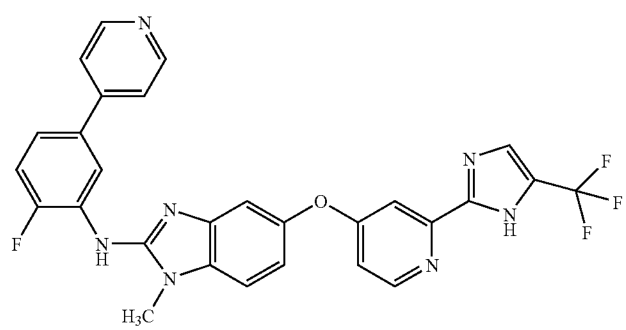 | (2-Fluoro-5-pyridin-4-yl-phenyl)-{1-methyl-5-[2-(5-trifluoromethyl-1H-imidazol-2-yl)-pyridin-4-yl-oxy]-1H-benzoimidazol-2-yl}-amine | 546.5 |
| 31 | 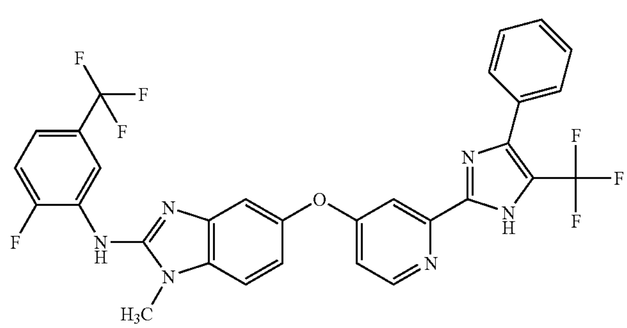 | (2-Fluoro-5-trifluoromethyl-phenyl)-{1-methyl-5-[2-(4-phenyl-5-trifluoromethyl-1H-imidazol-2-yl)-pyridin-4-yloxy]-1H-benzo-imidazol-2-yl}-amine | 613.1 |

TABLE 1-continued

| Example | Structure | Name | MH+ |
|---|---|---|---|
| 32 | 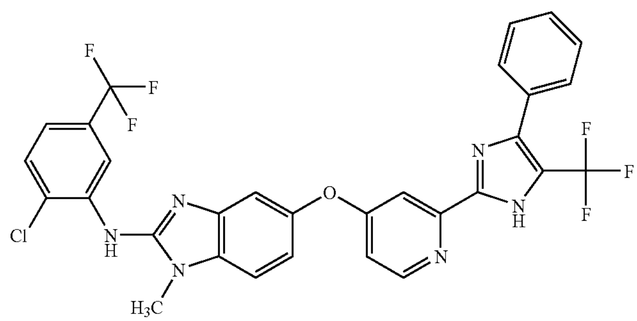 | (2-Chloro-5-trifluoromethyl-phenyl)-{1-methyl-5-[2-(4-phenyl-5-trifluoromethyl-1H-imidazol-2-yl)-pyridin-4-yloxy]-1H-benzo-imidazol-2-yl}-amine | 629.0 |
| 33 | 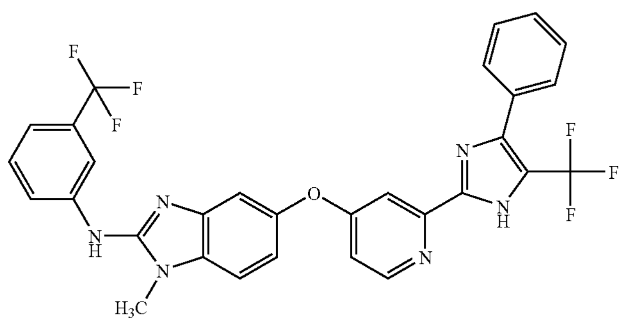 | {1-Methyl-5-[2-(4-phenyl-5-trifluoromethyl-1H-imidazol-2-yl)-pyridin-4-yloxy]-1H-benzo-imidazol-2-yl}-(3-trifluoromethyl-phenyl)-amine | 595.1 |
| 34 | 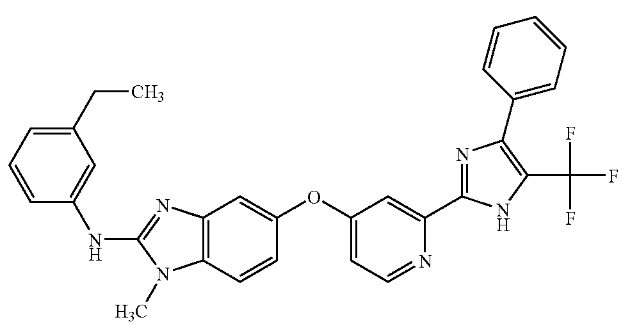 | (3-Ethyl-phenyl)-{1-methyl-5-[2-(4-phenyl-5-trifluoromethyl-1H-imidazol-2-yl)-pyridin-4-yloxy]-1H-benzoimidazol-2-yl}-amine | 555.1 |
| 35 | 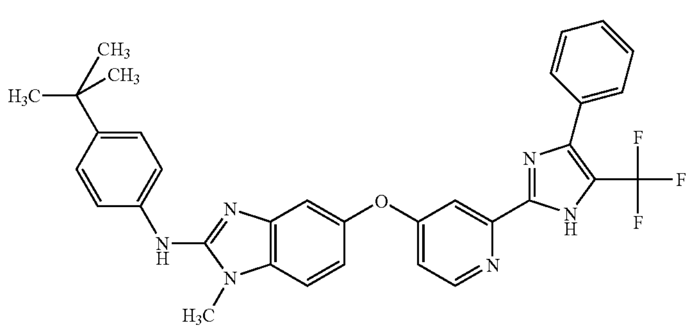 | (4-tert-Butyl-phenyl)-{1-methyl-5-[2-(4-phenyl-5-trifluoromethyl-1H-imidazol-2-yl)-pyridin-4-yloxy]-1H-benzoimidazol-2-yl}-amine | 583.2 |

TABLE 1-continued

| Example | Structure | Name | MH+ |
|---|---|---|---|
| 36 | 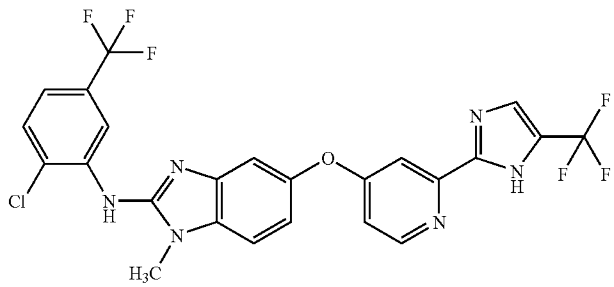 | (2-Chloro-5-trifluoromethyl-phenyl)-{1-methyl-5-[2-(5-trifluoromethyl-1H-imidazol-2-yl)-pyridin-4-yloxy]-1H-benzoimidazol-2-yl}-amine | 553.1 |
| 37 | 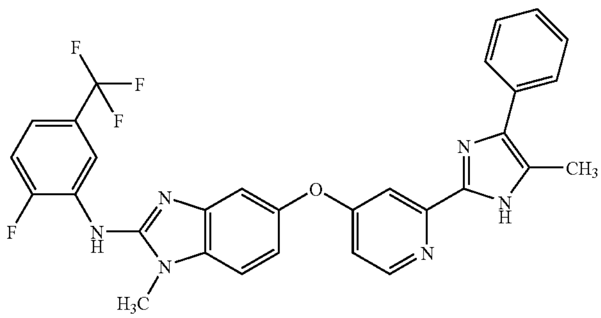 | (2-Fluoro-5-trifluoromethyl-phenyl)-{1-methyl-5-[2-(5-methyl-4-phenyl-1H-imidazol-2-yl)-pyridin-4-yloxy]-1H-benzoimidazol-2-yl}-amine | 559.1 |
| 38 | 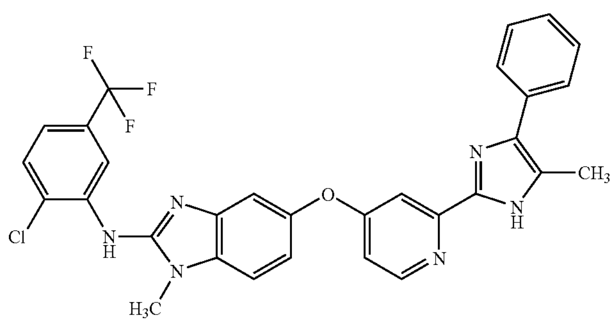 | (2-Chloro-5-trifluoromethyl-phenyl)-{1-methyl-5-[2-(5-methyl-4-phenyl-1H-imidazol-2-yl)-pyridin-4-yloxy]-1H-benzoimidazol-2-yl}-amine | 575.1 |
| 39 | 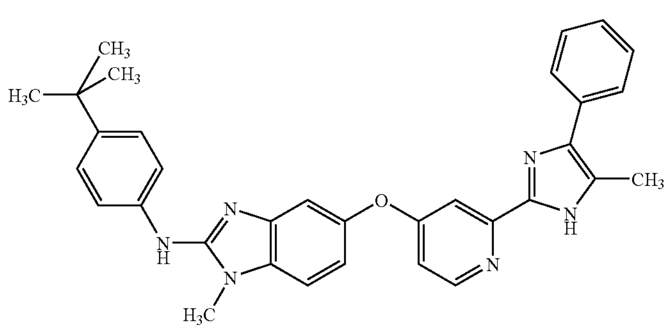 | (4-tert-Butyl-phenyl)-{1-methyl-5-[2-(5-methyl-4-phenyl-1H-imidazol-2-yl)-pyridin-4-yloxy]-1H-benzoimidazol-2-yl}-amine | 529.3 |

TABLE 1-continued

| Example | Structure | Name | MH+ |
|---|---|---|---|
| 40 | 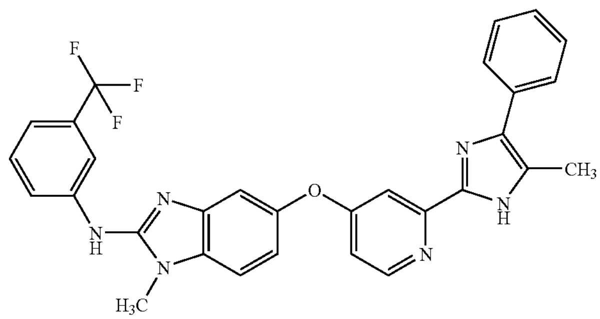 | {1-Methyl-5-[2-(5-methyl-4-phenyl-1H-imidazol-2-yl)-pyridin-4-yloxy]-1H-benzoimidazol-2-yl}-(3-trifluoromethyl-phenyl)-amine | 541.2 |
| 41 | 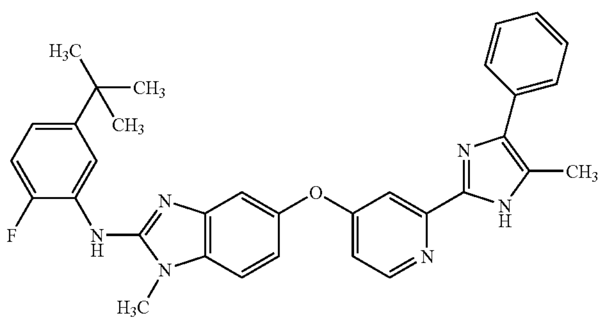 | (5-tert-Butyl-2-fluoro-phenyl)-{1-methyl-5-[2-(5-methyl-4-phenyl-1H-imidazol-2-yl)-pyridin-4-yloxy]-1H-benzoimidazol-2-yl}-amine | 547.2 |
| 42 | 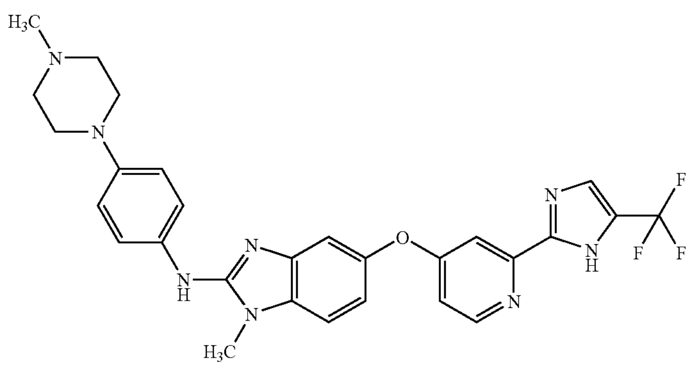 | [4-(4-Methyl-piperazin-1-yl)-phenyl]-{1-methyl-5-[2-(5-trifluoromethyl-1H-imidazol-2-yl)-pyridin-4-yloxy]-1H-benzoimidazol-2-yl}-amine | 549.2 |
| 43 | 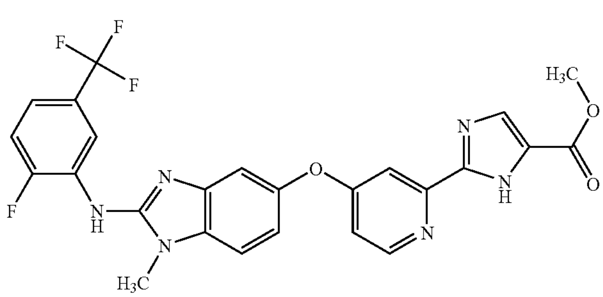 | 2-{4-[2-(2-Fluoro-5-trifluoromethyl-phenylamino)-1-methyl-1H-benzoimidazol-5-yloxy]-pyridin-2-yl}-3H-imidazole-4-carboxylic acid methyl ester | 527.1 |

TABLE 1-continued

| Example | Structure | Name | MH+ |
|---|---|---|---|
| 44 | 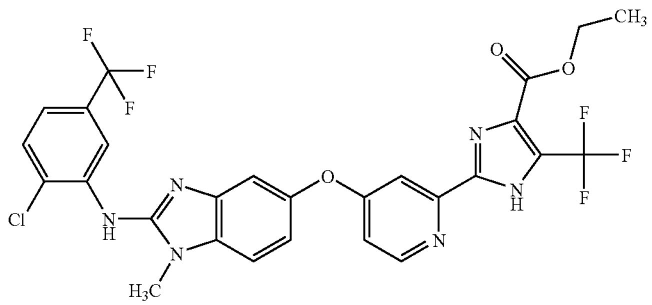 | 2-{4-[2-(2-Chloro-5-trifluoro-methyl-phenylamino)-1-methyl-1H-benzoimidazol-5-yloxy]-pyridin-2-yl}-5-trifluoromethyl-1H-imidazole-4-carboxylic acid ethyl ester | 625.0 |
| 45 | 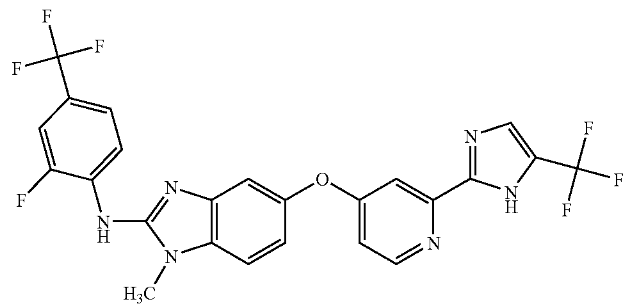 | (2-Fluoro-4-trifluoromethyl-phenyl)-{1-methyl-5-[2-(5-trifluoromethyl-1H-imidazol-2-yl)-pyridin-4-yloxy]-1H-benzoimidazol-2-yl}-amine | 537.1 |
| 46 | 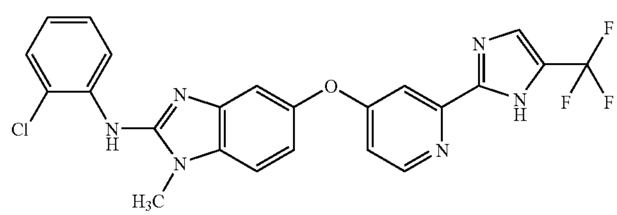 | (2-Chloro-phenyl)-{1-methyl-5-[2-(5-trifluoromethyl-1H-imidazol-2-yl)-pyridin-4-yloxy]-1H-benzoimidazol-2-yl}-amine | 485.1 |
| 47 | 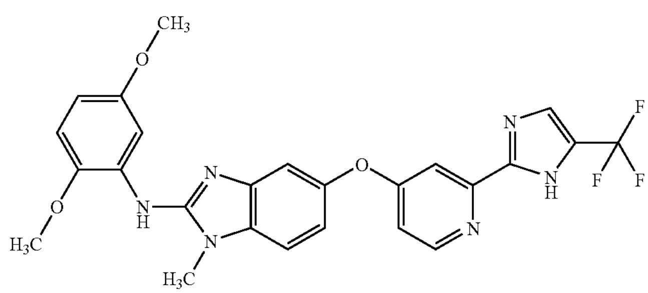 | (2,5-Dimethoxy-phenyl)-{1-methyl-5-[2-(5-trifluoromethyl-1H-imidazol-2-yl)-pyridin-4-yloxy]-1H-benzoimidazol-2-yl}-amine | 511.1 |
| 48 | 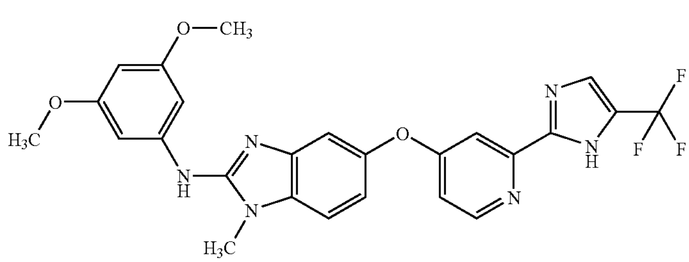 | (3,5-Dimethoxy-phenyl)-{1-methyl-5-[2-(5-trifluoromethyl-1H-imidazol-2-yl)-pyridin-4-yloxy]-1H-benzoimidazol-2-yl}-amine | 511.2 |

TABLE 1-continued

| Example | Structure | Name | MH+ |
|---|---|---|---|
| 49 | 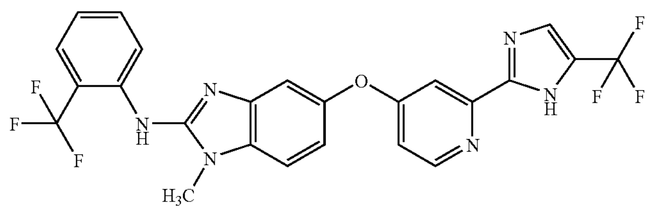 | {1-Methyl-5-[2-(5-trifluoromethyl-1H-imidazol-2-yl)-pyridin-4-yl-oxy]-1H-benzoimidazol-2-yl}-(2-trifluoromethyl-phenyl)-amine | 519.1 |
| 50 | 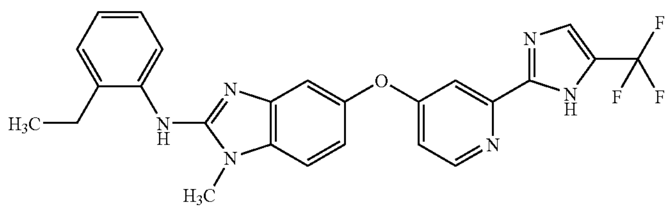 | (2-Ethyl-phenyl)-{1-methyl-5-[2-(5-trifluoromethyl-1H-imidazol-2-yl)-pyridin-4-yloxy]-1H-benzo-imidazol-2-yl}-amine | 479.2 |
| 51 | 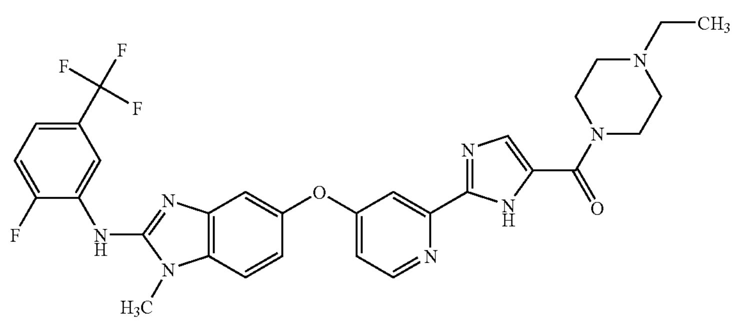 | (4-Ethyl-piperazin-1-yl)-(2-{4-[2-(2-fluoro-5-trifluoromethyl-phenylamino)-1-methyl-1H-benzo-imidazol-5-yloxy]-pyridin-2-yl}-3H-imidazol-4-yl)-methanone | 609.2 |
| 52 | 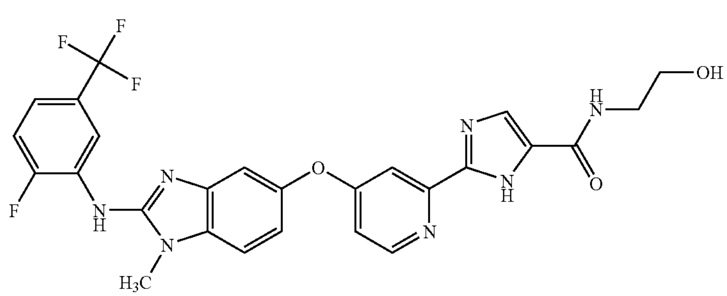 | 2-{4-[2-(2-Fluoro-5-trifluoro-methyl-phenylamino)-1-methyl-1H-benzoimidazol-5-yloxy]-pyridin-2-yl}-3H-imidazole-4-carboxylic acid (2-hydroxy-ethyl)-amide | 556.1 |
| 53 | 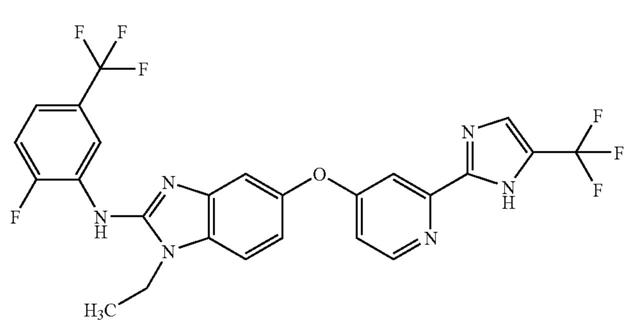 | {1-Ethyl-5-[2-(5-trifluoromethyl-1H-imidazol-2-yl)-pyridin-4-yl-oxy]-1H-benzoimidazol-2-yl}-(2-fluoro-5-trifluoromethyl-phenyl)-amine | 551.1 |

TABLE 1-continued

| Example | Structure | Name | MH+ |
|---|---|---|---|
| 54 | 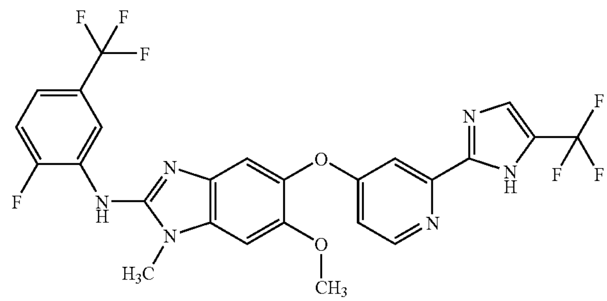 | (2-Fluoro-5-trifluoromethyl-phenyl)-{6-methoxy-1-methyl-5-[2-(5-trifluoromethyl-1H-imidazol-2-yl)-pyridin-4-yloxy]-1H-benzo-imidazol-2-yl}-amine | 567.4 |
| 55 | 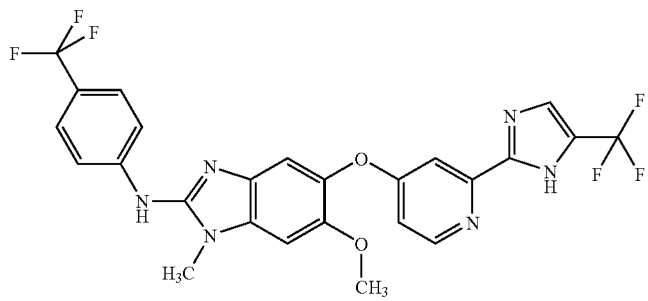 | {6-Methoxy-1-methyl-5-[2-(5-tri-fluoromethyl-1H-imidazol-2-yl)-pyridin-4-yloxy]-1H-benzo-imidazol-2-yl}-(4-trifluoromethyl-phenyl)-amine | 549.4 |
| 56 | 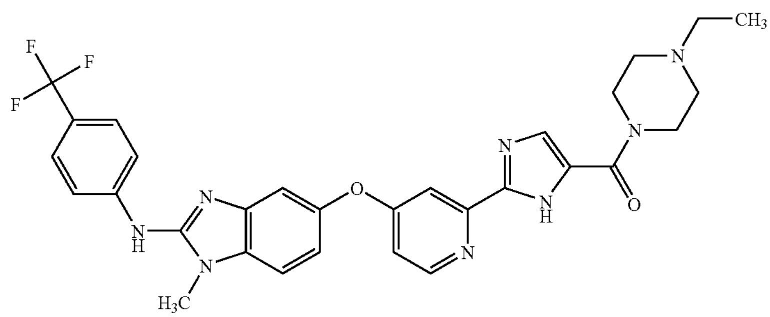 | (4-Ethyl-piperazin-1-yl)-(2-{4-[1-methyl-2-(4-trifluoromethyl-phenylamino)-1H-benzoimidazol-5-yloxy]-pyridin-2-yl}-3H-imidazol-4-yl)-methanone | 591.2 |
| 57 | 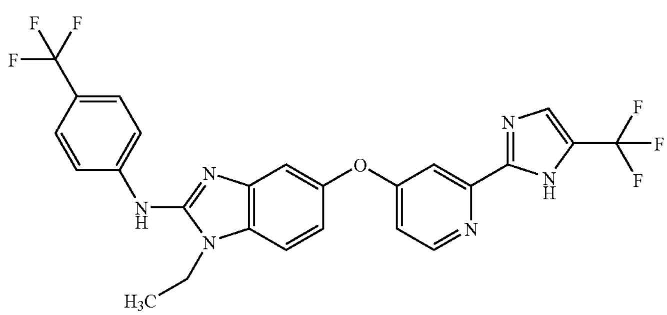 | {1-Ethyl-5-[2-(5-trifluoromethyl-1H-imidazol-2-yl)-pyridin-4-yl-oxy]-1H-benzoimidazol-2-yl}-(4-trifluoromethyl-phenyl)-amine | 533.1 |
| 58 | 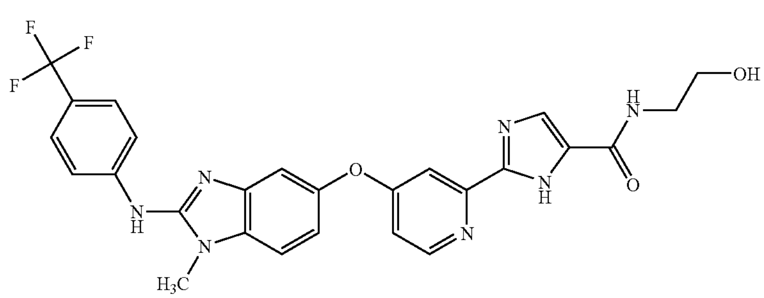 | 2-{4-[1-Methyl-2-(4-trifluoro-methyl-phenylamino)-1H-benzo-imidazol-5-yloxy]-pyridin-2-yl}-3H-imidazole-4-carboxylic acid (2-hydroxy-ethyl)-amide | 538.1 |

TABLE 1-continued

| Example | Structure | Name | MH+ |
|---|---|---|---|
| 59 | 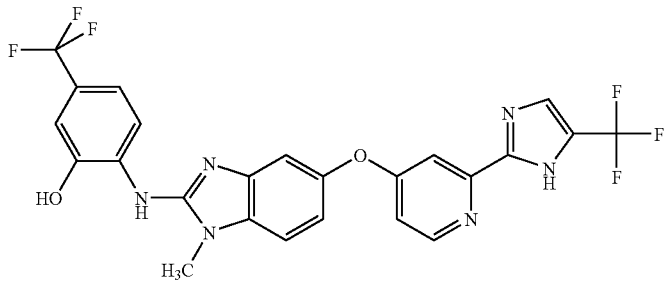 | 2-{1-Methyl-5-[2-(5-trifluoro-methyl-1H-imidazol-2-yl)-pyridin-4-yloxy]-1H-benzoimidazol-2-ylamino}-5-trifluoromethyl-phenol | 535.3 |
| 59a | 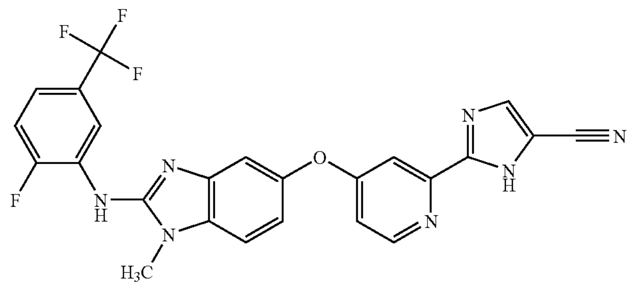 | 2-{4-[2-(2-Fluoro-5-trifluoro-methyl-phenylamino)-1-methyl-1H-benzoimidazol-5-yloxy]-pyridin-2-yl}-3H-imidazole-4-carbonitrile | 494.1 |
| 59b | 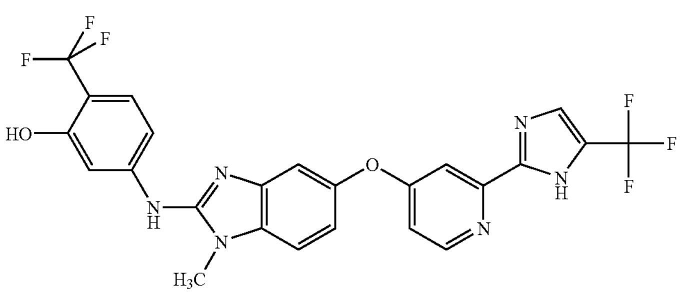 | 3-{1-Methyl-5-[2-(5-trifluoro-methyl-1H-imidazol-2-yl)-pyridin-4-yloxy]-1H-benzoimidazol-2-ylamino}-6-trifluoromethyl-phenol | 535.3 |

Example 60

Preparation of N-(4-hydroxy-2-nitrophenyl)-formamide

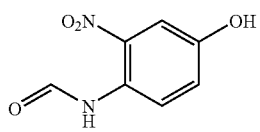

N-(4-hydroxy-2-nitrophenyl)-formamide can be prepared according to the following procedure:

1. Set up a 3-L, 5-necked reaction flask fitted with an internal temperature probe, temperature controller, heating mantle, condenser, mechanical stirrer, 1-L addition funnel and a nitrogen inlet. The reactor is with nitrogen for 5 minutes.
2. Charge acetic anhydride (245 mL) to the flask. Stir under nitrogen.
3. Charge formic acid (125 mL) in one portion (an exotherm is observed due to the mixing and the reaction between acetic anhydride and formic acid).
4. Set internal temperature (IT) end point to 60° C. and start heating. After the internal temperature (IT) reaches 60° C., stir and maintain for another 2 hours.
5. Cool contents with an ice bath.
6. When IT reaches ambient temperature (ca 20° C.), start adding a solution of 4-amino-3-nitrophenol (160 g) in 700 mL of anhydrous THF (tetrahydrofuran) via the 1-L addition funnel in portions so that IT does not exceed 40° C. The product starts to precipitate out as a yellow solid.
7. When the addition is completed, replace the ice bath with a heating mantle. Set IT end point at 60° C. and start heating.
8. Monitor the reaction progress by HPLC. The reaction normally takes less than 1 hour.
9. When the starting material is <1 area %, add 500 mL of water. Cool to room temperature with an ice bath.
10. Collect the product by vacuum filtration. Wash the filter cake with 3×200 mL of water. Air-dry, and further dry in an oven at 50° C. at 27 in. Hg vacuum with a gentle air or nitrogen bleed until a consistent weight is reached.

Example 61

Preparation of 4-methylamino-3-nitrophenol

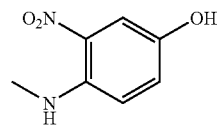

4-Methylamino-3-nitrophenol can be prepared according to the following procedure:
1. Set up a 500 mL, 3-necked reaction flask fitted with an internal temperature probe, and a nitrogen inlet. Flush the reactor with nitrogen for 5 minutes.
2. Charge N-(4-hydroxy-2-nitrophenyl)-formamide (5 g) and anhydrous THF (tetrahydrofuran, 100 mL) to the reactor. Stir under $N_2$ to afford a yellow slurry.
3. Add the boron trifluoride diethyl etherate (3.83 mL) via syringe slowly.
4. Stir the reaction mixture for 30 minutes at room temperature.
5. Add the sodium borohydride (1.04 g) portion wise via an addition funnel.
6. Stir the reaction for one hour and monitor the reaction by HPLC every hour thereafter (reaction typically takes 3 hours).
7. When the HPLC sample shows the starting material is less then 1.0% slowly add 1 M HCl (40 mL) via a syringe over a period of 10 minutes.
8. Stir for 60 minutes.
9. Add 1 M NaOH as needed via a syringe to bring pH to 7±0.5.
10. Pour the reaction mixture into a 500 mL round bottom flask and concentrate under reduced pressure (20 mm Hg, at 25° C.) until ca 100 mL of clear liquid is removed.
11. Add water (100 mL) to the reaction vessel. Cool to 0±2° C. with stirring. The product precipitates out as a red solid.
12. Collect the product by vacuum filtration through a coarse fritted funnel. Wash the filter cake with water (2×20 mL). Air-day and then dry in an oven at 50° C./27 in. Hg until a consistent weight is reached. Submit samples for analysis.

Example 62

Preparation of 4-chloropyridine-2-carbonyl chloride

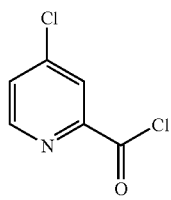

4-Chloropyridine-2-carbonyl chloride can be prepared according to the following procedure:
1. Set up a 5-L, 5-necked reaction flask fitted with an internal temperature (IT) probe, a temperature controller, heating mantle, condenser, mechanical stirrer, nitrogen inlet, gas outlet on top of the condenser that is connected to a 2-L, 2-neck liquid trap that is in turn connected to a 12-L scrubber filled with approx. 6 liters of 8 M NaOH solution and stirred with a magnetic stirrer. Flush the reactor with nitrogen for 5 minutes and then shut off nitrogen flow.
2. Charge thionyl chloride (1.18 L) to the reactor, followed by potassium bromide (38.4 g) while maintaining moderate stirring (ca 200 rpm).
3. Charge picolinic acid (397 g) to the reactor.
4. Set the IT end point at 80° C. and start heating.
5. Take samples and monitor the reaction progress by HPLC. The reaction normally takes around 14 hours to go to completion. Extended heating will result in more di-chlorination.
6. When the reaction is deemed complete (less than 1% of picolinic acid is present in the reaction mixture), stop heating. Remove the heating mantle.
7. When the IT is below 30° C., transfer the liquid to a 3-L reaction flask. Rinse the 5-L reactor with 700 mL of toluene. Transfer the rinses to the 3-L flask. Remove excess $SOCl_2$ and toluene under reduced pressure. Repeat the process with 2×700 mL of toluene. Remove all solvent yielding a yellow-orange solid. Toluene (400 mL) was added to the reaction mixture. Resulting mixture was carried on to the next step.

Example 63

Preparation of 4-chloropyridine-2-carboxylic acid t-butyl ester

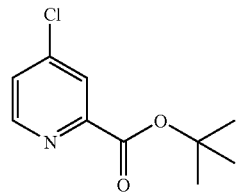

4-Chloropyridine-2-carboxylic acid t-butyl ester can be prepared according to the following procedure:
1. Equip a 12 L round bottom flask (4-necked) with a mechanical stirrer and a thermometer.
2. Charge the reactor with toluene (1 L), pyridine (977.7 g), and di-t-butyl dicarbonate $(BOC)_2O$ (855.5 g).
3. Cool the reactor so that the internal temperature is 0° C.
4. Add the 4-chloropyridine-2-carbonyl chloride (686 g) to the reactor at such a rate as to keep the internal temperature of the reaction below 5° C.
5. The reaction was allowed to slowly come up to room temp (20° C.) and stirred for 16 hours.
6. When the reaction is deemed complete using HPLC (starting material <0.5 area %) the reaction was washed with water (2×4 L), then 1 M HCl solution (2×2 L).
7. The reaction mixture was concentrated under reduced pressure to remove toluene and residual pyridine.

8. Toluene (500 mL) was added, and then the reaction mixture was concentrated under reduced pressure to obtain the desired product.

Example 64

Preparation of 4-(4-methylamino-3-nitrophenoxy)-pyridine-2-carboxylic acid t-butyl ester

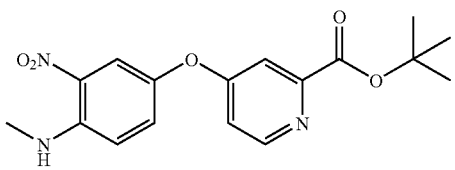

4-(4-Methylamino-3-nitrophenoxy)-pyridine-2-carboxylic acid t-butyl ester can be prepared according to the following procedure:
1. Equip a 3 L round bottom flask with a mechanical stirrer, thermometer and nitrogen inlet.
2. Charge the reactor with the $K_2CO_3$ (123 g).
3. Bring the reaction vessel under inert atmosphere.
4. Charge the reactor with 4-methylamino-3-nitrophenol (100 g), 4-chloropyridine-2-carboxylic acid t-butyl ester (127 g), and dry DMSO (1 L).
5. Stir the reaction vigorously and heat to 100° C.
6. When the reaction is deemed complete using HPLC (<0.5 area % 4-chloropyridine-2-carboxylic acid t-butyl ester), pour the hot reaction mixture into 3 L of stirring cool water (by volume).
7. Isolate the desired compound by filtration, as an orange to orange-brown solid.
8. Rinse the isolated solid with water (2×200 mL) followed by heptane (2×200 mL).
9. Dry material in vacuum oven (45-50° C. until constant weight is achieved.

Example 65

Preparation of 4-(4-(methylamino)-3-nitrophenoxy)pyridine-2-carbaldehyde

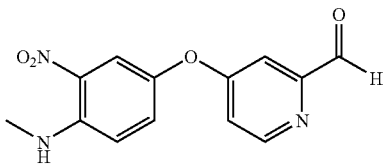

4-(4-(methylamino)-3-nitrophenoxy)pyridine-2-carbaldehyde can be prepared according to the following procedure:
1. Equip a 1000 mL round bottom flask with a nitrogen inlet, mechanical stirrer, and thermometer.
2. Charge the reactor with 4-(4-methylamino-3-nitrophenoxy)-pyridine-2-carboxylic acid t-butyl ester (10 g) via a powder funnel.
3. Add 2-methyl THF (100 mL) via a powder funnel.
4. Cool the reactor until an internal temperature of −25° C.
5. Add the DIBAL (diisobutylaluminum hydride, 1.5 M in toluene; 72 mL) via an addition funnel at such a rate as to keep the internal temperature under −15° C.
6. Analyze the reaction via HPLC or GC (gas chromatography), checking for the disappearance of ester.
7. Stir the reaction at −20° C., monitoring every hour.
8. If the reaction fails to progress after 2 hours, add another 0.5 equivalents of DIBAL (diisobutylaluminum hydride) and monitor the reaction. Keep repeating this step until all the ester has been consumed.
9. Once the reaction is complete quench slowly with MeOH (10 mL).
10. Add the potassium sodium tartrate (40 g) to 200 mL of water and stir to dissolve.
11. Add the aqueous solution to the reaction mixture and allow to warm to RT.
12. Add 2-methyl THF (100 mL) to the reaction vessel.
13. Heat the reaction to 50° C. for 1 hour with stirring.
14. Allow the phases to separate.
15. Remove the lower aqueous layer.
16. Filter the organic layer through a plug of celite.
17. Rinse the celite with 2-methyl THF (2×50 mL).
18. Add the reaction mixture to a 500 mL round bottom flask.
19. Concentrate the reaction mixture to 50 mL by distillation.
20. Cool the reaction mixture to 0° C. with stirring.
21. Stir the reaction mixture for 1 hour at 0° C.
22. Filter the reaction mixture through a course fritted filter.
23. Allow the solids to dry on the filter for 30 minutes to 1 hour.
24. Analyze the solids by GC and NMR to determine the % alcohol, slurrying in methanol at 30° C. for 1 hour (5 mL of methanol per g of compound) if necessary to remove alcohol impurity.

Example 66

Preparation of 4-(2-(5-(trifluoromethyl)-1H-imidazol-2-yl)pyridin-4-yloxy)-N-methyl-2-nitrobenzenamine

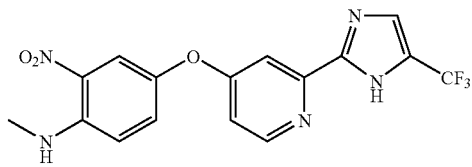

4-(2-(5-(trifluoromethyl)-1H-imidazol-2-yl)pyridin-4-yloxy)-N-methyl-2-nitrobenzenamine can be prepared according to the following procedure:
1. Equip a 2 L round bottom flask (3 necked) with a mechanical stirrer, internal temperature probe, temperature controller and condenser.
2. Charge the reactor with water (590 mL) via powder funnel.
3. Begin stirring the mixture and charge the reactor with sodium acetate (240 g).
4. Rinse the flask used for the sodium acetate charge with water (30 mL).
5. Heat the reaction to 50° C.
6. Add 3,3-dibromo-1,1,1-trifluoropropan-2-one (395 g) portion-wise at 50° C. keeping the internal temperature of the reaction under 100° C.
7. Heat the reaction to an internal temperature of 100° C.
8. After stirring the reaction for 1 hour at 100° C., remove a sample for analysis.
9. Keep stirring the reaction at 100° C. until the starting material is <1.5%.

10. Once the reaction is complete cool the reaction mixture to <65° C.
11. While the reaction is cooling, equip a 5 L round bottom flask jacketed 4 necked) with an internal temperature probe, temperature controller, reflux condenser and mechanical stirrer.
12. Charge the 5 L reactor with ethyl acetate (500 mL) via a powder funnel and begin stirring.
13. Charge the 5 L reactor with 4-(4-(methylamino)-3-nitrophenoxy)pyridine-2-carbaldehyde (200 g) via powder funnel.
14. Rinse the powder funnel with ethyl acetate (200 mL) into the 5 L reactor.
15. Charge the 5 L reactor with 95% ethanol (1.3 L).
16. Transfer the pyruvaldehyde reaction mixture from the 2 L reactor to the 5 L reactor. Temperature of the mixture at this point is 35° C.
17. Slowly add conc. NH$_4$OH (1.3 L) portion wise monitoring the temperature. The reaction is exothermic so the first 500 mL should be added in portions keeping the internal temperature under 50° C. The total addition time is 25 minutes. Elevated temperatures cause the final product to become redder.
18. Heat the 5 L reactor to 50° C.
19. Stir the reaction mixture at 50° C. Solution at this point is usually reddish-orange in color.
20. Monitor the reaction every hour until the reaction is complete.
21. Once the reaction is deemed complete, cool the reaction mixture to 0° C. for 2 hours.
22. Isolate the product by filtration through a coarse fritted glass filter.
23. Rinse the reactor with cold ethanol (150 mL). Transfer the rinse to the filter.
24. Charge the 5 L reactor with water (2 L).
25. Stir and cool the reactor to 10° C.
26. Transfer the wet cake from the filter to the 5 L reactor.
27. Stir at 10° C. for 60 minutes.
28. Filter the product through a coarse fritted glass filter.
29. Rinse the reactor with water (250 mL). Transfer the rinse to the filter.
30. Dry the wet cake on the filter for 1 hour.
31. Transfer the product to a 2 L round bottom flask (single neck) and tumble dry using a rotary evaporator with a bath temperature of 45° C. until a constant weight is recorded.

Example 67

Preparation of 4-(2-(5-(trifluoromethyl)-1H-imidazol-2-yl)pyridin-4-yloxy)-N1-methylbenzene-1,2-diamine

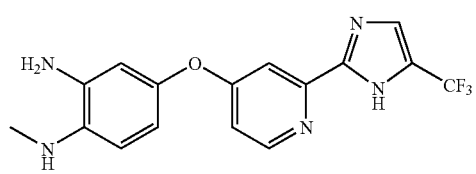

4-(2-(5-(trifluoromethyl)-1H-imidazol-2-yl)pyridin-4-yloxy)-N1-methylbenzene-1,2-diamine can be prepared according to the following procedure:

1. Equip a 2 L round bottom flask (4 neck) with a mechanical stirrer, internal temperature probe, temperature controller, nitrogen purge and reflux condenser.
2. Charge the reactor with EtOH (125 mL) via powder funnel. Begin stirring rapidly.
3. Charge the reactor with 4-(2-(5-(trifluoromethyl)-1H-imidazol-2-yl)pyridin-4-yloxy)-N-methyl-2-nitrobenzenamine (50 g) via powder funnel.
4. Heat the reaction to 50° C.
5. While the reaction is heating, charge a 250 mL Erlenmeyer with water (75 mL) via a powder funnel. Begin stirring rapidly.
6. Charge the 250 mL Erlenmeyer with 3.0 eq. sodium carbonate (41.92 g) via a powder funnel.
7. Stir the mixture until all the solids are dissolved.
8. Once the suspension reaches 50° C., transfer the sodium carbonate mixture from the 250 mL Erlenmeyer to the reaction mixture via powder funnel.
9. Charge a 250 mL Erlenmeyer with water (75 mL) via powder funnel. Begin stirring rapidly.
10. Charge the 250 mL Erlenmeyer with 1.0 eq. sodium dithionite (22.95 g) via powder funnel just before addition to the reaction flask.
11. Rapidly stir the solids until they are mostly dissolved.
12. Quickly transfer the sodium dithionite mixture from the 250 mL Erlenmeyer to the reaction mixture via powder funnel.
13. Stir the reaction at 50° C. for 30 minutes.
14. Charge a 250 mL Erlenmeyer with water (75 mL) via powder funnel. Begin stirring rapidly.
15. Charge the 250 mL Erlenmeyer with 1.0 eq. sodium dithionite (22.95 g) via powder funnel just before addition to the reaction flask.
16. Rapidly stir the solids until they are mostly dissolved.
17. Quickly transfer the sodium dithionite mixture from the 250 mL Erlenmeyer to the reaction mixture via powder funnel.
18. Stir the reaction at 50° C. for 30 minutes.
19. Charge a 250 mL Erlenmeyer with water (150 mL) via powder funnel.
20. Charge the 250 mL Erlenmeyer with 2.0 eq. sodium dithionite (45.90 g) via powder funnel just before addition to the reaction flask.
21. Rapidly stir the solids until they are mostly dissolved.
22. Quickly transfer the sodium dithionite mixture from the 250 mL Erlenmeyer to the reaction mixture via powder funnel.
23. Stir the reaction at 50° C. for 60 minutes.
24. A sample is taken to verify the reaction completion.
25. If the reaction is ≧98% complete, go to step 36. If not then continue to step 26.
26. Charge the 2 L reaction flask with 1.0 eq. sodium dithionite (22.95 g) via powder funnel.
27. Rapidly stir the reaction mixture at 50° C. for 60 minutes.
28. A sample is taken to verify the reaction completion.
29. If the reaction is ≧98% complete, go to step 36. If not then continue to step 30.
30. Charge the 2 L reaction flask with 1.0 eq. sodium carbonate (13.97 g) via a powder funnel.
31. Rapidly stir the reaction mixture at 50° C. for 15 minutes.
32. Charge the 2 L reaction flask with 1.0 eq. sodium dithionite (22.95 g) via powder funnel.
33. Rapidly stir the reaction mixture at 50° C. for 60 minutes.
34. A sample is taken to verify the reaction completion.
35. When the reaction is ≧98% complete, go to step 36
36. Once the reaction is deemed complete, charge the 2 L reaction flask with water (125 mL) via a powder funnel.

37. Cool the reaction mixture to 10° C. and stir for 1 hour.
38. Isolate the product by filtration through a course fritted glass filter.
39. Rinse the reactor with water (50 mL). Transfer the rinse to the filter.
40. Dry the wet cake on the filter until it no longer drips.
41. Charge the 2 L reaction flask with water (500 mL) via a powder funnel.
42. Transfer the cake back into the reaction flask via a powder funnel.
43. Stir material at room temperature for 60 min.
44. Isolate the product by filtration through a course fritted glass filter.
45. Rinse the reactor with water (25 mL). Transfer the rinse to the filter.
46. Dry the wet cake on the filter for about 1 hour.
47. Transfer the product to a 2 L round bottom flask (single neck) and slowly tumble dry using a rotary evaporator with a bath temperature of 50° C. until a constant weight is recorded.

Example 68

Preparation of {1-Methyl-5-[2-(5-trifluoromethyl-1H-imidazol-2-yl)-pyridin-4-yloxy]-1H-benzoimidazol-2-yl}-(4-trifluoromethyl-phenyl)-amine

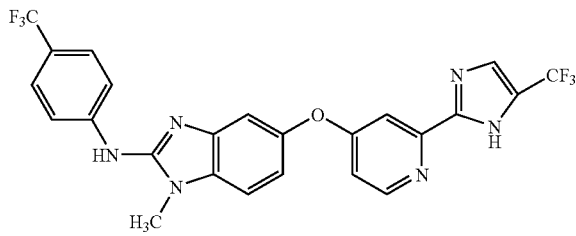

{1-Methyl-5-[2-(5-trifluoromethyl-1H-imidazol-2-yl)-pyridin-4-yloxy]-1H-benzo-imidazol-2-yl}-(4-trifluoromethyl-phenyl)-amine can be prepared according to the following procedure:
1. Equip a 2-L, 4-neck round bottom flask with a mechanical stirrer, internal temperature probe, temperature controller, nitrogen purge and condenser.
2. Charge the reactor with 4-(2-(5-(trifluoromethyl)-1H-imidazol-2-yl)pyridin-4-yloxy)-N1-methylbenzene-1,2-diamine (200 g) via powder funnel.
3. Charge the reactor with acetonitrile (1 L) via powder funnel.
4. Begin stirring the mixture at ambient temperature and under a nitrogen atmosphere.
5. After 20±5 min, charge the reactor with 4-trifluoromethylphenyl isothiocyanate (104 g) via powder funnel.
6. A sample is taken 30 min after addition of the isothiocyanate to verify reaction completion.
7. Once the reaction is complete, filter the mixture through a coarse fritted glass filter.
8. Rinse the reactor with acetonitrile (200 mL). Transfer the rinse to the filter.
9. Wash the removed solids with acetonitrile (200 mL).
10. Transfer the filtrate to a 3-L, 4-neck round bottom flask with a mechanical stirrer, internal temperature probe, temperature controller, nitrogen purge and condenser.
11. Charge the reactor with N,N-diisopropylethylamine via powder funnel.
12. Charge the reactor with 2-chloro-1,3-dimethylimidazolinium chloride via powder funnel in four equivalent portions every 10 min (total addition time of 30 min). After the final addition, allow the reaction mixture to stir an additional 10 min.
13. Heat the reaction to 50° C.±5° C.
14. A sample is taken 30 minutes after heating the mixture to verify reaction completion.
15. Once the reaction is complete, transfer the reaction mixture through an in-line 0.2 μm capsule filter to a 3-L round bottom flask equipped as in step 10.
16. Add the water via powder funnel.
17. Heat the reaction to 50° C.±5° C.
18. After heating for 2 h, allow the reaction mixture to cool to 20-25° C. and stir an additional 1 h.
19. Isolate the product by filtration through a medium fritted glass filter.
20. Rinse the reactor with 2:1 acetonitrile/water (300 mL). Transfer the rinse to the filter.
21. Wash the filter cake with 2:1 acetonitrile/water (300 mL).
22. Dry the wet cake on the filter for about 1 hour.
23. Transfer the product to a drying dish and dry the material in a vacuum oven at 70±5° C. with a small bleed of nitrogen until the amount of residual acetonitrile is less than 410 ppm.
24. To recrystallize, product is heated to reflux in 15 volumes (weight to volume) of EtOH in a reactor equipped with a mechanical stirrer, internal temperature probe, temperature controller, nitrogen purge and condenser.
25. The mixture is refluxed for 30 minutes when a distillation head is substituted for the condenser.
26. EtOH is distilled off until 4 volumes remain. Heating is stopped and one volume of water is added.
27. The mixture is allowed to cool to 0-5° C.
28. Isolate the product by filtration through a medium fritted glass filter.
29. Rinse the reactor with 4:1 EtOH/water (1 volume). Transfer the rinse to the filter.
30. Wash the filter cake with water (1 volume).
31. Dry the wet cake on the filter for about 1 hour.
32. Transfer the product to a drying dish and dry the material in a vacuum oven at 50° C.±5° C. with a small bleed of nitrogen until constant weight is attained.

Example 69

Preparation of {1-Methyl-5-[2-(5-trifluoromethyl-1H-imidazol-2-yl)-pyridin-4-yloxy]-1H-benzoimidazol-2-yl}-(4-trifluoromethyl-phenyl)-amine 4-Trifluoromethylphenyl isothiocyanate (200 mg, 1 mmol) was added to a mixture of 4-(2-(5-(trifluoromethyl)-1H-imidazol-2-yl)pyridin-4-yloxy)-N1-methylbenzene-1,2-diamine (350 mg, 1 mmol) in 3 mL of acetonitrile. The reaction was stirred for 20 min at ambient temperature and was monitored by HPLC. Triethylamine (0.3 mL, 2.2 mmol) was added followed by 2-chloro-1-methylpyridinium iodide (270 mg, 1.05 mmol). The reaction mixture was heated to 50° C. for 5 h. The heating was stopped and 1.5 mL of water was added. After stirring the mixture for 2 h, the solid was collected by filtration and washed with 2:1 acetonitrile/water (3×1 mL) to afford 317 mg (61%) of the title compound.

Example 70

Preparation of {1-Methyl-5-[2-(5-trifluoromethyl-1H-imidazol-2-yl)-pyridin-4-yloxy]-1H-benzoimidazol-2-yl}-(4-trifluoromethyl-phenyl)-amine 4-Trifluoromethylphenyl isothiocyanate (200 mg, 1 mmol) was added to a mixture of 4-(2-(5-(trifluoromethyl)-1H-imidazol-2-yl)pyridin-4-yloxy)-N1-methylbenzene-1,2-diamine (350 mg, 1 mmol) in 3 mL of acetonitrile. After stirring for 20 min at ambient temperature, HPLC analysis showed complete conversion. A mixture of thiourea (553 mg, 1 mmol) in POCl$_3$ (3 mL) was stirred at ambient temperature. After 4 h, the mixture was heated to approximately 50° C. After heating for 2 h and monitored by HPLC, the title compound was provided.

Example 71

Preparation of 4-[2-(2-fluoro-5-trifluoro-phenylamino)-1-methyl-1H-benzoimidazol-5-yloxy]-pyridine-2-carbonitrile

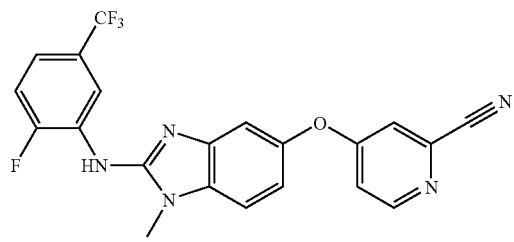

Step 1. Synthesis of 4-(4-Amino-3-nitro-phenoxy)pyridine-2-carbonitrile

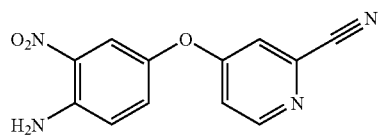

Potassium carbonate (9 g) was dried in vacuo with heating, cooled to room temperature under nitrogen. 4-Amino-3-nitrophenol (3.4 g), 4-chloro-2-cyanopyridine (3.0 g) and dimethylsulfoxide (30 mL, anhydrous) were added. The system was stirred under nitrogen as it was heated to 103° C., and held at this temperature for 1 hr. The reaction was then cooled to room temperature, poured onto ice/H$_2$O (500 mL) the precipitate was collected, washed (H$_2$O), dissolved (EtOAc), dried (Na$_2$SO$_4$), filtered and stripped to a solid. This was suspended (Et$_2$O), collected, air-dried 4.1 g (73.5%) and a second crop was collected (0.55 g, 10%). M/z=257 (M+1).

Step 2. Synthesis of N-[4-(2-Cyano-pyridin-4-yloxy)-2-nitro-phenyl]-2,2,2-trifluoro-N-methyl-acetamide

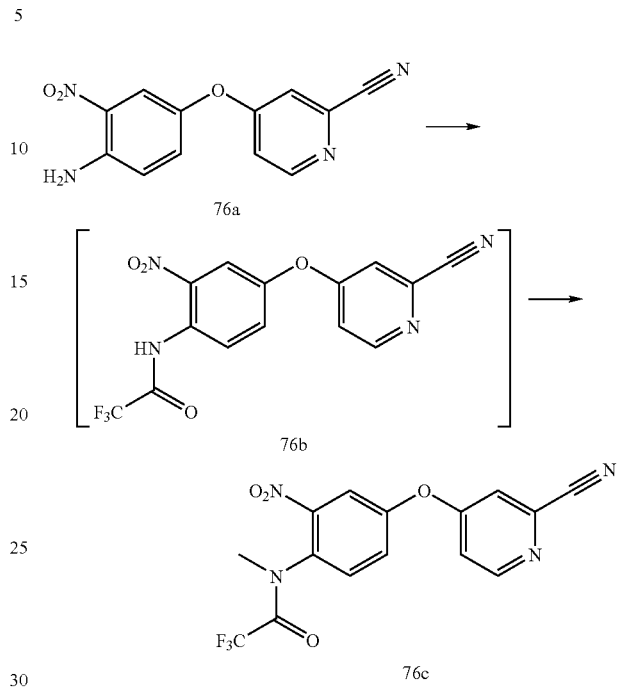

Potassium carbonate (1.6 g) was dried in vacuo with heating, cooled to room temperature and suspended in dichloromethane (30 mL) with 4-(4-amino-3-nitro-phenoxy)pyridine-2-carbonitrile (2.0 g) under nitrogen. This was cooled to 0° C. and neat trifluoroacetic anhydride (2.2 mL) was added. After 10 min at 0° C., the mixture was diluted with dichloromethane, washed (H$_2$O, aq. NaCl), dried (K$_2$CO$_3$), filtered and stripped to a yellow foam. M/z=353 (M+1). This product was used without purification. Iodomethane (0.53 mL) was added to a suspension of potassium carbonate (1.858 g) in dimethylformamide DMF (30 mL containing compound 76b (7.8 mmol) under nitrogen. The suspension stirred at room temperature overnight, then poured onto H$_2$O (300 mL), extracted (Et$_2$O, 3×150 mL), the combined extracts were washed (H$_2$O, aq. NaCl), dried (potassium carbonate), filtered and stripped to yield an orange oil (7.4922 g). m/z=367 (M+1).

Step 3. Synthesis of 4-(4-Methylamino-3-nitro-phenoxy)-pyridine-2-carbonitrile

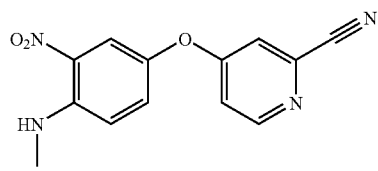

NaOH (1 mL, 1N aq.) was added dropwise to a solution of N-[4-(2-cyano-pyridin-4-yloxy)-2-nitro-phenyl]-2,2,2-trifluoro-N-methyl-acetamide (76c, 440 mg) in ethanol (6 mL) at room temperature. After 40 min, the mixture was diluted with H₂O (20 mL) and cooled to 0° C. Bright orange crystals were collected, washed (H₂O) and air-dried (311.1 mg 94%). m/z=271 (M+1)

Step 4. Synthesis of 4-[2-(2-fluoro-5-trifluoro-phenylamino)-1-methyl-1H-benzoimidazol-5-yloxy]-pyridine-2-carbonitrile

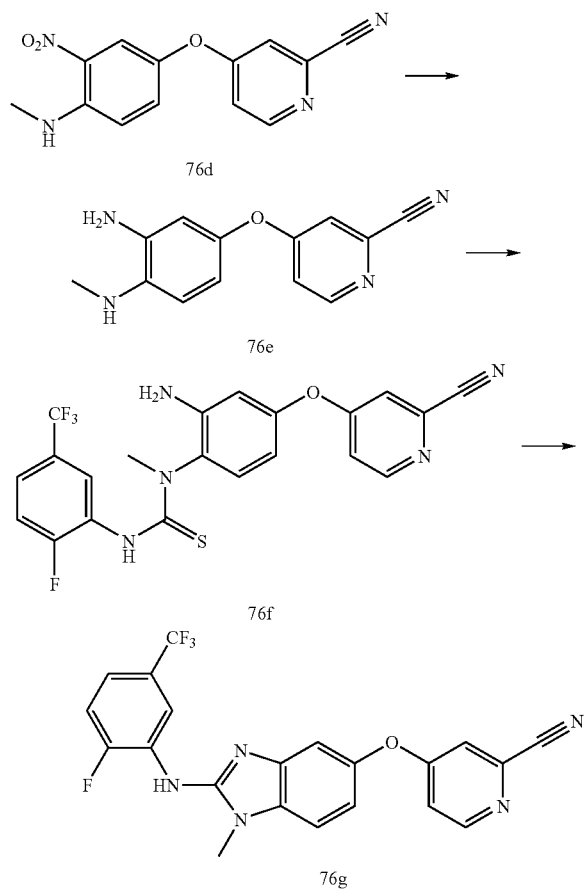

Palladium on carbon (46 mg, 10% w/w) was suspended in MeOH (2 mL) under nitrogen. The resulting suspension was added, under nitrogen, to a suspension of 4-(4-methylamino-3-nitro-phenoxy)-pyridine-2-carbonitrile (311 mg) in MeOH (3 mL) at room temperature. The atmosphere was exchanged with hydrogen, and the system stirred vigorously under 1 atm hydrogen for 1 h. The atmosphere was then exchanged for nitrogen, the mixture was filtered (celite) and the filtrate was used without further purification in the next reaction. M/z=242 (M+1). 2-fluoro-5-trifluoromethylphenylisothiocyanate (250 mg) was added to a solution of compound 76e in MeOH (10 mL). The solution was stirred at reflux for 2 h. Then, anhydrous FeCl₃ (1.3 eq., 244 mg) was added to the reaction and the resulting mixture was stirred at room temperature overnight. The crude reaction mixture was added to a separatory funnel containing EtOAc and water. The layers were separated and the aqueous phase was extracted with EtOAc. The organic layers were combined, washed with saturated aqueous Na₂CO₃ solution, water, and brine, then dried (MgSO₄), and concentrated. This material was chromatographed (gradient 0-5% MeOH in dichloromethane on silica gel) to isolate the desired compound in 28% yield from compound 76 g. m/z=428 (M+1).

Example 72

Preparation of 4-(2-(5-(trifluoromethyl)-1H-imidazol-2-yl)pyridin-4-yloxy)-N-methyl-2-nitrobenzenamine

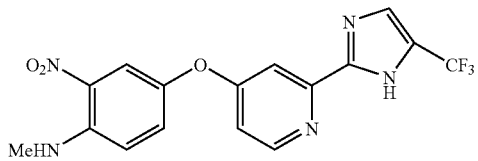

NaOMe (1.5 mL, 6.3 mmol, 25 wt% in MeOH) was added to a mixture of 4-(4-(methylamino)-3-nitrophenoxy)pyridine-2-carbonitrile (1.72 g, 6.3 mmol) in 1-PrOH (10 mL). The mixture was heated to 50° C. (internal temperature). After heating for 1 h, HPLC analysis indicated complete conversion of starting material. NH₄OAc (1.46 g, 18.9 mmol) was added and the mixture heated to 70° C. After 1 h at 70° C., the mixture was heated to 85° C. Simultaneously, 3-bromo-1,1,1-trifluoroacetone (0.8 mL, 7.56 mmol) was added in 4×0.2-mL portions every 30 min. The mixture was heated at 85° C. for 20 h. The mixture was then allowed to cool to ambient and water (10 mL) was added. After stirring for several hours, the mixture was cooled in an ice/water bath. After 1 h in the ice/water bath, the solid was collected by filtration and washed with 1:1 1-PrOH/water (2×7 mL). The solid was dried in a vacuum oven at 50° C. for ca. 16 h to afford 0.982 g (41%) of the title compound.

Example 73

Preparation of 4-chloro-2-(5-(trifluoromethyl)-1H-imidazol-2-yl)pyridine

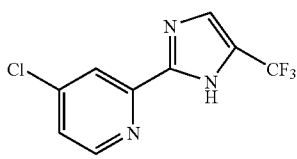

NaOMe (0.46 mL, 2 mmol, 25 wgt% in MeOH) was added to a mixture of 4-chloro-2-cyano-pyridine (277 mg, 2 mmol) in 1-PrOH (3 mL). The mixture was heated to 50° C. (Reaction-Block temperature). After heating for 1 h, HPLC analysis indicated complete conversion of starting material. The mixture was heated to 70° C. and NH₄OAc (462 mg, 6 mmol) was added. After 1 h at 70° C., the mixture was heated to 85° C. Simultaneously, 3-bromo-1,1,1-trifluoroacetone (0.25 mL, 2.4 mmol) was added in 4×0.063-mL portions every 30 min. The mixture was heated at 85° C. for ca. 20 h. The crude product was 72.4% (LCAP) by HPLC analysis and was confirmed by LC-MS analysis.

Example 74

4-Chloro-2-cyano-pyridine

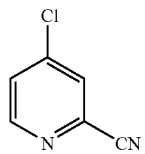

4-Chloro-2-pyridinecarboxamide (93.9 g, 0.6 moles) and TEA (125 mL, 0.9 moles) in EtOAc (500 mL) was cooled to 0.2° C. via an external chiller unit. TFAA (92 mL, 0.66 moles) was added via addition funnel over 40 min. The internal temperature rose to 10° C. during the addition. The temperature at the completion of the addition was 0.0° C. After addition, the chiller was turned off. After an additional 30 min, HPLC analysis showed 4.3% (LCAP) of the starting material. An additional 8.3 mL (0.06 moles) of TFAA was added. After stirring the reaction mixture for an additional 20 min, HPLC analysis indicated complete conversion. 10% Aqueous K$_2$CO$_3$ (w/v, 500 mL) was added. The internal temperature rose from 13.7 to 22.0° C. The mixture was transferred to a separatory funnel after stirring for 20 min. The layers were separated and the aqueous layer extracted with EtOAc (150 mL). The combined organic layers were washed with 10% aqueous citric acid (w/v, 300 mL), dried (Na$_2$SO$_4$), filtered, and concentrated. The crude product was dried in a vacuum oven at 50° C. for 16 h to afford 72.85 g (87%) of the title compound: $^1$H NMR (400 MHz, CDCl$_3$) δ 8.6 (m, 1H), 7.7 (m, 1H), 7.5 (m, 1H); $^{13}$C NMR (100 MHz, CDCl$_3$) δ 151.8, 145.3, 134.9, 128.7, 127.4, 116.1; HPLC>99% (LCAP).

Example 75

4-(4-Methylamino-3-nitro-phenoxy)-pyridine-2-carbonitrile

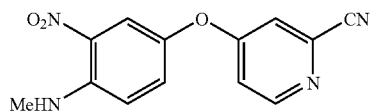

A mixture of 4-chloro-2-cyano-pyridine (6.9 g, 0.05 moles), 4-methylamino-3-nitrophenol (8.4 g, 0.05 moles), and K$_2$CO$_3$ (10.4 g, 0.075 moles) in DMSO (80 mL) was heated to 60° C. After 11.5 h, HPLC analysis indicated complete conversion of both starting materials. After cooling to 20° C., water (240 mL) was added to the reaction mixture. The temperature rose to 40° C. before decreasing to ambient temperature. The solid was collected by filtration and washed with water (2×40 mL). The solid was then slurried in heptane (40 mL). The solid was collected and washed with heptane (40 mL). The crude product was dried in a vacuum oven at 50° C. for 16 h to afford 10.33 g (76%) of the title compound: $^1$H NMR (400 MHz, DMSO-d$_6$) δ 8.5 (m, 1H), 8.2 (m, 1H), 7.9 (m, 1H), 7.7 (m, 1H), 7.5 (m, 1H), 7.2 (m, 1H), 7.1 (m, 1H), 3.0 (s, 3H); $^{13}$C NMR (100 MHz, DMSO-d$_6$) δ 165.1, 152.9, 144.4, 140.6, 134.1, 130.4, 130.1, 117.9, 117.1, 117.0, 116.5, 114.9, 29.8; APCI MS [M+H]$^+$=271; HPLC>99% (LCAP).

Example 76

4-(4-Methylamino-3-amino-phenoxy)-pyridine-2-carbonitrile

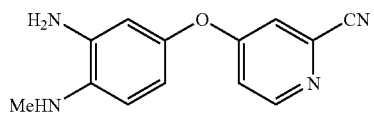

4-(4-Methylamino-3-nitro-phenoxy)-pyridine-2-carbonitrile (5.0 g, 0.019 moles) in EtOH (15 mL) was heated to 40° C. Na$_2$CO$_3$ (4.7 g, 0.044 moles) was added followed by H$_2$O (8.4 mL). Na$_2$S$_2$O$_4$ (3.3 g, 0.019 moles) was added followed by H$_2$O (10 mL). The temperature rose from 41.7 to 49.5° C. After cooling down to 41.7° C., Na$_2$S$_2$O$_4$ (3.3 g, 0.019 moles) was added followed by H$_2$O (10 mL). The temperature rose to 44.5° C. After cooling down to 36.7° C., Na$_2$S$_2$O$_4$ (6.6 g, 0.038 moles) was added followed by H$_2$O (20 mL). The temperature rose to 44.0° C. HPLC analysis showed 4.1% (LCAP) of the starting material. Additional Na$_2$S$_2$O$_4$ (3.3 g, 0.019 moles) was added. After stirring an additional 15 min, heat was removed and H$_2$O (12.5 mL) was added. At 25° C., additional Na$_2$CO$_3$ (1.3 g, 0.012 moles) was added and the mixture cooled in an ice/water bath. At less than 5° C., the mixture was allowed to age for 30 min (final temperature of 1.5° C.). The solid was collected by filtration and washed with H$_2$O (10 mL followed by 5 mL). The solid was dried on the filter for 30 min and then transferred to the reaction flask and H$_2$O (50 mL) added. The mixture was stirred for 45 min. The solid was then collected by filtration and washed with H$_2$O (2×10 mL). The crude product was dried in a vacuum oven at 50° C. for 16 h to afford 3.50 g (76%) of the title compound: $^1$H NMR (400 MHz, DMSO-d$_6$) δ 8.5 (m, 1H), 7.5 (m, 1H), 7.1 (m, 1H), 6.4 (m, 1H), 6.3 (m, 2H), 4.8 (s, 2H), 4.7 (s, 1H), 2.7 (s, 3H); APCI MS [M+H]=241; HPLC>99% (LCAP).

Example 77

4-[1-Methyl-2-(4-(trifluoromethyl)phenylamino)-1H-benzoimidazol-5-yloxy]-pyridine-2-carbonitrile

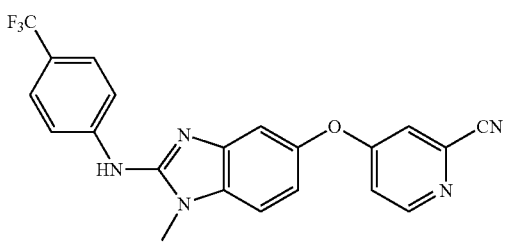

4-(Trifluoromethyl)phenyl isothiocyanate (9.65 g, 0.0475 moles) was added to a solution of 4-(4-methylamino-3-amino-phenoxy)-pyridine-2-carbonitrile (12.0 g, 0.05 moles) in MeCN (60 mL). HPLC analysis indicated complete conversion of the amine after 40 min. The mixture was filtered and the removed solids washed with MeCN (2×12 mL).

Example 78

{1-Methyl-5-[2-(5-trifluoromethyl-1H-imidazol-2-yl)-pyridin-4-yloxy]-1H-benzoimidazol-2-yl}-(4-trifluoromethyl-phenyl)-amine

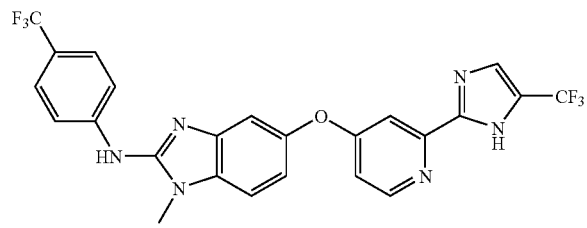

DIPEA (17.5 mL, 0.1 moles) was added to the filtrate. 2-Chloro-1,3-dimethylimidazolinium chloride (DMC) was added in 4×2.11-g portions (8.44 g, 0.05 moles) every 10 min. After the final addition, the mixture was allowed to stir an additional 10 min when HPLC analysis indicated complete conversion. The mixture was then heated to 50° C. (internal temperature). After 45 min at 50° C., HPLC analysis indicated complete conversion to the product. The mixture was allowed to cool to ambient temperature and then H$_2$O (45 mL) was added. The reaction mixture was initially homogeneous before compound began to precipitate from the mixture. After stirring for 2 h, the solid was collected by filtration and washed with 2:1 MeCN/H$_2$O (2×20 mL). The crude product was dried in a vacuum oven at 50° C. for 16 h to afford 16.10 g (78%) of the title compound $^1$H NMR (400 MHz, DMSO-d$_6$) δ 9.5 (m, 1H), 8.5 (m, 1H), 8.0 (m, 2H), 7.7 (m, 2H), 7.6 (m, 1H), 7.4 (m, 1H), 7.3 (m, 1H), 7.1 (m, 1H), 6.9 (m, 1H), 3.7 (m, 3H); APCI MS [M+H]$^+$=410; HPLC>99% (LCAP).

NaOMe (0.23 mL, 1 mmol, 25 wgt % in MeOH) was added to a mixture of Example 77 (409 mg, 1 mmol) in MeOH (4 mL). After 1 h at ambient temperature HPLC analysis indicated 46.2% (LCAP) of the starting material. The mixture was heated to 50° C. (Reaction-Block temperature). After heating for 1 h, HPLC analysis indicated 4.1% (LCAP) of the starting material remained. NH$_4$OAc (231 mg, 3 mmol) was added followed by 3-bromo-1,1,1-trifluoroacetone (0.13 mL, 1.2 mmol). The mixture was heated at 50° C. for about 20 h. Additional 3-bromo-1,1,1-trifluoroacetone (0.06 mL, 0.58 mmol) was added and the mixture heated to 60° C. After 24 h at 60° C., the mixture was allowed to cool to ambient temperature. Water (4 mL) was added followed by EtOAc (4 mL). The layers were separated and the aqueous layer extracted with EtOAc. The combined organic layers were dried (Na$_2$SO$_4$), filtered, and concentrated. The crude product was dissolved in IPA (4 mL). Methanesulfonic acid (0.020 mL) was added to 1 mL of solution of the IPA solution. The mixture was heated to 80° C. overnight. The mixture was then cooled to ambient temperature and concentrated to give the title compound: APCI MS [M+H]$^+$=519.

Example 79

{1-Methyl-5-[2-(5-trifluoromethyl-1H-imidazol-2-yl)-pyridin-4-yloxy]-1H-benzoimidazol-2-yl}-(4-trifluoromethyl-phenyl)-amine

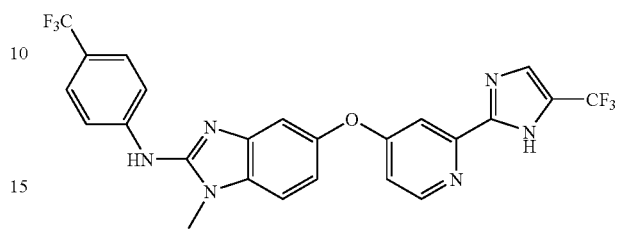

NaOMe (0.23 mL, 1 mmol, 25 wgt % in MeOH) was added to a mixture of Example 77 (409 mg, 1 mmol) in 1-PrOH (2 mL). The mixture was heated to 50° C. (Reaction-Block temperature). After heating for 1 h, HPLC analysis indicated complete conversion of the starting material. The mixture was heated to 70° C. and NH$_4$OAc (231 mg, 3 mmol) was added. After 1 h at 70° C., the mixture was heated to 85° C. Simultaneously, 3-bromo-1,1,1-trifluoroacetone (0.13 mL, 1.2 mmol) was added in 4×0.033-mL portions every 30 min. The mixture was heated at 85° C. for ca. 20 h. The mixture was allowed to cool to ambient temperature and water (2 mL) was added. After stirring for several hours, the solid was collected by filtration and washed with 1:1 1-PrOH/water (2×3 mL). The solid was dried in a vacuum oven at 50° C. for ca. 16 h to afford 0.11 g (21%) of the title compound.

While the preferred embodiment of the invention has been illustrated and described, it will be appreciated that various changes can be made therein without departing from the spirit and scope of the invention.

What is claimed is:

1. A method for preparing a compound or pharmaceutically acceptable salt thereof that is {1-methyl-5-[2-(5-trifluoromethyl-1H-imidazol-2-yl)-pyridin-4-yloxy]-1H-benzoimidazol-2-yl}-(4-trifluoromethyl-phenyl)-amine

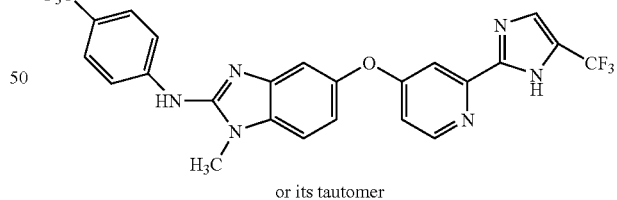

or its tautomer

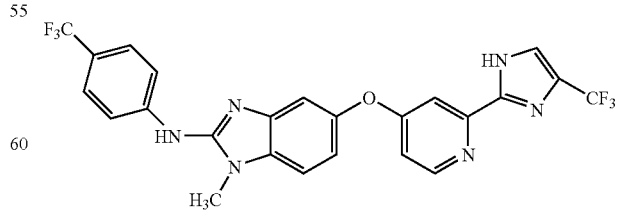

the method comprising:

(a) reacting a compound of Formula (II) with a compound of Formula (III) to provide a compound of Formula (IV)

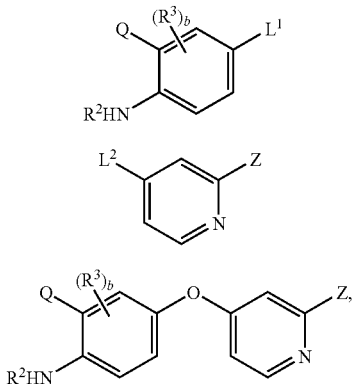

(II)

(III)

(IV)

wherein b is 0, $R^2$ is methyl, Q is $NH_2$ or $NO_2$; one of $L^1$ or $L^2$ is halo and the other of $L^1$ or $L^2$ is OH or an anion thereof; Z is cyano, $COOR^5$, $CH_2OR^5$, CHO, or imidazol-2-yl substituted with $CF_3$ and wherein $R^5$ is hydrogen or a hydroxy protecting group;

(b) when in the compound of Formula (IV) Z is cyano, $COOR^5$ or $CH_2OR^5$, reacting said compound with a reducing agent to provide a compound of Formula (IV) wherein Z is CHO;

(c) when in the compound of Formula (IV) Z is cyano, reacting the cyano functionality with an alkoxide to form an imidate, reacting the imidate with ammonium to form an amidino functionality and reacting said amidino functionality with a compound of Formula (Va) under imidazole ring forming conditions; or when in the compound of Formula (IV) Z is CHO, reacting said compound with a compound of Formula (Vb) to provide a compound of Formula (VI)

(Va)

(Vb)

(VI)

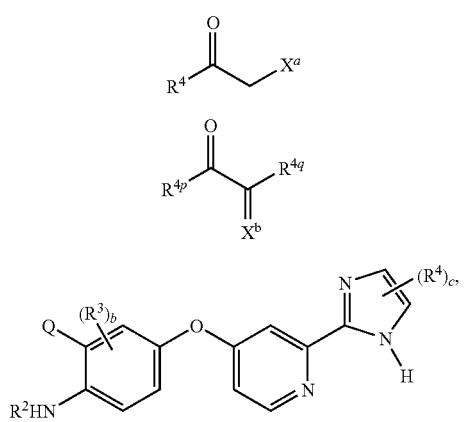

wherein b is 0, c is 1, $R^4$ is $CF_3$, $X^a$ in Formula (Va) is a leaving group and one of $R^{4p}$ and $R^{4q}$ in Formula (Vb) is H and the other of $R^{4p}$ and $R^{4q}$ is $CF_3$, and $X^b$ is =O or =NHOH;

(d) when in the compound of Formula (VI) Q is $NO_2$, reacting said compound with a reducing agent to a compound of Formula (VI) wherein Q is $NH_2$;

(e) reacting the compound of Formula (VI) wherein Q is $NH_2$ with a compound of Formula (VII) to provide a compound of Formula (VIII) or a tautomer thereof wherein a is 1, b is 0, c is 1, $R^1$ is 4-$CF_3$, $R^2$ is methyl, and $R^4$ is $CF_3$ (VII)

(VIII)

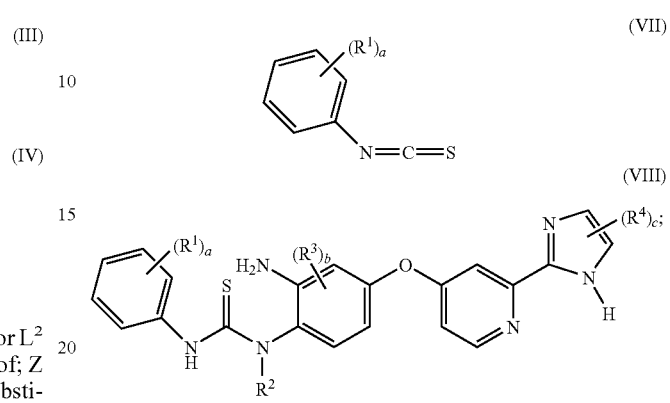

(f) reacting the compound of Formula (VIII) or a tautomer thereof with a desulfurizing agent to provide {1-methyl-5-[2-(5-trifluoromethyl-1H-imidazol-2-yl)-pyridin-4-yloxy]-1H-benzoimidazol-2-yl}-(4-trifluoromethyl-phenyl)-amine or its tautomer; and (g) optionally reacting {1-methyl-5-[2-(5-trifluoromethyl-1H-imidazol-2-yl)-pyridin-4-yloxy]-1H-benzoimidazol-2-yl}-(4-trifluoromethyl-phenyl)-amine or a tautomer thereof with an acid to give a pharmaceutically acceptable salt thereof.

2. The method of claim 1 wherein part (a) is carried out with organic or inorganic base in polar solvent.

3. The method of claim 2 wherein the inorganic base is selected from the group consisting of NaOH, KOH, $CaCO_3$, and $K_2CO_3$.

4. The method of claim 2 wherein the polar solvent is selected from the group consisting of dimethylsulfoxide and dimethylformamide.

5. The method of claim 1 wherein part (b) comprises reacting a compound of Formula (IV) when Z is $COOR^5$ with a reducing agent.

6. The method of claim 5 wherein $R^5$ is tert-butyl.

7. The method of claim 5 wherein the reducing agent is diisobutylaluminum hydride.

8. The method of claim 1 wherein part (c) is carried out with $NH_4OH$ in polar solvent.

9. The method of claim 8 wherein the polar solvent is a mixture of ethyl acetate and ethanol.

10. The method of claim 1 wherein part (d) comprises reacting a compound of Formula (VI) when Q is $NO_2$ with sodium dithionite.

11. The method of claim 1 wherein part (e) is carried out in acetonitrile.

12. The method of claim 1 wherein the desulfurizing agent in part (f) is selected from the group consisting of $FeCl_3$, 2-chloro-1-methylpyridinium iodide, 2-chloro-1,3-dimethylimidazolium chloride, and $POCl_3$.

* * * * *